United States Patent
Walter et al.

(10) Patent No.: US 7,087,638 B2
(45) Date of Patent: *Aug. 8, 2006

(54) PYRROLECARBOXAMIDES AND PYRROLETHIOAMIDES AS FUNGICIDES

(75) Inventors: Harald Walter, Rodersdorf (CH); Hermann Schneider, Heitersheim (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 33 days.

This patent is subject to a terminal disclaimer.

(21) Appl. No.: 10/680,346

(22) Filed: Oct. 7, 2003

(65) Prior Publication Data

US 2004/0106521 A1 Jun. 3, 2004

Related U.S. Application Data

(62) Division of application No. 10/181,702, filed as application No. PCT/EP01/00592 on Jan. 19, 2001, now Pat. No. 6,806,286.

(30) Foreign Application Priority Data

Jan. 21, 2000 (GB) .................. 0001447.2

(51) Int. Cl.
*C07D 409/12* (2006.01)
*A01N 43/10* (2006.01)

(52) U.S. Cl. ...................... 514/422; 548/527
(58) Field of Classification Search ........... 548/527, 548/235, 247, 127; 546/276.4
See application file for complete search history.

(56) References Cited

U.S. PATENT DOCUMENTS

| | | |
|---|---|---|
| 5,330,995 A | 7/1994 | Eicken et al. |
| 5,480,897 A | 1/1996 | Eicken et al. |
| 5,556,988 A | 9/1996 | Eicken et al. |
| 5,589,493 A | 12/1996 | Eicken et al. |
| 5,998,450 A * | 12/1999 | Eicken et al. ............... 514/355 |
| 6,365,620 B1 * | 4/2002 | Eberle et al. ............... 514/422 |

FOREIGN PATENT DOCUMENTS

| | | |
|---|---|---|
| EP | 566138 A | 10/1993 |
| EP | 737683 | 10/1996 |
| WO | WO 93 11117 | 6/1993 |
| WO | WO 00 09482 | 2/2002 |

* cited by examiner

*Primary Examiner*—Kamal A. Saeed
*Assistant Examiner*—Nyeemah Grazier
(74) *Attorney, Agent, or Firm*—Rebecca A. Gegick

(57) ABSTRACT

Novel pyrrole derivatives of formula I

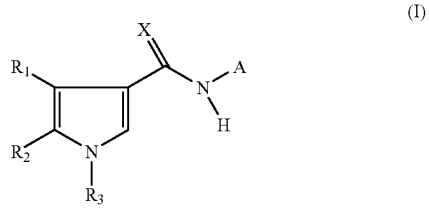

wherein
X is oxygen or sulfur;
$R_1$ is $C_1$–$C_4$alkyl unsubstituted or substituted, with the exception of $CF_3$; $C_3$–$C_6$cycloalkyl unsubstituted or substituted; or halogen;
$R_2$ is hydrogen, $C_1$–$C_4$alkyl unsubstituted or substituted, $C_1$–$C_4$alkoxy unsubstituted or substituted, cyano or halogen;
$R_3$ is $C_1$–$C_4$alkyl unsubstituted or substituted; and
A is orthosubstituted aryl; orthosubstituted heteroaryl; bicycloaryl unsubstituted or substituted; or bicycloheteroaryl unsubstituted or substituted.

The novel compounds have plant-protective properties and are suitable for protecting plants against infestations by phytopathogenic microorganisms.

7 Claims, No Drawings

PYRROLECARBOXAMIDES AND PYRROLETHIOAMIDES AS FUNGICIDES

The present invention relates to novel substituted pyrrolecarboxamides or pyrrolethioamides which have microbicidal activity, in particular fungicidal activity. The invention also relates to the preparation of these substances, to agrochemical compositions which comprise at least one of the novel compounds as active ingredient, to the preparation of the compositions mentioned and to the use of the active ingredients or compositions in agriculture and horticulture for controlling or preventing infestation of plants by phytopathogenic microorganisms, preferably fungi.

The pyrrolecarboxamides (thioamides) of the present invention have the general formula I

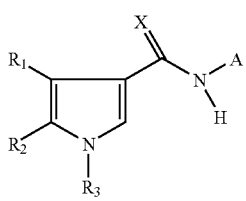

wherein
X is oxygen or sulfur;
$R_1$ is $C_1-C_4$alkyl unsubstituted or substituted, with the exception of $CF_3$; $C_3-C_6$cycloalkyl unsubstituted or substituted; or halogen;
$R_2$ is hydrogen, $C_1-C_4$alkyl unsubstituted or substituted, $C_1-C_4$alkoxy unsubstituted or substituted, cyano or halogen;
$R_3$ is $C_1-C_4$alkyl unsubstituted or substituted; and
A is orthosubstituted aryl; orthosubstituted heteroaryl; bicycloaryl unsubstituted or substituted; or bicycloheteroaryl unsubstituted or substituted.

Surprisingly, it has now been found that the compounds of formula (I) exhibit improved biological properties which render them more suitable for the practical use in agriculture and horticulture.

Where asymmetrical carbon atoms are present in the compounds of formula I, these compounds are in optically active form. The invention relates to the pure isomers, such as enantiomers and diastereomers, as well as to all possible mixtures of isomers, e.g. mixtures of diastereomers, racemates or mixture of racemates.

Within the present specification alkyl denotes methyl, ethyl, n-propyl, isopropyl, n-butyl, sec-butyl, isobutyl and tert-butyl. Non-branched alkyl is preferred. Alkyl as part of other radicals such as alkoxy, haloalkyl, alkylcycloalkyl, alkylcycloalkoxy, etc. is understood in an analogous way. Halogen will be understood generally as meaning fluoro, chloro, bromo or iodo. Fluoro, chloro or bromo are preferred meanings. Halogen as part of other radicals such as haloalkyl, haloalkoxy, haloalkenyl, haloalkenyloxy, haloaryl or haloheteroaryl, etc. is understood in an analogous way. Haloaryl or haloheteroaryl designates mono- to five times halo-substituted aryl, whereby the halogens are independently chosen. Where more than two halogens are present, the halogens are preferably the same, e.g. trifluorophenyl, trichlorophenyl, tetrachlorophenyl or perchlorophenyl. Haloalkyl is a monohalogenated to perhalogenated alkyl radical, such as, inter alia, fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl, 3,3,3-trifluoropropyl. Haloalkoxy is a monohalogenated to perhalogenated alkoxy radical, such as, inter alia, $OCH_2F$, $OCHF_2$, $OCF_3$, $OCHFCH_3$, $OCH_2CH_2Br$, $OCF_2CHFCl$.

Substituted alkyl will be understood as for example haloalkyl, alkoxy-alkyl, haloalkoxy-alkyl.

Cycloalkyl is, depending on the ring size, cyclopropyl, cyclobutyl, cyclopentyl, cyclohexyl or cycloheptyl. Substituted cycloalkyl will be understood for example as alkyl-cycloalkyl, haloalkyl-cycloalkyl, alkoxy-cycloalkyl, haloalkoxy-cycloalkyl, halo-cycloalkyl, alkoxyalkyl-cycloalkyl, haloalkoxyalkyl-cycloalkyl.

Alkenyl will be understood as meaning straight-chain or branched alkenyl such as allyl, methallyl, 1-methylvinyl or but-2-en1-yl. Preferred alkenyl radicals contain 3 to 4 carbon atoms in the chain.

Alkynyl can likewise, in accordance with the number of carbon atoms, be straight-chain or branched and is typically propargyl, but-1-yn-1-yl or but-1-yn-3yl.

Aryl is phenyl or naphthyl.

Heteroaryl will be understood as a 5- to 10 membered ring that may contain up to 3 heteroatoms, such as nitrogen, oxygen or sulfur. The following list of examples is not exhaustive: furyl, thienyl, imidazolyl, pyrazolyl, thiazolyl, isothiazolyl, oxazolyl, isoxazolyl, oxadiazolyl, thiadiazolyl, triazolyl, tetrazolyl, pyrrolyl, dithiolyl, oxathiolyl, dioxazolyl, oxathiazolyl, oxathiolyl, pyridyl, pyridazinyl, pyrimidinyl, pyrazinyl, triazinyl, indolyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl, naphthyridinyl, isobenzofuranyl, isoindolyl, benzothiadiazolyl, benzisoxazolyl, benzothienyl, purinyl, 5,6-dihydro-1,4,2-dioxazinyl, and the like.

Bicycloaryl or bicycloheteroaryl will be understood as a 6-membered aryl or 6-membered heteroaryl ring, wherein it may contain up to 3 heteroatoms such as nitrogen, oxygen or sulfur, and which is fused to an additional ring. The fused ring may be aromatic, partially hydrogenated or completely saturated and may be a ring from 5 to 7 ring members, of which up to 3 members may be heteroatoms selected from he group nitrogen, oxygen and sulfur. The following list of examples is not exhaustive: dihydroisobenzofuranyl, dihydroisoindolyl and the like.

Substituted aryl, substituted heteroaryl, substituted bicycloaryl or substituted bicycloheteroaryl will be understood as substituted by, inter alia, cycloalkyl, cycloalkenyl, cycloalkadienyl, phenyl, heteroaryl, cyano, nitro, halogen, alkyl, haloalkyl, alkoxy, haloalkoxy, alkoxyalkyl, haloalkoxyalkyl, alkenyl, alkynyl.

Preferred embodiment of compounds of formula I are those wherein
X is oxygen or sulfur; or
X is oxygen; or
X is sulfur; or
$R_1$ is $C_1-C_4$alkyl unsubstituted or substituted, with the exception of $CF_3$; $C_3-C_6$cycloalkyl unsubstituted or substituted; or halogen; or
$R_1$ is $C_1-C_4$alkyl; $C_1-C_4$haloalkyl; $C_1-C_4$alkoxy-$C_1-C_4$alkyl; $C_1-C_4$haloalkoxy-$C_1-C_4$alkyl; $C_3C_6$cycloalkyl unsubstituted or substituted by $C_1-C_4$alkyl, $C_1-C_4$haloalkyl, $C_1-C_4$alkoxy $C_1-C_4$haloalkoxy, $C_1-C_4$alkoxy-$C_1-C_4$alkyl, $C_1-C_4$haloalkoxy-$C_1-C_4$alkyl or halogen; or halogen; or
$R_1$ is $C_1-C_3$alkyl; $C_1-C_3$haloalkyl; $C_3-C_6$cycloalkyl unsubstituted or substituted by $C_1-C_3$alkyl, $C_1-C_3$haloalkyl or halogen; or $R_1$ is $C_1$–$C_2$alkyl, $C_1$–$C_3$haloalkyl or cyclopropyl; or $R_1$ is methyl, ethyl, $CFH_2$ or $CF_2H$; or $R_2$ is hydrogen, $C_1$–$C_4$alkyl, $C_1$–$C_4$haloalkyl, $C_1$–$C_4$alkoxy, $C_1$–$C_4$haloalkoxy, $C_1$–$C_4$alkoxy-$C_1$–$C_4$alkyl, $C_1$–$C_4$haloalkoxy-$C_1$–$C_4$alkyl, cyano or halogen; or $R_2$ is hydrogen, $C_1$–$C_4$alkyl or $C_1$–$C_4$haloalkyl; or $R_2$ is hydrogen or $C_1$–$C_3$alkyl; or $R_2$ is hydrogen; or $R_3$ is $C_1$–$C_4$alkyl unsubstituted or substituted; or $R_3$ is $C_1$–$C_4$alkyl, $C_1$–$C_4$haloalkyl, $C_1$–$C_4$alkoxy-$C_1$$C_4$alkyl or $C_1$–$C_4$haloalkoxy-$C_1$–$C_4$alkyl; or $R_3$ is $C_1$–$C_4$alkyl, $C_1$–$C_3$haloalkyl or $C_1$–$C_3$alkoxy-$C_1$–$C_3$alkyl; or $R_3$ is $C_1$–$C_3$alkyl or $C_1$–$C_3$alkoxy-$C_1$–$C_3$alkyl; or $R_3$ is methyl or $CH_2OCH_3$; or A is orthosubstituted aryl; orthosubstituted heteroaryl; bicycloaryl unsubstituted or substituted; or bicycloheteroaryl unsubstituted or substituted; or A is a group

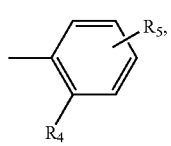
(A1)

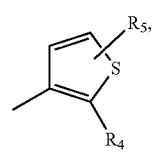
(A2)

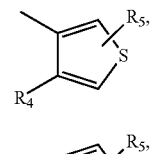
(A3)

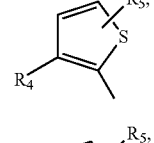
(A4)

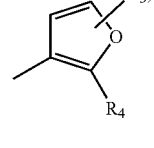
(A5)

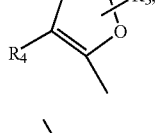
(A6)

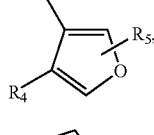
(A7)

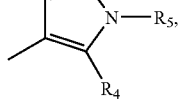
(A8)

-continued

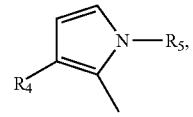
(A9)

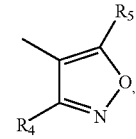
(A10)

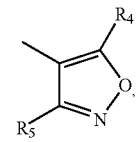
(A11)

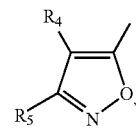
(A12)

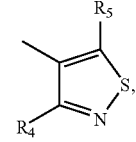
(A13)

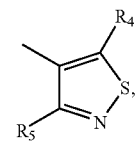
(A14)

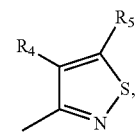
(A15)

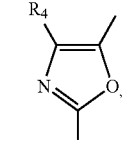
(A16)

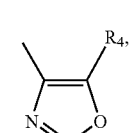
(A17)

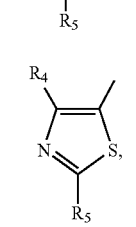
(A18)

-continued (A19) 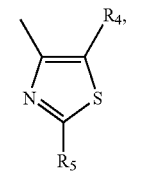

(A20) 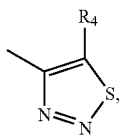

(A21) 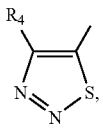

(A22) 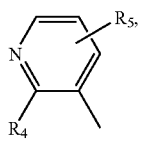

(A23) 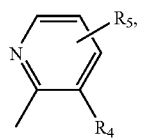

(A24) 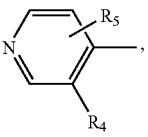

(A25) 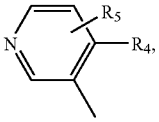

(A26) 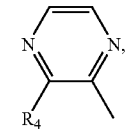

(A27) 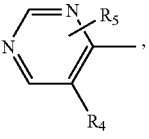

(A28) 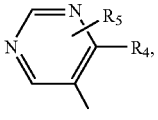

(A29) 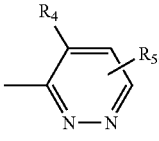

(A30) 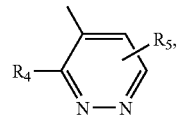

(A31)

(A32)

(A33)

or

A is A1, A2, A3, A5, A8, A10, A13, A14, A17, A18, A20, A21, A22, A24, A25, A26, A27, A29, A31, A32 or A33; or

A is A1, A2, A3, A17, A20, A21, A24, A25, A26, A27, A31 or A33; or A is A31 or A33; or $R_4$ is $C_3$–$C_7$cycloalkyl, $C_4$–$C_7$cycloalkenyl, $C_5C_7$cycloalkadienyl wherein the cycloalkyl group can be mono- to pentasubstituted by halogen, hydroxy, $C_1$–$C_4$alkyl, $C_1$–$C_4$alkoxy, $C_1$–$C_4$haloalkoxy, $C_2$$C_4$alkenyl, $C_2C_5$alkynyl, $C_1C_4$haloalkyl; phenyl unsubstituted or substituted by halogen, nitro, cyano, CHO, $C_1$–$C_4$alkyl, $C_1$–$C_4$alkoxy, $C_1$–$C_4$haloalkoxy, $C_2$–$C_5$alkenyl, $C_2$–$C_5$alkynyl, $C_1$–$C_4$haloalkyl, COO$C_1$–$C_4$alkyl, $C_1C_4$alkoxy-$C_1$–$C_4$alkyl, $C_1$–$C_4$alkyl-$C_1$–$C_4$alkoxy, $C_1$–$C_4$haloalkoxy-$C_1$–$C_4$alkyl, $C_1$–$C_4$haloalkyl-$C_1$–$C_4$alkoxy; thienyl, furyl, pyrrolyl, pyrazolyl, oxazolyl, thiazolyl, isoxazolyl, isothiazolyl, thiadiazolyl, imidazolyl, triazinyl, pyridyl, pyrazinyl, pyridazinyl or pyrimidinyl which are unsubstituted or substituted by halogen, $C_1$–$C_6$haloalkyl, $C_1$–$C_6$alkyl, $C_2$–$C_5$alkenyl, $C_2$–$C_5$alkynyl, nitro, cyano, hydroxy, CHO, $C_1$–$C_6$alkoxy, COO$C_1$–$C_6$alkyl, $C_1$–$C_4$alkoxy-$C_1$–$C_4$alkyl, $C_1$–$C_4$haloalkoxy-$C_1$–$C_4$alkyl or $C_1$–$C_6$haloalkoxy; or $R_4$ is $C_5$–$C_7$cycloalkyl, unsubstituted or mono- to trisubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; $C_5$–$C_7$cycloalkenyl, unsubstituted or mono- to trisubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; $C_5$–$C_7$cycloalkadienyl, unsubstituted or mono- to trisubstituted by halogen, hydroxy, $C_1$–$C_4$alkyl, $C_1$–$C_4$alkoxy, $C_1$–$C_4$haloalkoxy, $C_2$–$C_4$alkenyl, $C_2$–$C_4$alkynyl or $C_1$–$C_4$haloalkyl; phenyl which is unsubstituted or substituted by halogen, $C_1$–$C_4$alkyl, $C_1$–$C_4$alkoxy, $C_1$–$C_4$haloalkoxy or $C_1$–$C_4$haloalkyl; thienyl, furyl, oxazolyl, isoxazolyl, thiadiazolyl, triazinyl, pyridyl, pyrazinyl, pyridazinyl or pyrimidinyl which are unsubstituted or substituted by halogen, $C_1-C_4$haloalkyl, $C_1-C_4$alkyl, hydroxy, $C_1-C_4$alkoxy or $C_1-C_4$haloalkoxy; or $R_4$ is cyclohexyl, cyclohexenyl or cyclohexadienyl, which are unsubstituted or mono- to disubstituted by chloro, bromo, $C_1-C_2$alkyl, $C_1-C_2$haloalkyl or $C_1-C_2$haloalkoxy; thienyl, furyl, triazinyl, pyridyl, pyrazinyl, pyridazinyl or pyrimidinyl which are unsubstituted or substituted by halogen, $C_1-C_4$alkyl, $C_1-C_4$haloalkyl or $C_1-C_4$haloalkoxy; or $R_4$ is phenyl substituted by halogen; $C_5-C_7$cycloalkyl; or halothienyl; or $R_5$ is hydrogen, cyano, nitro, halogen, $C_1-C_4$haloalkyl, $C_1-C_4$alkyl, $C_1-C_4$alkoxy-$C_1-C_4$alkyl, $C_1-C_4$haloalkoxy-$C_1-C_4$alkyl, $C_1-C_4$alkoxy or $C_1-C_4$haloalkoxy; or $R_5$ is hydrogen, halogen, $C_1-C_4$alkyl, $C_1-C_4$haloalkyl, $C_1-C_4$alkoxy or $C_1-C_4$haloalkoxy; or $R_5$ is hydrogen, halogen, $C_1-C_3$alkyl, $C_1-C_3$haloalkyl, $C_1-C_3$alkoxy or $C_1-C_3$haloalkoxy; or $R_6$, $R_7$, $R_8$, $R_9$ and $R_{10}$ are identical or different and are each independently of the others hydrogen, halogen, $C_1-C_4$haloalkyl, $C_1-C_4$alkyl, $C_2-C_5$alkenyl, $C_2-C_5$alkynyl, $C_1-C_4$alkoxy, $C_1-C_4$alkoxy-$C_1-C_4$alkyl, $C_1-C_6$haloalkoxy-$C_1-C_4$alkyl, $C_1-C_4$haloalkoxy or $C_3-C_7$cycloalkyl; or $R_6$, $R_7$, $R_8$, $R_9$ and $R_{10}$ are identical or different and are each independently of the others hydrogen, $C_1-C_4$alkyl, $C_1-C_4$alkoxy, $C_1-C_4$haloalkyl or $C_1-C_4$haloalkoxy; or $R_6$, $R_7$, $R_8$, $R_9$ and $R_{10}$ are identical or different and are each independently of the others hydrogen or $C_1-C_3$alkyl.

Within the group of compounds of formula I those compounds are preferred wherein:

$R_1$ is $C_1-C_4$alkyl; $C_1-C_4$haloalkyl; $C_1-C_4$alkoxy-$C_1-C_4$alkyl; $C_1-C_4$haloalkoxy-$C_1-C_4$alkyl; $C_3-C_6$cycloalkyl unsubstituted or substituted by $C_1-C_4$alkyl, $C_1-C_4$haloalkyl, $C_1-C_4$alkoxy, $C_1-C_4$haloalkoxy, $C_1-C_4$alkoxy-$C_1-C_4$alkyl, $C_1-C_4$haloalkoxy-$C_1-C_4$alkyl or halogen; or halogen;

$R_2$ is hydrogen, $C_1-C_4$alkyl, $C_1-C_4$haloalkyl, $C_1-C_4$alkoxy, $C_1-C_4$haloalkoxy, $C_1-C_4$alkoxy-$C_1-C_4$alkyl, $C_1-C_4$haloalkoxy-$C_1-C_4$alkyl, cyano or halogen;

$R_3$ is $C_1-C_4$alkyl, $C_1-C_4$haloalkyl, $C_1-C_4$alkoxy-$C_1-C_4$alkyl or $C_1-C_4$haloalkoxy-$C_1-C_4$alkyl;

A is a group

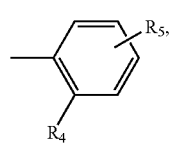 (A1)

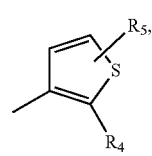 (A2)

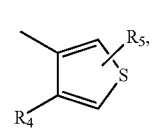 (A3)

-continued

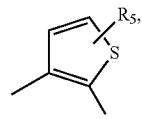 (A4)

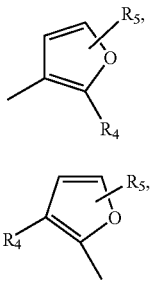 (A5)

(A6)

(A7)

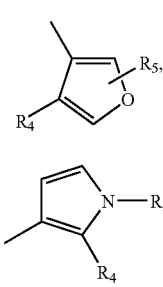 (A8)

(A9)

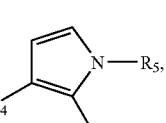 (A10)

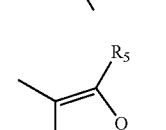 (A11)

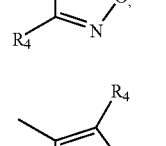 (A12)

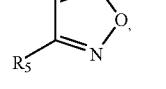 (A13)

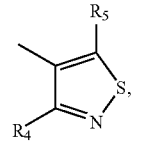 (A14)

-continued

 (A15)

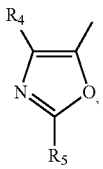 (A16)

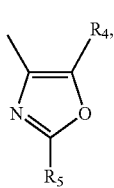 (A17)

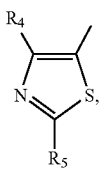 (A18)

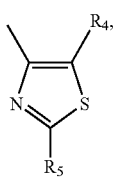 (A19)

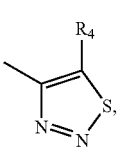 (A20)

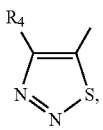 (A21)

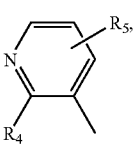 (A22)

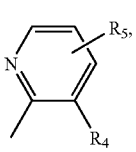 (A23)

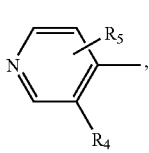 (A24)

-continued

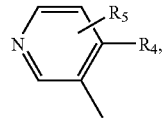 (A25)

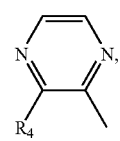 (A26)

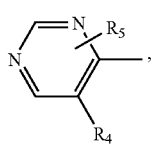 (A27)

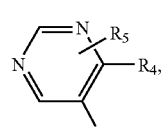 (A28)

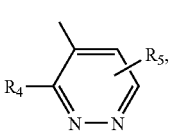 (A29)

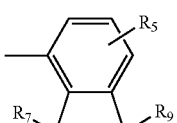 (A30)

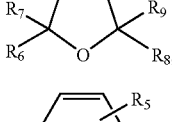 (A31)

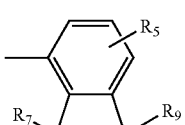 (A32)

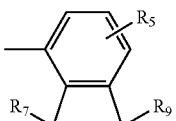 (A33)

and $R_4$ is $C_3$–$C_7$cycloalkyl, $C_4$–$C_7$cycloalkenyl, $C_5$–$C_7$cycloalkadienyl wherein the cycloalkyl group can be mono- to pentasubstituted by halogen, hydroxy, $C_1$–$C_4$alkyl, $C_1$–$C_4$alkoxy, $C_1$–$C_4$haloalkoxy, $C_2$–$C_4$alkenyl, $C_2$–$C_5$alkynyl, $C_1$–$C_4$haloalkyl; phenyl unsubstituted or substituted by halogen, nitro, cyano, CHO, $C_1$–$C_4$alkyl, $C_1$–$C_4$alkoxy, $C_1$–$C_4$haloalkoxy, $C_2$–$C_5$alkenyl, $C_2$–$C_5$alkynyl, $C_1$–$C_4$haloalkyl, COO$C_1$–$C_4$alkyl, $C_1$–$C_4$alkoxy-$C_1$–$C_4$alkyl, $C_1$–$C_4$alkyl-$C_1$–$C_4$alkoxy, $C_1$–$C_4$haloalkoxy-$C_1$–$C_4$alkyl, $C_1$–$C_4$haloalkyl-$C_1$–$C_4$alkoxy; thienyl, furyl, pyrrolyl, pyrazolyl, oxazolyl, thiazolyl, isoxazolyl, isothiazolyl, thiadiazolyl, imidazolyl, triazinyl, pyridyl, pyrazinyl, pyridazinyl or pyrimidinyl which are unsubstituted or substituted by halogen, $C_1$–$C_6$haloalkyl, $C_1$–$C_6$alkyl, $C_2$–$C_5$alkenyl, $C_2$–$C_5$alkynyl, nitro, cyano, hydroxy, CHO, $C_1$–$C_6$alkoxy, COO$C_1$–$C_6$alkyl, $C_1$–$C_4$alkoxy-$C_1$–$C_4$alkyl, $C_1$–$C_4$haloalkoxy-$C_1$–$C_4$alkyl or $C_1$–$C_6$haloalkoxy;

$R_5$ is hydrogen, cyano, nitro, halogen, $C_1$–$C_4$haloalkyl, $C_1$–$C_4$alkyl, $C_1$–$C_4$alkoxy-$C_1$–$C_4$alkyl, $C_1$–$C_4$haloalkoxy-$C_1$–$C_4$alkyl, $C_1$–$C_4$alkoxy or $C_1$–$C_4$haloalkoxy;

$R_6$, $R_7$, $R_8$, $R_9$ and $R_{10}$ are identical or different and are each independently of the others hydrogen, halogen, $C_1$–$C_4$haloalkyl, $C_1$–$C_4$alkyl, $C_2$–$C_5$alkenyl, $C_2$–$C_5$alkynyl, $C_1$–$C_4$alkoxy, $C_1$–$C_4$alkoxy-$C_1$–$C_4$alkyl, $C_1$–$C_6$haloalkoxy-$C_1$–$C_4$alkyl, $C_1$–$C_4$haloalkoxy or $C_3$–$C_7$cycloalkyl (subgroup AA).

Within the group AA of compounds of formula I those compounds are preferred wherein X is oxygen (subgroup AB).

Another group of compounds of formula I within the group M are those wherein X is sulfur (subgroup AC).

Within the subgroup AB are those compounds preferred wherein $R_1$ is $C_1$–$C_3$alkyl; $C_1$–$C_3$haloalkyl; $C_3$–$C_6$cycloalkyl unsubstituted or substituted by $C_1$–$C_3$alkyl, $C_1$–$C_3$haloalkyl or halogen;

$R_2$ is hydrogen, $C_1$–$C_4$alkyl or $C_1$–$C_4$haloalkyl;

$R_3$ is $C_1$–$C_4$alkyl, $C_1$–$C_3$haloalkyl or $C_1$–$C_3$alkoxy-$C_1$–$C_3$alkyl;

A is A1, A2, A3, A5, A8, A10, A13, A14, A17, A18, A20, A21, A22, A24, A25, A26, A27, A29, A31, A32 or A33;

$R_4$ is $C_5$–$C_7$cycloalkyl, unsubstituted or mono- to trisubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; $C_5$–$C_7$cycloalkenyl, unsubstituted or mono- to trisubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; $C_5$–$C_7$cyclodialkenyl, unsubstituted or mono- to disubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; thienyl, furyl, isoxazolyl, oxazolyl, thiadiazolyl, triazinyl, pyridyl, pyrimidinyl, pyrazinyl or pyridazinyl, which are unsubstituted or substituted by halogen, hydroxy, $C_1$–$C_4$alkyl, $C_1$–$C_4$haloalkyl, $C_1$–$C_4$alkoxy or $C_1$–$C_4$haloalkoxy; phenyl which is unsubstituted or substituted by halogen, $C_1$–$C_4$alkyl, $C_1$–$C_4$alkoxy, $C_1$–$C_4$haloalkyl or $C_1$–$C_4$haloalkoxy;

$R_5$ is hydrogen, halogen, $C_1$–$C_4$alkyl, $C_1$–$C_4$alkoxy, $C_1$–$C_4$haloalkyl or $C_1$–$C_4$haloalkoxy; and $R_6$, $R_7$, $R_8$, $R_9$ and $R_{10}$ are identical or different and are each independently of the others hydrogen, $C_1$–$C_4$alkyl, $C_1$–$C_4$alkoxy, $C_1$–$C_4$haloalkyl or $C_1C_4$haloalkoxy (subgroup AB1).

Within the subgroup AB1 are those compounds more preferred wherein

A is A1, A2, A3, A17, A20, A21, A24, A25, A26, A27, A31 or A33;

$R_1$ is $C_1$–$C_2$alkyl, $C_1$–$C_3$haloalkyl or cyclopropyl;

$R_2$ is hydrogen or $C_1$–$C_3$alkyl;

$R_3$ is $C_1$–$C_3$alkyl or $C_1$–$C_3$alkoxy-$C_1$–$C_3$alkyl;

$R_4$ is cyclohexyl, cyclohexenyl or cyclohexadienyl, which are unsubstituted or mono- to disubstituted by chloro, bromo, $C_1$–$C_2$alkyl, $C_1$–$C_2$haloalkyl or $C_1$–$C_2$haloalkoxy; thienyl, furyl, triazinyl, pyridyl, pyrazinyl, pyridazinyl or pyrimidinyl which are unsubstituted or substituted by halogen, $C_1$–$C_4$alkyl, $C_1$–$C_4$haloalkyl or $C_1$–$C_4$haloalkoxy;

$R_5$ is hydrogen, halogen, $C_1$–$C_3$alkyl, $C_1$–$C_3$haloalkyl, $C_1$–$C_3$alkoxy or $C_1$–$C_3$haloalkoxy; and $R_6$, $R_7$, $R_8$, $R_9$ and $R_{10}$ are identical or different and are each independently of the others hydrogen or $C_1$–$C_3$alkyl (subgroup AB2).

Preferred compounds within the subgroup AB2 are those compounds wherein $R_1$ is methyl, ethyl, $CFH_2$ or $CF_2H$;

$R_2$ is hydrogen;

$R_3$ is methyl or $CH_2OCH_3$;

A is A31 or A33; and $R_4$ is halophenyl, $C_5$–$C_7$cycloalkyl or halothienyl (subgroup AB3).

Within the subgroup AC are those compounds preferred wherein $R_1$ is $C_1$–$C_3$alkyl; $C_1$–$C_3$haloalkyl; $C_3$–$C_6$cycloalkyl unsubstituted or substituted by $C_1$–$C_3$alkyl, $C_1$–$C_3$haloalkyl or halogen;

$R_2$ is hydrogen, $C_1$–$C_4$alkyl or $C_1$–$C_4$haloalkyl;

$R_3$ is $C_1$–$C_4$alkyl, $C_1$–$C_3$haloalkyl or $C_1$–$C_3$alkoxy-$C_1$–$C_3$alkyl;

A is A1, A2, A3, A5, A8, A10, A13, A14, A17, A18, A20, A21, A22, A24, A25, A26, A27, A29, A31, A32 or A33;

$R_4$ is $C_5$–$C_7$cycloalkyl, unsubstituted or mono- to trisubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; $C_5$–$C_7$cycloalkenyl, unsubstituted or mono- to trisubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; $C_5$–$C_7$cyclodialkenyl, unsubstituted or mono- to disubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; thienyl, furyl, isoxazolyl, oxazolyl, thiadiazolyl, triazinyl, pyridyl, pyrimidinyl, pyrazinyl or pyridazinyl, which are unsubstituted or substituted by halogen, hydroxy, $C_1$–$C_4$alkyl, $C_1$–$C_4$haloalkyl, $C_1$–$C_4$alkoxy or $C_1$–$C_4$haloalkoxy; phenyl which is unsubstituted or substituted by halogen, $C_1$–$C_4$alkyl, $C_1$–$C_4$alkoxy, $C_1$–$C_4$haloalkyl or $C_1$–$C_4$haloalkoxy;

$R_5$ is hydrogen, halogen, $C_1$–$C_4$alkyl, $C_1$–$C_4$alkoxy, $C_1$–$C_4$haloalkyl or $C_1$–$C_4$haloalkoxy; and $R_6$, $R_7$, $R_8$, $R_9$ and $R_{10}$ are identical or different and are each independently of the others hydrogen, $C_1$–$C_4$alkyl, $C_1$–$C_4$alkoxy, $C_1$–$C_4$haloalkyl or $C_1$–$C_4$haloalkoxy (subgroup AC1).

Within the subgroup AC1 are those compounds more preferred wherein

A is A1, A2, A3, A17, A20, A21, A24, A25, A26, A27, A31 or A33;

$R_1$ is $C_1$–$C_2$alkyl, $C_1$–$C_3$haloalkyl or cyclopropyl;

$R_2$ is hydrogen or $C_1$–$C_3$alkyl;

$R_3$ is $C_1$–$C_3$alkyl or $C_1$–$C_3$alkoxy-$C_1$–$C_3$alkyl;

$R_4$ is cyclohexyl, cyclohexenyl or cyclohexadienyl, which are unsubstituted or mono- to disubstituted by chloro, bromo, $C_1$–$C_2$alkyl, $C_1$–$C_2$haloalkyl or $C_1$–$C_2$haloalkoxy; thienyl, furyl, triazinyl, pyridyl, pyrazinyl, pyridazinyl or pyrimidinyl which are unsubstituted or substituted by halogen, $C_1$–$C_4$alkyl, $C_1$–$C_4$haloalkyl or $C_1$–$C_4$haloalkoxy;

$R_5$ is hydrogen, halogen, $C_1$–$C_3$alkyl, $C_1$–$C_3$haloalkyl, $C_1$–$C_3$alkoxy or $C_1$–$C_3$haloalkoxy; and $R_6$, $R_7$, $R_8$, $R_9$ and $R_{10}$ are identical or different and are each independently of the others hydrogen or $C_1$–$C_3$alkyl (subgroup AC2).

The compounds according to formula I may be prepared according to the following reaction schemes.

A) Synthesis of the Pyrrole Carboxylic Acids:

Route 1 (Tosmic-route):

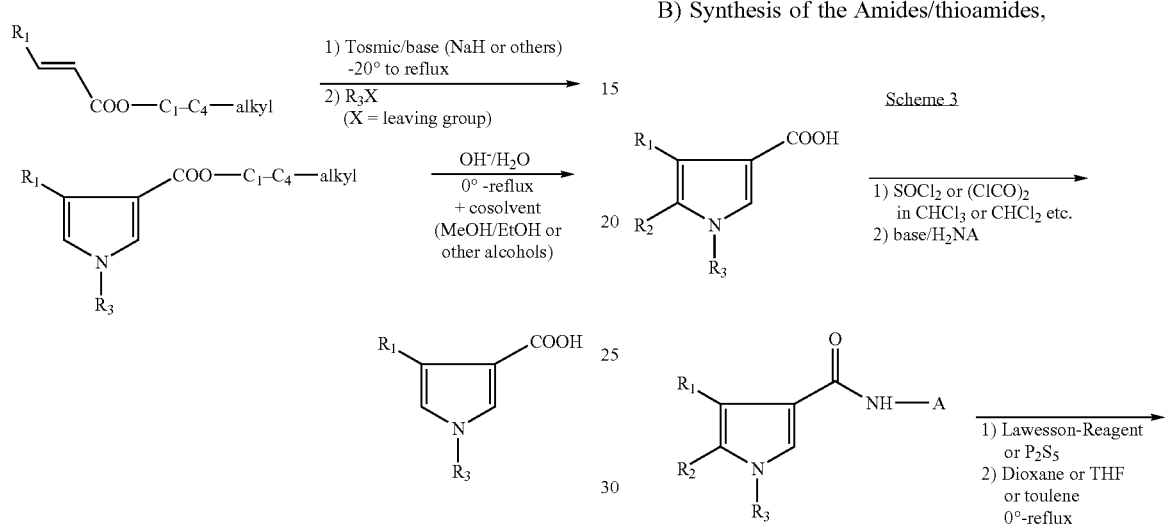

Route 2 ("acetoacetic acid"-route, see e.g. EP-326108; J.Am.Chem.Soc.70, 497(1948) or JP-07157466)

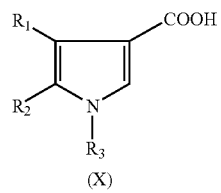

B) Synthesis of the Amides/thioamides,

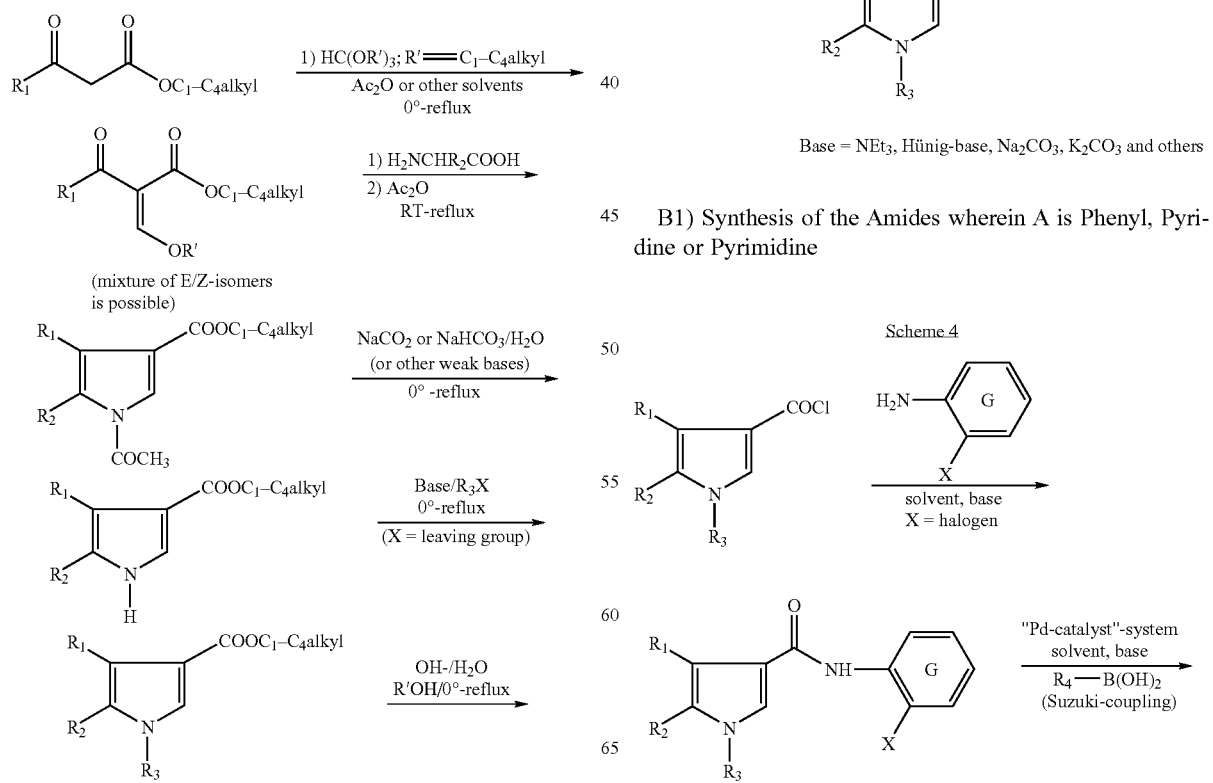

Base = NEt$_3$, Hünig-base, Na$_2$CO$_3$, K$_2$CO$_3$ and others

B1) Synthesis of the Amides wherein A is Phenyl, Pyridine or Pyrimidine

-continued

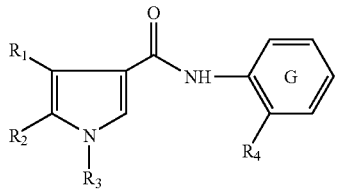

G = phenyl, pyridine, pyrimidine

The "in situ" prepared pyrazole carboxylic acid chloride reacts with an ortho-halosubstituted phenylamine in the presence of a solvent like toluene, benzene, xylene, hexane, cyclohexane, THF, chloroform or methylenechloride and in the presence of a base like sodium carbonate, sodium hydrogencarbonate, potassium carbonate, Hünig base, triethylamine or pyridine at a temperature between 0° C. and reflux temperature. The obtained pyrazolecarboxamide reacts with a boronic acid of the formula $R_4$—$B(OH)_2$ in the presence of a Pd-catalyst like $Pd(P(phenyl)_3)_4$, $Pd(P(phenyl)_3))_2Cl_2$, $PdCl_2dppb$, $Pd_2(dba)_3$, $Pd(OAc)_2$, $PdOAc_2/(o\text{-}tolyl)_3P$, $Pd(OAc)_2/dppf$, $Pd(PhCN)_2Cl_2/Ph_3As$, $Pd(CH_3CN)_2Cl_2$, $Pd_2(dba)_3/P(tert.butyl)_3$, $Pd(OAc)_2/P(tert.butyl)_2biphenyl$, $Pd(OAc)_2/TPPTS$, $Pd(OAc)_2/PCy_3$, $Pd(OAc)_2/P(O\text{-}i\text{-}Pr)_3$, $Pd(OAc)_2/2\text{-dimethylamino-2'-dicyclohexylphosphinobiphenyl}$, $Pd(OAc)_2/2\text{-dimethylamino-2'-ditert.butylphosphinobiphenyl}$, $Pd(OAc)_2/(o\text{-biphenyl})P(cyclohexyl)_2$ in a solvent like 1,2-dimethoxyethane/water, DMF, DMA, THF/water, dioxane/water, benzene, toluene, xylene and others and a base like sodium carbonate, sodium hydrogencarbonate, potassium carbonate, cesium carbonate, potassium phosphate, triethylamine, sodium hydroxide, sodium ethylate, sodium tert.butylate, silver oxide, barium carbonate, potassium fluoride or cesium fluoride at a temperature between 0° C. and reflux temperature.

B2) Synthesis of Pyrrolecarboxamides wherein $R_1$ is $CF_2H$

Scheme 5

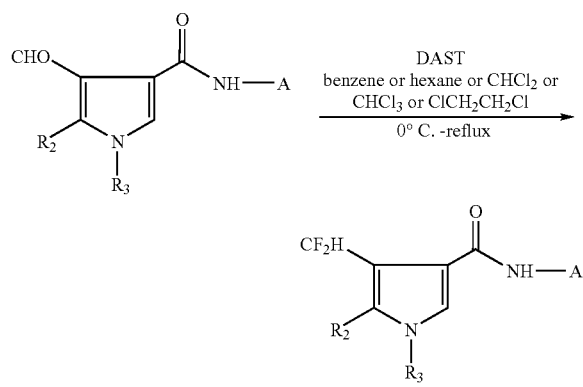

C) Synthesis of the ortho-substituted amines A—$NH_2$:

The compounds are either known from the literature or can be prepared by known methods. Literature for the synthesis of amine-intermediates and/or amines $A_i$—$NH_2$:

$A_1$—$NH_2$: Tetrahedron 1993, 49, 49–64 or EP-83975 or J.Org.Chem. 1995,60,292;

$A_2$—$NH_2$: EP-737682;

$A_3$—$NH_2$: J.Chem.Res.(S) 1978, 11, 428 or Chem.Scr. 1972, 2, 245;

$A_{17}$—$NH_2$: Org.Prep.Procedures Int. 1989, 21, 141;

$A_{21}$—$NH_2$: J.Chem.Soc.Perkin I 1981, 5, 1591;

$A_{25}$—$NH_2$: Tetrahedron 1993, 49, 49–64 or Heterocycles 1999, 51, 721;

$A_{26}$—$NH_2$: Synthesis 1996, 10, 1015 or Synthesis 1994, 9, 931;

$A_{27}$—$NH_2$: Liebigs Ann.Chemie 1977, 537–544 or J.Med.Chem. 1975, 18, 623;

$A_{31}$—$NH_2$: EP-315502;

$A_{32}$—$NH_2$: J.Pesticide Science 1993, 18, 245;

$A_{30}$—$NH_2$: J.Heterocyclic Chem. 1982, 19, 1285.

The invention relates also to the pyrrolecarboxylic acid of formula X, wherein $R_1$, $R_2$ and $R_3$ have the meaning as defined for formula I.

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic micro-organisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. Botrytis, Pyricularia, Helminthosporium, Fusarium, Septoria, Cercospora and Alternaria) and Basidiomycetes (e.g. Rhizoctonia, Hemileia, Puccinia). Additionally, they are also effective against the Ascomycetes classes (e.g. Venturia and Erysiphe, Podosphaera, Monilinia, Uncinula) and of the Oomycetes classes (e.g. Phytophthora, Pythium, Plasmopara). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines, hops, bananas and natural rubber plants, as well as ornamentals.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation. The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, of urace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2-[(2-trifluoromethyl)-pyrid-6-yloxymethyl]-3-methoxyacrylate or 2-[α{[(α-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenyl-amino-3,5-dihydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfonamide (IKF-916), N-(1-cyano-1,2-dimethylpropyl)-2-(2,4-dichlorophenoxy)-propionamide (AC 382042), or iprovalicarb (SZX 722).

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail. Temperatures are given in degrees Celsius. The following abbreviations are used: m.p.=melting point; b.p.=boiling point. "NMR" means nuclear magnetic resonance spectrum. MS stands for mass spectrum. "%" is percent by weight, unless corresponding concentrations are indicated in other units.

EXAMPLE 1

1,4-Dimethylpyrrole-3-carboxylic acid

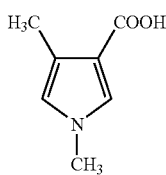

[cmpd. 11.1]

In a sulfonation flask 0.87 g (20 mmol) NaH (55%) are dissolved in 10 ml of absolute THF. Then a solution of 2.8 g (20 mmol) 4-methylpyrrole-3-carboxylic acid methylester in 400 ml THF is added dropwise. After stirring of the mixture for 10 minutes at room temperature, 1.2 ml (20 mmol) methyl iodide are added and stirring continued for 1 hour. After addition of 50 ml of a cold ca. 10% ammonium chloride solution the mixture is extracted twice with ethylacetate. After drying of the organic phase the solvent is removed in a water jet vacuum. The obtained crude N-methylated ester is dissolved in 10 ml ethanol and 20 ml of a 2N sodium hydroxide solution. The resulted mixture is stirred at 80–85° C. for 3 hours and then ethanol is removed in a water jet vacuum. After addition of 25 ml of water and extraction with ethylacetate the water phase is acidified with concentrated hydrochloric acid. After cooling the acid is separated by filtration. Yield after drying: 2.1 g of 1,4-dimethylpyrrole-3-carboxylic acid in form of a slightly brownish powder; m.p. 166–168° C.

EXAMPLE 2

1,4-Dimethylpyrrole-3-carboxylic acid [(4-fluorobiphenyl)-2-yl]amide

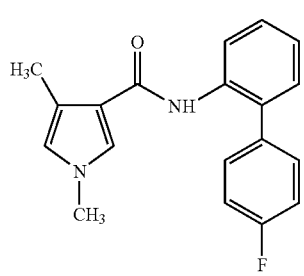

[cmpd. 1.25]

A solution of 0.49 g (3.5 mmol) 1,4-dimethylpyrrole-3-carboxylic acid and 0.49 g (3.8 mmol) oxalyl chloride in 20 ml of methylene chloride is stirred for 3 hours at room temperature in the presence of a catalytic amount of DMF. Then the acid chloride solution is slowly added to a solution of 0.65 g (3.5 mmol) 2-(4'-fluorophenyl)aniline, 0.43 g (4.2 mmol) triethylamine and 15 ml methylene chloride. The resulting mixture is then stirred for 16 hours at room temperature. After addition of ethylacetate, the organic phase is washed twice with water. Drying of the organic phase (Na$_2$SO$_4$) and removal of the solvent in a water jet vacuum yielded the raw material. Purification by column chromatography over silica gel (eluant:ethylacetate/hexane 1:1) gave 0.55 g 1,4-dimethylpyrrole-3-carboxylic acid [(4-fluorobiphenyl)-2-yl]amide in the form of slightly yellowish powder; m.p.: 147–149° C.

The following compounds are prepared in a similar way, using analogous methods.

TABLE 1

Compounds of the formula I, wherein A = A1 =

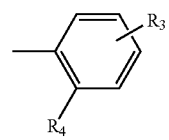

| Compd. No. | $R_1$ | $R_2$ | $R_3$ | $R_4$ | $R_5$ | X | Phys. data [m.p.] |
|---|---|---|---|---|---|---|---|
| 1.1 | CH$_3$ | H | CH$_3$ | HO-[1-methylcyclohexyl] | H | O | |
| 1.2 | CH$_3$ | H | CH$_3$ | Cl-[1-methylcyclohexyl] | H | O | |
| 1.3 | CH$_3$ | H | CH$_3$ | Br-[1-methyl-2-bromocyclohexyl] | H | O | |

TABLE 1-continued

Compounds of the formula I, wherein A = A1 =

| Compd. No. | R₁ | R₂ | R₃ | R₄ | R₅ | X | Phys. data [m.p.] |
|---|---|---|---|---|---|---|---|
| 1.4 | CH₃ | H | CH₃ | cyclohexenyl-Br | H | O | |
| 1.5 | CH₃ | H | CH₃ | cyclohexenyl | H | O | resin; MS, ¹H-NMR |
| 1.6 | CH₃ | H | CH₃ | cyclohexenyl | H | S | |
| 1.7 | CH₃ | H | CH₃ | cyclohexenyl-CH₃ | H | O | |
| 1.8 | CH₃ | H | CH₃ | cyclohexenyl-CH₂CH₃ | H | O | |
| 1.9 | CH₃ | H | CH₃ | cyclohexyl | H | O | resin; MS, ¹H-NMR |
| 1.10 | CH₃ | H | CH₃ | cyclohexyl-CH₃ | H | O | |
| 1.11 | CH₃ | H | CH₃ | cyclohexyl-CH₂CH₃ | H | O | |
| 1.12 | CH₃ | CH₃ | CH₃ | cyclohexyl-CH₂CH₃ | H | O | |
| 1.13 | CH₃ | H | CH₃ | cyclohexadienyl | H | O | |
| 1.14 | CH₃ | H | CH₃ | cyclohexadienyl-Cl | H | O | |
| 1.15 | CH₃ | H | CH₃ | phenyl-Cl | H | O | |

TABLE 1-continued

Compounds of the formula I, wherein A = A1 =

[structure with R3 and R4 substituents on phenyl ring]

| Compd. No. | $R_1$ | $R_2$ | $R_3$ | $R_4$ | $R_5$ | X | Phys. data [m.p.] |
|---|---|---|---|---|---|---|---|
| 1.16 | $CH_3$ | H | $CH_3$ | 2-F-phenyl | H | O | |
| 1.17 | $CH_3$ | H | $CH_3$ | 2-$CF_3$-phenyl | H | O | |
| 1.18 | $CH_3$ | H | $CH_3$ | 2-$OCF_3$-phenyl | H | O | |
| 1.19 | $CH_3$ | H | $CH_3$ | 3-Cl-phenyl | H | O | |
| 1.20 | $CH_3$ | H | $CH_3$ | 3-F-phenyl | H | O | |
| 1.21 | $CH_3$ | H | $CH_3$ | 3-$CF_3$-phenyl | H | O | |
| 1.22 | $CH_3$ | H | $CH_3$ | 3-$OCF_3$-phenyl | H | O | |
| 1.23 | $CH_3$ | H | $CH_3$ | 4-Cl-phenyl | H | O | 156–158 |
| 1.24 | $CH_3$ | H | $CH_3$ | 4-Cl-phenyl | H | S | |
| 1.25 | $CH_3$ | H | $CH_3$ | 4-F-phenyl | H | O | 148–149 |

TABLE 1-continued

Compounds of the formula I, wherein A = A1 =

| Compd. No. | R₁ | R₂ | R₃ | R₄ | R₅ | X | Phys. data [m.p.] |
|---|---|---|---|---|---|---|---|
| 1.26 | CH₃ | H | CH₃ | 4-F-phenyl | H | S | resin |
| 1.27 | CH₃ | H | CH₃ | 4-CF₃-phenyl | H | O | |
| 1.28 | CH₃ | H | CH₃ | 4-OCF₃-phenyl | H | O | |
| 1.29 | CH₃ | H | CH₃ | 3,4-diCl-phenyl | H | O | |
| 1.30 | CH₃ | H | CH₃ | 3,4-diF-phenyl | H | O | |
| 1.31 | CH₃ | H | CH₃ | 2-thienyl | H | O | |
| 1.32 | CH₃ | H | CH₃ | 5-Cl-2-thienyl | H | O | |
| 1.33 | CH₃ | H | CH₃ | 3-thienyl | H | O | |
| 1.34 | CH₃ | H | CH₃ | 2-Cl-3-thienyl | H | O | |
| 1.35 | CH₃ | H | CH₃ | 2-furyl | H | O | |
| 1.36 | CH₃ | H | CH₃ | 5-isoxazolyl | H | O | |
| 1.37 | CH₃ | H | CH₃ | 3-isoxazolyl | H | O | |

TABLE 1-continued
Compounds of the formula I, wherein A = A1 =
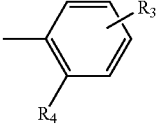
| Compd. No. | $R_1$ | $R_2$ | $R_3$ | $R_4$ | $R_5$ | X | Phys. data [m.p.] |
|---|---|---|---|---|---|---|---|
| 1.38 | $CH_3$ | H | $CH_3$ | 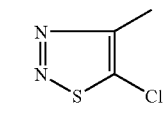 | H | O | |
| 1.39 | $CH_3$ | H | $CH_3$ | 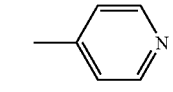 | H | O | |
| 1.40 | $CH_3$ | H | $CH_3$ | 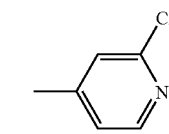 | H | O | |
| 1.41 | $CH_3$ | H | $CH_3$ | 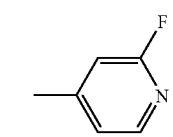 | H | O | |
| 1.42 | $CH_3$ | H | $CH_3$ | 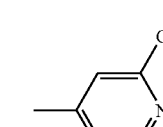 | H | O | |
| 1.43 | $CH_3$ | H | $CH_3$ | 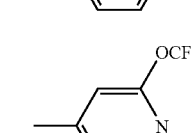 | H | O | |
| 1.44 | $CH_3$ | H | $CH_3$ | 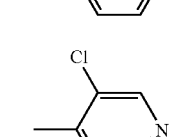 | H | O | |
| 1.45 | $CH_3$ | H | $CH_3$ | 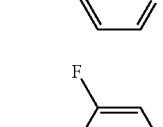 | H | O | |
| 1.46 | $CH_3$ | H | $CH_3$ | 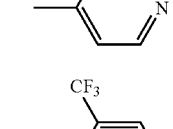 | H | O | 118–120 |
| 1.47 | $CH_3$ | H | $CH_3$ |  | H | O | |

TABLE 1-continued
Compounds of the formula I, wherein A = A1 =
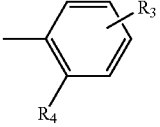
| Compd. No. | R₁ | R₂ | R₃ | R₄ | R₅ | X | Phys. data [m.p.] |
|---|---|---|---|---|---|---|---|
| 1.48 | CH₃ | H | CH₃ | 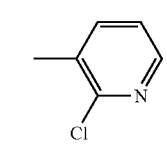 | H | O | |
| 1.49 | CH₃ | H | CH₃ | 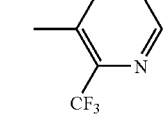 | H | O | |
| 1.50 | CH₃ | H | CH₃ | 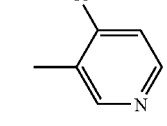 | H | O | |
| 1.51 | CH₃ | H | CH₃ | 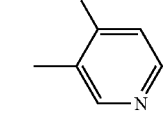 | H | O | |
| 1.52 | CH₃ | H | CH₃ | 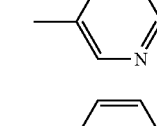 | H | O | |
| 1.53 | CH₃ | H | CH₃ | 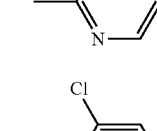 | H | O | |
| 1.54 | CH₃ | H | CH₃ | 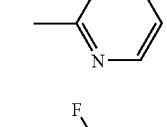 | H | O | |
| 1.55 | CH₃ | H | CH₃ | 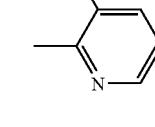 | H | O | |
| 1.56 | CH₃ | H | CH₃ | 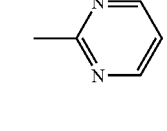 | H | O | |
| 1.57 | CH₃ | H | CH₃ |  | H | O | |

TABLE 1-continued
Compounds of the formula I, wherein A = A1 =
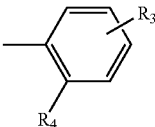
| Compd. No. | $R_1$ | $R_2$ | $R_3$ | $R_4$ | $R_5$ | X | Phys. data [m.p.] |
|---|---|---|---|---|---|---|---|
| 1.58 | $CH_3$ | H | $CH_3$ | 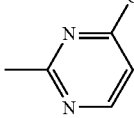 | H | O | |
| 1.59 | $CH_3$ | H | $CH_3$ | 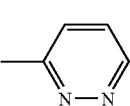 | H | O | |
| 1.60 | $CH_3$ | H | $CH_3$ | 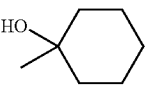 | H | O | |
| 1.61 | $CFH_2$ | H | $CH_3$ | 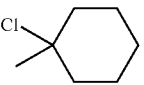 | H | O | |
| 1.62 | $CFH_2$ | H | $CH_3$ | 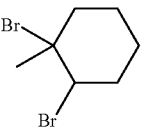 | H | O | |
| 1.63 | $CFH_2$ | H | $CH_3$ | 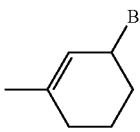 | H | O | |
| 1.64 | $CFH_2$ | H | $CH_3$ | 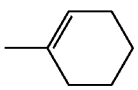 | H | O | |
| 1.65 | $CFH_2$ | H | $CH_3$ | 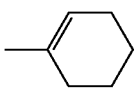 | H | O | |
| 1.66 | $CFH_2$ | H | $CH_3$ | 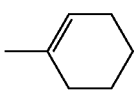 | H | S | |
| 1.67 | $CFH_2$ | H | $CH_3$ | 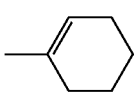 | H | O | |
| 1.68 | $CFH_2$ | H | $CH_3$ | 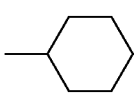 | H | O | |
| 1.69 | $CFH_2$ | H | $CH_3$ |  | H | O | |

TABLE 1-continued
Compounds of the formula I, wherein A = A1 =
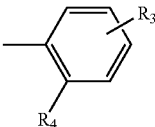
| Compd. No. | R₁ | R₂ | R₃ | R₄ | R₅ | X | Phys. data [m.p.] |
|---|---|---|---|---|---|---|---|
| 1.70 | CFH₂ | H | CH₃ | 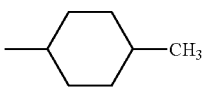 | H | O | |
| 1.71 | CFH₂ | H | CH₃ | 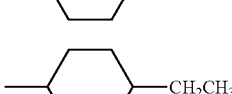 | H | O | |
| 1.72 | CFH₂ | CH₃ | CH₃ | 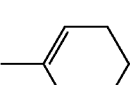 | H | O | |
| 1.73 | CFH₂ | H | CH₃ | 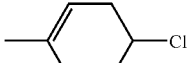 | H | O | |
| 1.74 | CFH₂ | H | CH₃ | 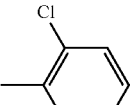 | H | O | |
| 1.75 | CFH₂ | H | CH₃ | 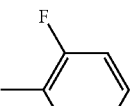 | H | O | |
| 1.76 | CFH₂ | H | CH₃ | 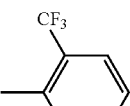 | H | O | |
| 1.77 | CFH₂ | H | CH₃ | 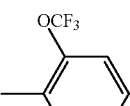 | H | O | |
| 1.78 | CFH₂ | H | CH₃ | 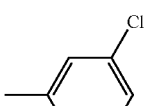 | H | O | |
| 1.79 | CFH₂ | H | CH₃ | 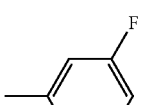 | H | O | |
| 1.80 | CFH₂ | H | CH₃ |  | H | O | |

TABLE 1-continued

Compounds of the formula I, wherein A = A1 =

| Compd. No. | $R_1$ | $R_2$ | $R_3$ | $R_4$ | $R_5$ | X | Phys. data [m.p.] |
|---|---|---|---|---|---|---|---|
| 1.81 | $CFH_2$ | H | $CH_3$ | 3-$CF_3$-phenyl | H | O | |
| 1.82 | $CFH_2$ | H | $CH_3$ | 3-$OCF_3$-phenyl | H | O | |
| 1.83 | $CFH_2$ | H | $CH_3$ | 4-Cl-phenyl | H | O | |
| 1.84 | $CFH_2$ | H | $CH_3$ | 4-Cl-phenyl | H | S | |
| 1.85 | $CFH_2$ | H | $CH_3$ | 4-F-phenyl | H | O | |
| 1.86 | $CFH_2$ | H | $CH_3$ | 4-F-phenyl | H | S | |
| 1.87 | $CFH_2$ | H | $CH_3$ | 4-$CF_3$-phenyl | H | O | |
| 1.88 | $CFH_2$ | H | $CH_3$ | 4-$OCF_3$-phenyl | H | O | |
| 1.89 | $CFH_2$ | H | $CH_3$ | 3,4-diCl-phenyl | H | O | |
| 1.90 | $CFH_2$ | H | $CH_3$ | 3,4-diF-phenyl | H | O | |
| 1.91 | $CFH_2$ | H | $CH_3$ | 2-thienyl | H | O | |
| 1.92 | $CFH_2$ | H | $CH_3$ | 5-Cl-2-thienyl | H | O | |

TABLE 1-continued

Compounds of the formula I, wherein A = A1 =

| Compd. No. | R₁ | R₂ | R₃ | R₄ | R₅ | X | Phys. data [m.p.] |
|---|---|---|---|---|---|---|---|
| 1.93 | CFH₂ | H | CH₃ | 3-methylthiophen-2-yl | H | O | |
| 1.94 | CFH₂ | H | CH₃ | 2-chloro-3-methylthiophen-4-yl | H | O | |
| 1.95 | CFH₂ | H | CH₃ | 5-methylfuran-2-yl | H | O | |
| 1.96 | CFH₂ | H | CH₃ | 5-methylisoxazol-3-yl | H | O | |
| 1.97 | CFH₂ | H | CH₃ | 4-methylisoxazol-3-yl | H | O | |
| 1.98 | CFH₂ | H | CH₃ | 5-methyloxazol-2-yl | H | O | |
| 1.99 | CFH₂ | H | CH₃ | 5-chloro-4-methyl-1,2,3-thiadiazol-... | H | O | |
| 1.100 | CFH₂ | H | CH₃ | 4-methylpyridin-2-yl | H | O | |
| 1.101 | CFH₂ | H | CH₃ | 2-chloro-4-methylpyridin-5-yl | H | O | |
| 1.102 | CFH₂ | H | CH₃ | 2-chloro-4-methylpyridin-5-yl | H | S | |
| 1.103 | CFH₂ | H | CH₃ | 2-fluoro-4-methylpyridin-5-yl | H | O | |

TABLE 1-continued
Compounds of the formula I, wherein A = A1 =
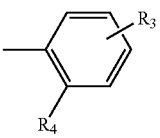
| Compd. No. | $R_1$ | $R_2$ | $R_3$ | $R_4$ | $R_5$ | X | Phys. data [m.p.] |
|---|---|---|---|---|---|---|---|
| 1.104 | $CFH_2$ | H | $CH_3$ | 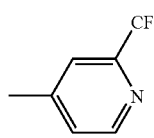 | H | O | |
| 1.105 | $CFH_2$ | H | $CH_3$ | 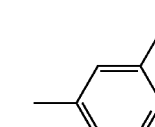 | H | O | |
| 1.106 | $CFH_2$ | H | $CH_3$ | 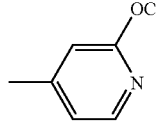 | H | O | |
| 1.107 | $CFH_2$ | H | $CH_3$ | 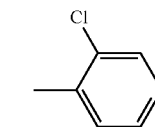 | H | O | |
| 1.108 | $CFH_2$ | H | $CH_3$ | 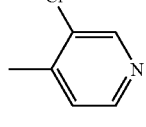 | H | O | |
| 1.109 | $CFH_2$ | H | $CH_3$ | 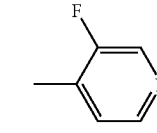 | H | O | |
| 1.110 | $CFH_2$ | H | $CH_3$ | 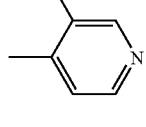 | H | O | |
| 1.111 | $CFH_2$ | H | $CH_3$ | 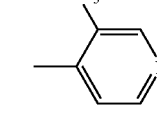 | H | O | |
| 1.112 | $CFH_2$ | H | $CH_3$ | 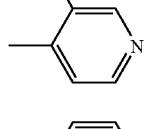 | H | O | |

TABLE 1-continued

Compounds of the formula I, wherein A = A1 =

| Compd. No. | $R_1$ | $R_2$ | $R_3$ | $R_4$ | $R_5$ | X | Phys. data [m.p.] |
|---|---|---|---|---|---|---|---|
| 1.113 | $CFH_2$ | H | $CH_3$ | 4-fluoropyridin-3-yl | H | O | |
| 1.114 | $CFH_2$ | H | $CH_3$ | 6-chloropyridin-3-yl | H | O | |
| 1.115 | $CFH_2$ | H | $CH_3$ | pyridin-2-yl | H | O | |
| 1.116 | $CFH_2$ | H | $CH_3$ | 3-chloropyridin-2-yl | H | O | |
| 1.117 | $CFH_2$ | H | $CH_3$ | 3-fluoropyridin-2-yl | H | O | |
| 1.118 | $CFH_2$ | H | $CH_3$ | pyrimidin-2-yl | H | O | |
| 1.119 | $CFH_2$ | H | $CH_3$ | 4-chloropyrimidin-2-yl | H | O | |
| 1.120 | $CFH_2$ | H | $CH_3$ | pyridazin-3-yl | H | O | |
| 1.121 | $CFH_2$ | H | $CH_3$ | pyridazin-3-yl | H | O | |
| 1.122 | $CF_2H$ | H | $CH_3$ | 1-hydroxy-1-methylcyclohexyl | H | O | |
| 1.123 | $CF_2H$ | H | $CH_3$ | 1-chloro-1-methylcyclohexyl | H | O | |

TABLE 1-continued
Compounds of the formula I, wherein A = A1 =
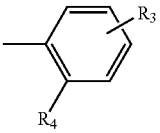
| Compd. No. | $R_1$ | $R_2$ | $R_3$ | $R_4$ | $R_5$ | X | Phys. data [m.p.] |
|---|---|---|---|---|---|---|---|
| 1.124 | $CF_2H$ | H | $CH_3$ | 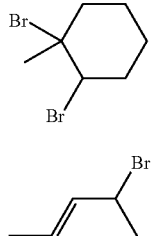 | H | O | |
| 1.125 | $CF_2H$ | H | $CH_3$ | 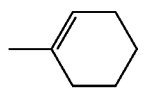 | H | O | |
| 1.126 | $CF_2H$ | H | $CH_3$ | 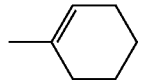 | H | O | |
| 1.127 | $CF_2H$ | H | $CH_3$ | 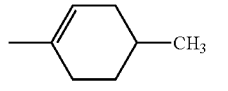 | H | S | |
| 1.128 | $CF_2H$ | H | $CH_3$ | 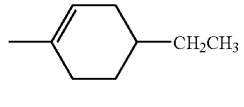 | H | O | |
| 1.129 | $CF_2H$ | H | $CH_3$ | 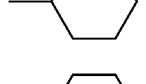 | H | O | |
| 1.130 | $CF_2H$ | H | $CH_3$ | 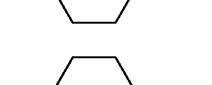 | H | O | |
| 1.131 | $CF_2H$ | H | $CH_3$ |  | H | O | |
| 1.132 | $CF_2H$ | H | $CH_3$ | 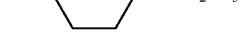 | H | O | |
| 1.133 | $CF_2H$ | $CH_3$ | $CH_3$ | 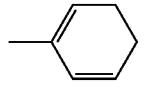 | H | O | |
| 1.134 | $CF_2H$ | H | $CH_3$ | 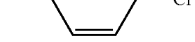 | H | O | |
| 1.135 | $CF_2H$ | H | $CH_3$ |  | H | O | |

TABLE 1-continued
Compounds of the formula I, wherein A = A1 =
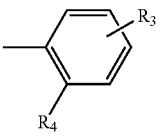
| Compd. No. | R₁ | R₂ | R₃ | R₄ | R₅ | X | Phys. data [m.p.] |
|---|---|---|---|---|---|---|---|
| 1.136 | CF₂H | H | CH₃ | 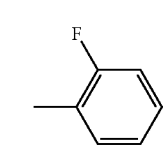 | H | O | |
| 1.137 | CF₂H | H | CH₃ | 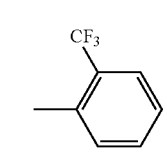 | H | O | |
| 1.138 | CF₂H | H | CH₃ | 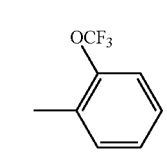 | H | O | |
| 1.139 | CF₂H | H | CH₃ | 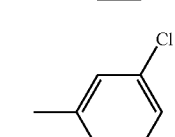 | H | O | |
| 1.140 | CF₂H | H | CH₃ | 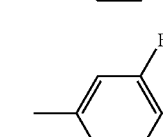 | H | O | |
| 1.141 | CF₂H | H | CH₃ | 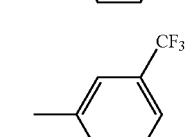 | H | O | |
| 1.142 | CF₂H | H | CH₃ | 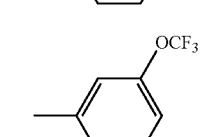 | H | O | |
| 1.143 | CF₂H | H | CH₃ | 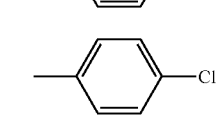 | H | O | |
| 1.144 | CF₂H | H | CH₃ | 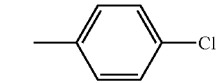 | H | O | resin |
| 1.145 | CF₂H | H | CH₃ | 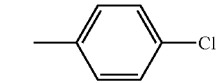 | H | S | |

TABLE 1-continued

Compounds of the formula I, wherein A = A1 =

| Compd. No. | $R_1$ | $R_2$ | $R_3$ | $R_4$ | $R_5$ | X | Phys. data [m.p.] |
|---|---|---|---|---|---|---|---|
| 1.146 | $CF_2H$ | H | $CH_3$ | 4-F-phenyl | H | O | |
| 1.147 | $CF_2H$ | H | $CH_3$ | 4-F-phenyl | H | S | |
| 1.148 | $CF_2H$ | H | $CH_3$ | 4-$CF_3$-phenyl | H | O | |
| 1.149 | $CF_2H$ | H | $CH_3$ | 4-$OCF_3$-phenyl | H | O | |
| 1.150 | $CF_2H$ | H | $CH_3$ | 3,4-diCl-phenyl | H | O | |
| 1.151 | $CF_2H$ | H | $CH_3$ | 3,4-diF-phenyl | H | O | |
| 1.152 | $CF_2H$ | H | $CH_3$ | 2-thienyl | H | O | |
| 1.153 | $CF_2H$ | H | $CH_3$ | 5-Cl-2-thienyl | H | O | resin, MS |
| 1.154 | $CF_2H$ | H | $CH_3$ | 3-thienyl | H | O | |
| 1.155 | $CF_2H$ | H | $CH_3$ | 2-Cl-3-methyl-thienyl | H | O | |
| 1.156 | $CF_2H$ | H | $CH_3$ | 2-furyl | H | O | |
| 1.157 | $CF_2H$ | H | $CH_3$ | 5-isoxazolyl | H | O | |

TABLE 1-continued
Compounds of the formula I, wherein A = A1 =
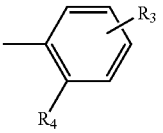
| Compd. No. | $R_1$ | $R_2$ | $R_3$ | $R_4$ | $R_5$ | X | Phys. data [m.p.] |
|---|---|---|---|---|---|---|---|
| 1.158 | $CF_2H$ | H | $CH_3$ | 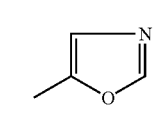 | H | O | |
| 1.159 | $CF_2H_2$ | H | $CH_3$ | 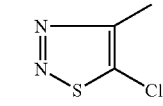 | H | O | |
| 1.160 | $CF_2H$ | H | $CH_3$ | 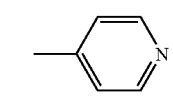 | H | O | |
| 1.161 | $CF_2H$ | H | $CH_3$ | 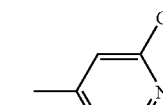 | H | O | |
| 1.162 | $CF_2H$ | H | $CH_3$ | 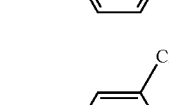 | H | O | |
| 1.163 | $CF_2H$ | H | $CH_3$ | 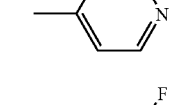 | H | S | |
| 1.164 | $CF_2H$ | H | $CH_3$ | 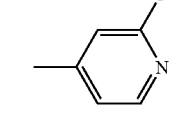 | H | O | |
| 1.165 | $CF_2H$ | H | $CH_3$ | 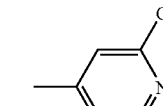 | H | O | |
| 1.166 | $CF_2H$ | H | $CH_3$ | 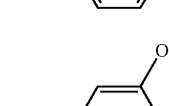 | H | O | |
| 1.167 | $CF_2H$ | H | $CH_3$ |  | H | O | |

TABLE 1-continued

Compounds of the formula I, wherein A = A1 =

(structure: phenyl ring with R3 and R4 substituents)

| Compd. No. | $R_1$ | $R_2$ | $R_3$ | $R_4$ | $R_5$ | X | Phys. data [m.p.] |
|---|---|---|---|---|---|---|---|
| 1.168 | $CF_2H$ | H | $CH_3$ | 3-fluoro-pyridin-4-yl | H | O | |
| 1.169 | $CF_2H$ | H | $CH_3$ | 3-trifluoromethyl-pyridin-4-yl | H | O | |
| 1.170 | $CF_2H$ | H | $CH_3$ | pyridin-3-yl | H | O | |
| 1.171 | $CF_2H$ | H | $CH_3$ | 2-chloro-3-methyl-pyridin-3-yl | H | O | |
| 1.172 | $CF_2H$ | H | $CH_3$ | 2-trifluoromethyl-pyridin-3-yl | H | O | |
| 1.173 | $CF_2H$ | H | $CH_3$ | 4-chloro-pyridin-3-yl | H | O | |
| 1.174 | $CF_2H$ | H | $CH_3$ | 4-fluoro-pyridin-3-yl | H | O | |
| 1.175 | $CF_2H$ | H | $CH_3$ | 6-chloro-pyridin-3-yl | H | O | |
| 1.176 | $CF_2H$ | H | $CH_3$ | pyridin-2-yl | H | O | |
| 1.177 | $CF_2H$ | H | $CH_3$ | 3-chloro-pyridin-2-yl | H | O | |

TABLE 1-continued
Compounds of the formula I, wherein A = A1 =
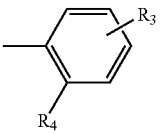
| Compd. No. | $R_1$ | $R_2$ | $R_3$ | $R_4$ | $R_5$ | X | Phys. data [m.p.] |
|---|---|---|---|---|---|---|---|
| 1.178 | $CF_2H$ | H | $CH_3$ | 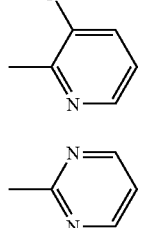 | H | O | |
| 1.179 | $CF_2H$ | H | $CH_3$ | 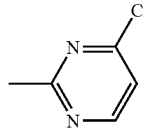 | H | O | |
| 1.180 | $CF_2H$ | H | $CH_3$ | 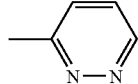 | H | O | |
| 1.181 | $CF_2H$ | H | $CH_3$ | 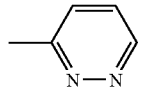 | H | O | |
| 1.182 | $CF_2H$ | H | $CH_3$ | 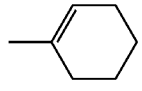 | H | O | |
| 1.183 | $CF_2CF_3$ | H | $CH_3$ | 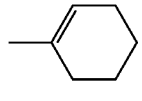 | H | O | 113–114 |
| 1.184 | $CF_2CF_3$ | H | $CH_3$ | 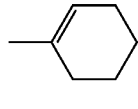 | H | S | |
| 1.185 | $CF_2CF_3$ | H | $CH_3$ | 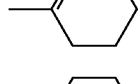 —$CH_3$ | H | O | |
| 1.186 | $CF_2CF_3$ | H | $CH_3$ | 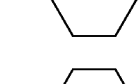 —$CH_2CH_3$ | H | O | |
| 1.187 | $CF_2CF_3$ | H | $CH_3$ | 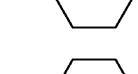 | H | O | 120–121 |
| 1.188 | $CF_2CF_3$ | H | $CH_3$ | 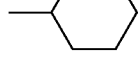 —$CH_3$ | H | O | |
| 1.189 | $CF_2CF_3$ | H | $CH_3$ |  —$CH_2CH_3$ | H | O | |

TABLE 1-continued

Compounds of the formula I, wherein A = A1 =

| Compd. No. | R₁ | R₂ | R₃ | R₄ | R₅ | X | Phys. data [m.p.] |
|---|---|---|---|---|---|---|---|
| 1.190 | CF₂CF₃ | H | CH₃ | 4-Cl-phenyl | H | O | 148–150 |
| 1.191 | CF₂CF₃ | H | CH₃ | 4-Cl-phenyl | H | S | |
| 1.192 | CF₂CF₃ | H | CH₃ | 4-F-phenyl | H | O | 134–136 |
| 1.193 | CF₂CF₃ | H | CH₃ | 4-F-phenyl | H | S | |
| 1.194 | CF₂CF₃ | H | CH₃ | 4-CF₃-phenyl | H | O | |
| 1.195 | CF₂CF₃ | H | CH₃ | 4-OCF₃-phenyl | H | O | |
| 1.196 | CF₂CF₃ | H | CH₃ | 3,4-di-Cl-phenyl | H | O | |
| 1.197 | CF₂CF₃ | H | CH₃ | 3,4-di-F-phenyl | H | O | |
| 1.198 | Δ | H | CH₃ | 1-hydroxy-1-methyl-cyclohexyl | H | O | |
| 1.199 | Δ | H | CH₃ | 1-chloro-1-methyl-cyclohexyl | H | O | |
| 1.200 | Δ | H | CH₃ | 1,2-dibromo-1-methyl-cyclohexyl | H | O | |
| 1.201 | Δ | H | CH₃ | 3-bromo-1-methyl-cyclohexenyl | H | O | |

TABLE 1-continued
Compounds of the formula I, wherein A = A1 =
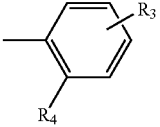
| Compd. No. | R₁ | R₂ | R₃ | R₄ | R₅ | X | Phys. data [m.p.] |
|---|---|---|---|---|---|---|---|
| 1.202 | Δ | H | CH₃ | 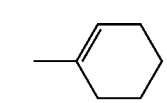 | H | O | |
| 1.203 | Δ | H | CH₃ |  | H | S | |
| 1.204 | Δ | H | CH₃ | 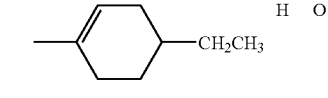 | H | O | |
| 1.205 | Δ | H | CH₃ | 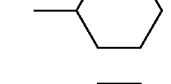 | H | O | |
| 1.206 | Δ | H | CH₃ | 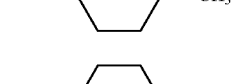 | H | O | resin; MS, ¹H-NMR |
| 1.207 | Δ | H | CH₃ | 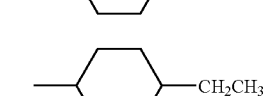 | H | O | |
| 1.208 | Δ | H | CH₃ | 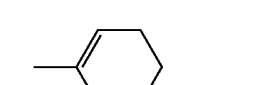 | H | O | |
| 1.209 | Δ | CH₃ | CH₃ | 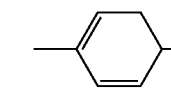 | H | O | |
| 1.210 | Δ | H | CH₃ | 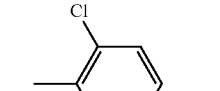 | H | O | |
| 1.211 | Δ | H | CH₃ | 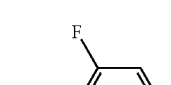 | H | O | |
| 1.212 | Δ | H | CH₃ | 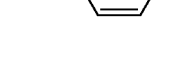 | H | O | |
| 1.213 | Δ | H | CH₃ |  | H | O | |

TABLE 1-continued

Compounds of the formula I, wherein A = A1 =

| Compd. No. | R₁ | R₂ | R₃ | R₄ | R₅ | X | Phys. data [m.p.] |
|---|---|---|---|---|---|---|---|
| 1.214 | Δ | H | CH₃ | 2-CF₃-phenyl | H | O | |
| 1.215 | Δ | H | CH₃ | 2-OCF₃-phenyl | H | O | |
| 1.216 | Δ | H | CH₃ | 3-Cl-phenyl | H | O | |
| 1.217 | Δ | H | CH₃ | 3-F-phenyl | H | O | |
| 1.218 | Δ | H | CH₃ | 3-CF₃-phenyl | H | O | |
| 1.219 | Δ | H | CH₃ | 3-OCF₃-phenyl | H | O | |
| 1.220 | Δ | H | CH₃ | 4-Cl-phenyl | H | O | |
| 1.221 | Δ | H | CH₃ | 4-Cl-phenyl | H | S | |
| 1.222 | Δ | H | CH₃ | 4-F-phenyl | H | O | |
| 1.223 | Δ | H | CH₃ | 4-F-phenyl | H | S | |
| 1.224 | Δ | H | CH₃ | 4-CF₃-phenyl | H | O | |

TABLE 1-continued

Compounds of the formula I, wherein A = A1 =

| Compd. No. | R₁ | R₂ | R₃ | R₄ | R₅ | X | Phys. data [m.p.] |
|---|---|---|---|---|---|---|---|
| 1.225 | Δ | H | CH₃ | -C₆H₄-OCF₃ | H | O | |
| 1.226 | Δ | H | CH₃ | 3,4-dichlorophenyl | H | O | |
| 1.227 | Δ | H | CH₃ | 3,4-difluorophenyl | H | O | |
| 1.228 | Δ | H | CH₃ | 2-thienyl | H | O | |
| 1.229 | Δ | H | CH₃ | 5-chloro-2-thienyl | H | O | |
| 1.230 | Δ | H | CH₃ | 3-thienyl | H | O | |
| 1.231 | Δ | H | CH₃ | 2-chloro-3-thienyl | H | O | |
| 1.232 | Δ | H | CH₃ | 2-furyl | H | O | |
| 1.233 | Δ | H | CH₃ | 5-isoxazolyl | H | O | |
| 1.234 | Δ | H | CH₃ | 4-isoxazolyl | H | O | |
| 1.235 | Δ | H | CH₃ | 5-oxazolyl | H | O | |
| 1.236 | Δ | H | CH₃ | 5-chloro-1,2,3-thiadiazol-4-yl | H | O | |

TABLE 1-continued

Compounds of the formula I, wherein A = A1 =

| Compd. No. | R₁ | R₂ | R₃ | R₄ | R₅ | X | Phys. data [m.p.] |
|---|---|---|---|---|---|---|---|
| 1.237 | Δ | H | CH₃ | 4-pyridyl | H | O | |
| 1.238 | Δ | H | CH₃ | 2-Cl-4-pyridyl | H | O | |
| 1.239 | Δ | H | CH₃ | 2-Cl-4-pyridyl | H | S | |
| 1.240 | Δ | H | CH₃ | 2-F-4-pyridyl | H | O | |
| 1.241 | Δ | H | CH₃ | 2-CF₃-4-pyridyl | H | O | |
| 1.242 | Δ | H | CH₃ | 2-OCF₃-4-pyridyl | H | O | |
| 1.243 | Δ | H | CH₃ | 3-Cl-4-pyridyl | H | O | |
| 1.244 | Δ | H | CH₃ | 3-F-4-pyridyl | H | O | 105–107 |
| 1.245 | Δ | H | CH₃ | 3-CF₃-4-pyridyl | H | O | |
| 1.246 | Δ | H | CH₃ | 3-pyridyl | H | O | |

TABLE 1-continued
Compounds of the formula I, wherein A = A1 =
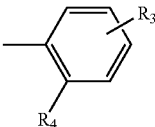
| Compd. No. | R₁ | R₂ | R₃ | R₄ | R₅ | X | Phys. data [m.p.] |
|---|---|---|---|---|---|---|---|
| 1.247 | Δ | H | CH₃ | 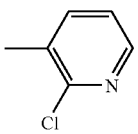 | H | O | |
| 1.248 | Δ | H | CH₃ | 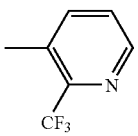 | H | O | |
| 1.249 | Δ | H | CH₃ | 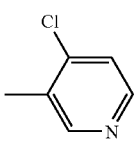 | H | O | |
| 1.250 | Δ | H | CH₃ | 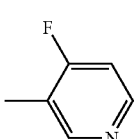 | H | O | |
| 1.251 | Δ | H | CH₃ | 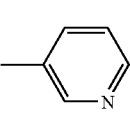 | H | O | |
| 1.252 | Δ | H | CH₃ | 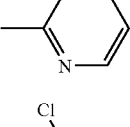 | H | O | |
| 1.253 | Δ | H | CH₃ | 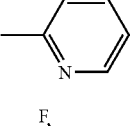 | H | O | |
| 1.254 | Δ | H | CH₃ | 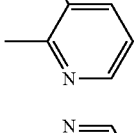 | H | O | |
| 1.255 | Δ | H | CH₃ | 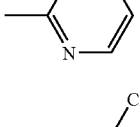 | H | O | |
| 1.256 | Δ | H | CH₃ |  | H | O | |

TABLE 1-continued

Compounds of the formula I, wherein A = A1 =

| Compd. No. | R₁ | R₂ | R₃ | R₄ | R₅ | X | Phys. data [m.p.] |
|---|---|---|---|---|---|---|---|
| 1.257 | Δ | H | CH₃ | 3-methylpyridazin-6-yl | H | O | |
| 1.258 | Δ | H | CH₃ | 3-methylpyridazin-6-yl | H | O | |
| 1.259 | CH₃ | H | CH₃ | 2-chloro-4-methylpyridin-5-yl | H | S | |
| 1.260 | CH₂CH₃ | H | CH₃ | 4-chlorophenyl | H | O | 152–153 |
| 1.261 | CH₂CH₃ | H | CH₃ | 4-fluorophenyl | H | O | 120–121 |
| 1.262 | CH₂CH₃ | H | CH₃ | cyclohexyl | H | O | |
| 1.263 | CH₂CH₃ | H | CH₃ | 4-methylcyclohexyl | H | O | |
| 1.264 | CH₂CH₃ | H | CH₃ | cycloheptyl | H | O | |
| 1.265 | CH₂CH₃ | H | CH₂CH₃ | 4-chlorophenyl | H | O | 97–98 |
| 1.266 | CH₂CH₃ | H | CH₂CH₃ | 4-fluorophenyl | H | O | 95–96 |
| 1.267 | CH₂CH₃ | H | CH₂CH₃ | cyclooctyl | H | O | |
| 1.268 | (CH₃)₂CH | H | CH₃ | 4-chlorophenyl | H | O | 102–103 |

TABLE 1-continued

Compounds of the formula I, wherein A = A1 =

| Compd. No. | $R_1$ | $R_2$ | $R_3$ | $R_4$ | $R_5$ | X | Phys. data [m.p.] |
|---|---|---|---|---|---|---|---|
| 1.269 | $(CH_3)_2CH$ | H | $CH_3$ | 4-F-phenyl | H | O | 99–100 |
| 1.270 | $(CH_3)_2CH$ | H | $CH_3$ | 4-CH$_3$-cyclohexyl | H | O |  |
| 1.271 | $(CH_3)_2CH$ | H | $CH_2CH_3$ | 4-Cl-phenyl | H | O | 116–117 |
| 1.272 | $(CH_3)_2CH$ | H | $CH_2CH_3$ | 4-F-phenyl | H | O | 93–94 |

TABLE 2

Compounds of the formula I, wherein A = A2 =

| Compd. No. | $R_1$ | $R_2$ | $R_3$ | $R_4$ | $R_5$ | X | Phys. data [m.p.] |
|---|---|---|---|---|---|---|---|
| 2.1 | $CH_3$ | H | $CH_3$ | 1-HO-cyclohexyl | H | O |  |
| 2.2 | $CH_3$ | H | $CH_3$ | 1-Cl-cyclohexyl | H | O |  |
| 2.3 | $CH_3$ | H | $CH_3$ | 1,2-diBr-cyclohexyl | H | O |  |
| 2.4 | $CH_3$ | H | $CH_3$ | 6-Br-cyclohex-1-enyl | H | O |  |
| 2.5 | $CH_3$ | H | $CH_3$ | cyclohex-1-enyl | H | O |  |

TABLE 2-continued

Compounds of the formula I, wherein A = A2 =

| Compd. No. | $R_1$ | $R_2$ | $R_3$ | $R_4$ | $R_5$ | X | Phys. data [m.p.] |
|---|---|---|---|---|---|---|---|
| 2.6 | $CH_3$ | H | $CH_3$ | cyclohexenyl | H | S | |
| 2.7 | $CH_3$ | H | $CH_3$ | 4-methylcyclohexenyl | H | O | |
| 2.8 | $CH_3$ | H | $CH_3$ | 4-ethylcyclohexenyl | H | O | |
| 2.9 | $CH_3$ | H | $CH_3$ | cyclohexyl | H | O | |
| 2.10 | $CH_3$ | H | $CH_3$ | 4-methylcyclohexyl | H | O | |
| 2.11 | $CH_3$ | H | $CH_3$ | 4-ethylcyclohexyl | H | O | |
| 2.12 | $CH_3$ | $CH_3$ | $CH_3$ | 4-ethylcyclohexyl | H | O | |
| 2.13 | $CH_3$ | H | $CH_3$ | phenyl | H | O | |
| 2.14 | $CH_3$ | H | $CH_3$ | 4-chlorophenyl | H | O | |
| 2.15 | $CH_3$ | H | $CH_3$ | 2-chlorophenyl | H | O | |
| 2.16 | $CH_3$ | H | $CH_3$ | 2-fluorophenyl | H | O | |
| 2.17 | $CH_3$ | H | $CH_3$ | 2-trifluoromethylphenyl | H | O | |

TABLE 2-continued

Compounds of the formula I, wherein A = A2 =

| Compd. No. | R₁ | R₂ | R₃ | R₄ | R₅ | X | Phys. data [m.p.] |
|---|---|---|---|---|---|---|---|
| 2.18 | CH₃ | H | CH₃ | 2-OCF₃-phenyl | H | O | |
| 2.19 | CH₃ | H | CH₃ | 3-Cl-phenyl | H | O | |
| 2.20 | CH₃ | H | CH₃ | 3-F-phenyl | H | O | |
| 2.21 | CH₃ | H | CH₃ | 3-CF₃-phenyl | H | O | |
| 2.22 | CH₃ | H | CH₃ | 3-OCF₃-phenyl | H | O | |
| 2.23 | CH₃ | H | CH₃ | 4-Cl-phenyl | H | O | resin, MS |
| 2.24 | CH₃ | H | CH₃ | 4-Cl-phenyl | H | S | |
| 2.25 | CH₃ | H | CH₃ | 4-F-phenyl | H | O | |
| 2.26 | CH₃ | H | CH₃ | 4-F-phenyl | H | S | |
| 2.27 | CH₃ | H | CH₃ | 4-CF₃-phenyl | H | O | |
| 2.28 | CH₃ | H | CH₃ | 4-OCF₃-phenyl | H | O | |

TABLE 2-continued
Compounds of the formula I, wherein A = A2 =
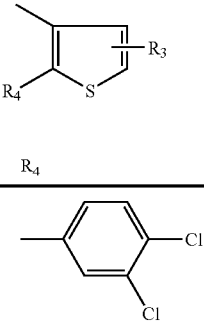
| Compd. No. | R₁ | R₂ | R₃ | R₄ | R₅ | X | Phys. data [m.p.] |
|---|---|---|---|---|---|---|---|
| 2.29 | CH₃ | H | CH₃ | 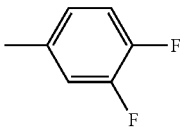 | H | O | |
| 2.30 | CH₃ | H | CH₃ | 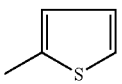 | H | O | |
| 2.31 | CH₃ | H | CH₃ | 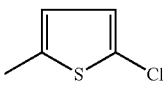 | H | O | |
| 2.32 | CH₃ | H | CH₃ | 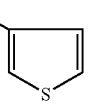 | H | O | |
| 2.33 | CH₃ | H | CH₃ | 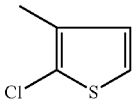 | H | O | |
| 2.34 | CH₃ | H | CH₃ | 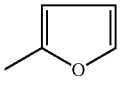 | H | O | |
| 2.35 | CH₃ | H | CH₃ | 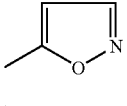 | H | O | |
| 2.36 | CH₃ | H | CH₃ | 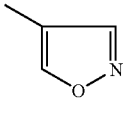 | H | O | |
| 2.37 | CH₃ | H | CH₃ | 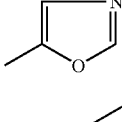 | H | O | |
| 2.38 | CH₃ | H | CH₃ | 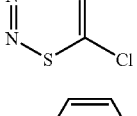 | H | O | |
| 2.39 | CH₃ | H | CH₃ | 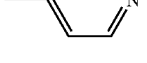 | H | O | |
| 2.40 | CH₃ | H | CH₃ |  | H | O | |

TABLE 2-continued

Compounds of the formula I, wherein A = A2 =

[structure: thiophene with R3, R4, and methyl substituent]

| Compd. No. | R₁ | R₂ | R₃ | R₄ | R₅ | X | Phys. data [m.p.] |
|---|---|---|---|---|---|---|---|
| 2.41 | CH₃ | H | CH₃ | 2-Cl-pyridin-4-yl | H | O | |
| 2.42 | CH₃ | H | CH₃ | 2-Cl-pyridin-4-yl | H | S | |
| 2.43 | CH₃ | H | CH₃ | 2-CF₃-pyridin-4-yl | H | O | |
| 2.44 | CH₃ | H | CH₃ | 2-OCF₃-pyridin-4-yl | H | O | |
| 2.45 | CH₃ | H | CH₃ | 3-Cl-pyridin-4-yl | H | O | |
| 2.46 | CH₃ | H | CH₃ | 3-F-pyridin-4-yl | H | O | |
| 2.47 | CH₃ | H | CH₃ | 3-CF₃-pyridin-4-yl | H | O | |
| 2.48 | CH₃ | H | CH₃ | pyridin-3-yl | H | O | |
| 2.49 | CH₃ | H | CH₃ | 2-Cl-pyridin-3-yl | H | O | |
| 2.50 | CH₃ | H | CH₃ | 2-CF₃-pyridin-3-yl | H | O | |

TABLE 2-continued

Compounds of the formula I, wherein A = A2 =

| Compd. No. | R₁ | R₂ | R₃ | R₄ | R₅ | X | Phys. data [m.p.] |
|---|---|---|---|---|---|---|---|
| 2.51 | CH₃ | H | CH₃ | 4-chloro-3-pyridyl | H | O | |
| 2.52 | CH₃ | H | CH₃ | 4-fluoro-3-pyridyl | H | O | |
| 2.53 | CH₃ | H | CH₃ | 6-chloro-3-pyridyl | H | O | |
| 2.54 | CH₃ | H | CH₃ | 2-pyridyl | H | O | |
| 2.55 | CH₃ | H | CH₃ | 3-chloro-2-pyridyl | H | O | |
| 2.56 | CH₃ | H | CH₃ | 3-fluoro-2-pyridyl | H | O | |
| 2.57 | CH₃ | H | CH₃ | 2-pyrimidinyl | H | O | |
| 2.58 | CH₃ | H | CH₃ | 4-chloro-2-pyrimidinyl | H | O | |
| 2.59 | CH₃ | H | CH₃ | 3-pyridazinyl | H | O | |
| 2.60 | CH₃ | H | CH₃ | 3-pyridazinyl | H | O | |
| 2.61 | CFH₂ | H | CH₃ | 1-hydroxy-1-methylcyclohexyl | H | O | |

TABLE 2-continued

Compounds of the formula I, wherein A = A2 =

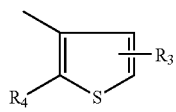

| Compd. No. | R₁ | R₂ | R₃ | R₄ | R₅ | X | Phys. data [m.p.] |
|---|---|---|---|---|---|---|---|
| 2.62 | CFH₂ | H | CH₃ | (Cl-methylcyclohexyl) | H | O | |
| 2.63 | CFH₂ | H | CH₃ | (Br-methyl-Br-cyclohexyl) | H | O | |
| 2.64 | CFH₂ | H | CH₃ | (Br-methylcyclohexenyl) | H | O | |
| 2.65 | CFH₂ | H | CH₃ | (methylcyclohexenyl) | H | O | |
| 2.66 | CFH₂ | H | CH₃ | (methylcyclohexenyl) | H | S | |
| 2.67 | CFH₂ | H | CH₃ | (methyl-4-CH₃-cyclohexenyl) | H | O | |
| 2.68 | CFH₂ | H | CH₃ | (methyl-4-CH₂CH₃-cyclohexenyl) | H | O | |
| 2.69 | CFH₂ | H | CH₃ | (methylcyclohexyl) | H | O | |
| 2.70 | CFH₂ | H | CH₃ | (methyl-4-CH₃-cyclohexyl) | H | O | |
| 2.71 | CFH₂ | H | CH₃ | (methyl-4-CH₂CH₃-cyclohexyl) | H | O | |
| 2.72 | CFH₂ | CH₃ | CH₃ | (methyl-4-CH₂CH₃-cyclohexyl) | H | O | |
| 2.73 | CFH₂ | H | CH₃ | (methylcyclohexadienyl) | H | O | |
| 2.74 | CFH₂ | H | CH₃ | (methyl-4-Cl-cyclohexadienyl) | H | O | |

TABLE 2-continued

Compounds of the formula I, wherein A = A2 =

| Compd. No. | $R_1$ | $R_2$ | $R_3$ | $R_4$ | $R_5$ | X | Phys. data [m.p.] |
|---|---|---|---|---|---|---|---|
| 2.75 | $CFH_2$ | H | $CH_3$ | 2-Cl-phenyl | H | O | |
| 2.76 | $CFH_2$ | H | $CH_3$ | 2-F-phenyl | H | O | |
| 2.77 | $CFH_2$ | H | $CH_3$ | 2-$CF_3$-phenyl | H | O | |
| 2.78 | $CFH_2$ | H | $CH_3$ | 2-$OCF_3$-phenyl | H | O | |
| 2.79 | $CFH_2$ | H | $CH_3$ | 3-Cl-phenyl | H | O | |
| 2.80 | $CFH_2$ | H | $CH_3$ | 3-F-phenyl | H | O | |
| 2.81 | $CFH_2$ | H | $CH_3$ | 3-$CF_3$-phenyl | H | O | |
| 2.82 | $CFH_2$ | H | $CH_3$ | 3-$OCF_3$-phenyl | H | O | |
| 2.83 | $CFH_2$ | H | $CH_3$ | 4-Cl-phenyl | H | O | |
| 2.84 | $CFH_2$ | H | $CH_3$ | 4-Cl-phenyl | H | S | |

TABLE 2-continued
Compounds of the formula I, wherein A = A2 =
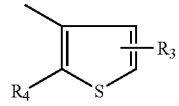
| Compd. No. | $R_1$ | $R_2$ | $R_3$ | $R_4$ | $R_5$ | X | Phys. data [m.p.] |
|---|---|---|---|---|---|---|---|
| 2.85 | $CFH_2$ | H | $CH_3$ |  | H | O | |
| 2.86 | $CFH_2$ | H | $CH_3$ |  | H | S | |
| 2.87 | $CFH_2$ | H | $CH_3$ |  | H | O | |
| 2.88 | $CFH_2$ | H | $CH_3$ | 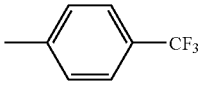 | H | O | |
| 2.89 | $CFH_2$ | H | $CH_3$ |  | H | O | |
| 2.90 | $CFH_2$ | H | $CH_3$ | 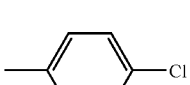 | H | O | |
| 2.91 | $CFH_2$ | H | $CH_3$ | 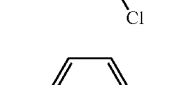 | H | O | |
| 2.92 | $CFH_2$ | H | $CH_3$ | 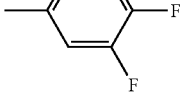 | H | O | |
| 2.93 | $CFH_2$ | H | $CH_3$ | 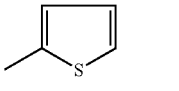 | H | O | |
| 2.94 | $CFH_2$ | H | $CH_3$ | 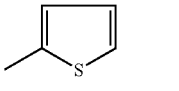 | H | O | |
| 2.95 | $CFH_2$ | H | $CH_3$ | 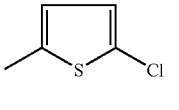 | H | O | |
| 2.96 | $CFH_2$ | H | $CH_3$ | 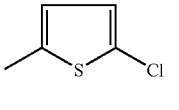 | H | O | |

TABLE 2-continued

Compounds of the formula I, wherein A = A2 =

| Compd. No. | R₁ | R₂ | R₃ | R₄ | R₅ | X | Phys. data [m.p.] |
|---|---|---|---|---|---|---|---|
| 2.97 | CFH₂ | H | CH₃ | 4-methylisoxazol-5-yl | H | O | |
| 2.98 | CFH₂ | H | CH₃ | 5-methyloxazol-2-yl | H | O | |
| 2.99 | CFH₂ | H | CH₃ | 5-chloro-4-methyl-1,2,3-thiadiazol-yl | H | O | |
| 2.100 | CFH₂ | H | CH₃ | 4-methylpyridin-2-yl | H | O | |
| 2.101 | CFH₂ | H | CH₃ | 2-chloro-4-methylpyridin-5-yl | H | O | |
| 2.102 | CFH₂ | H | CH₃ | 2-chloro-4-methylpyridin-5-yl | H | S | |
| 2.103 | CFH₂ | H | CH₃ | 2-fluoro-4-methylpyridin-5-yl | H | O | |
| 2.104 | CFH₂ | H | CH₃ | 2-trifluoromethyl-4-methylpyridin-5-yl | H | O | |
| 2.105 | CFH₂ | H | CH₃ | 2-OCF-4-methylpyridin-5-yl | H | O | |
| 2.106 | CFH₂ | H | CH₃ | 3-chloro-4-methylpyridin-5-yl | H | O | |

TABLE 2-continued

Compounds of the formula I, wherein A = A2 =

[structure: thiophene with R3, R4, S, and methyl]

| Compd. No. | R₁ | R₂ | R₃ | R₄ | R₅ | X | Phys. data [m.p.] |
|---|---|---|---|---|---|---|---|
| 2.107 | CFH₂ | H | CH₃ | 3-fluoro-pyridin-4-yl | H | O | |
| 2.108 | CFH₂ | H | CH₃ | 3-trifluoromethyl-pyridin-4-yl | H | O | |
| 2.109 | CFH₂ | H | CH₃ | pyridin-3-yl | H | O | |
| 2.110 | CFH₂ | H | CH₃ | 2-chloro-pyridin-3-yl | H | O | |
| 2.111 | CFH₂ | H | CH₃ | 2-trifluoromethyl-pyridin-3-yl | H | O | |
| 2.112 | CFH₂ | H | CH₃ | 4-chloro-pyridin-3-yl | H | O | |
| 2.113 | CFH₂ | H | CH₃ | 4-fluoro-pyridin-3-yl | H | O | |
| 2.114 | CFH₂ | H | CH₃ | 6-chloro-pyridin-3-yl | H | O | |
| 2.115 | CFH₂ | H | CH₃ | pyridin-2-yl | H | O | |
| 2.116 | CFH₂ | H | CH₃ | 3-chloro-pyridin-2-yl | H | O | |

TABLE 2-continued
Compounds of the formula I, wherein A = A2 =
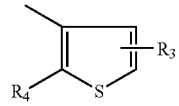
| Compd. No. | R₁ | R₂ | R₃ | R₄ | R₅ | X | Phys. data [m.p.] |
|---|---|---|---|---|---|---|---|
| 2.117 | CFH₂ | H | CH₃ | 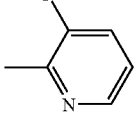 | H | O | |
| 2.118 | CFH₂ | H | CH₃ | 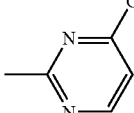 | H | O | |
| 2.119 | CFH₂ | H | CH₃ | 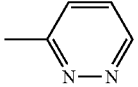 | H | O | |
| 2.120 | CFH₂ | H | CH₃ | 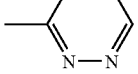 | H | O | |
| 2.121 | CFH₂ | H | CH₃ |  | H | O | |
| 2.122 | CF₂H | H | CH₃ |  | H | O | |
| 2.123 | CF₂H | H | CH₃ | 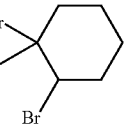 | H | O | |
| 2.124 | CF₂H | H | CH₃ | 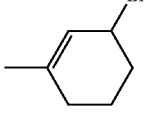 | H | O | |
| 2.125 | CF₂H | H | CH₃ | 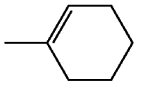 | H | O | |
| 2.126 | CF₂H | H | CH₃ | 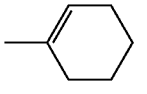 | H | O | |
| 2.127 | CF₂H | H | CH₃ | 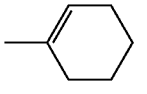 | H | S | |
| 2.128 | CF₂H | H | CH₃ | 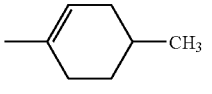 | H | O | |

TABLE 2-continued

Compounds of the formula I, wherein A = A2 =

| Compd. No. | R$_1$ | R$_2$ | R$_3$ | R$_4$ | R$_5$ | X | Phys. data [m.p.] |
|---|---|---|---|---|---|---|---|
| 2.129 | CF$_2$H | H | CH$_3$ | 4-ethylcyclohexenyl (—CH$_2$CH$_3$) | H | O | |
| 2.130 | CF$_2$H | H | CH$_3$ | cyclohexenyl | H | O | |
| 2.131 | CF$_2$H | H | CH$_3$ | 4-methylcyclohexenyl (—CH$_3$) | H | O | |
| 2.132 | CF$_2$H | H | CH$_3$ | 4-ethylcyclohexenyl (—CH$_2$CH$_3$) | H | O | |
| 2.133 | CF$_2$H | CH$_3$ | CH$_3$ | 4-ethylcyclohexenyl (—CH$_2$CH$_3$) | H | O | |
| 2.134 | CF$_2$H | H | CH$_3$ | cyclohexenyl | H | O | |
| 2.135 | CF$_2$H | H | CH$_3$ | 4-chlorophenyl (—Cl) | H | O | |
| 2.136 | CF$_2$H | H | CH$_3$ | 2-chlorophenyl (Cl) | H | O | |
| 2.137 | CF$_2$H | H | CH$_3$ | 2-fluorophenyl (F) | H | O | |
| 2.138 | CF$_2$H | H | CH$_3$ | 2-trifluoromethylphenyl (CF$_3$) | H | O | |
| 2.139 | CF$_2$H | H | CH$_3$ | 2-trifluoromethoxyphenyl (OCF$_3$) | H | O | |

TABLE 2-continued

Compounds of the formula I, wherein A = A2 =

[structure: thiophene with CH₃, R₃, R₄, S]

| Compd. No. | R₁ | R₂ | R₃ | R₄ | R₅ | X | Phys. data [m.p.] |
|---|---|---|---|---|---|---|---|
| 2.140 | CF₂H | H | CH₃ | 3-Cl-phenyl | H | O | |
| 2.141 | CF₂H | H | CH₃ | 3-F-phenyl | H | O | |
| 2.142 | CF₂H | H | CH₃ | 3-CF₃-phenyl | H | O | |
| 2.143 | CF₂H | H | CH₃ | 3-OCF₃-phenyl | H | O | |
| 2.144 | CF₂H | H | CH₃ | 4-Cl-phenyl | H | O | |
| 2.145 | CF₂H | H | CH₃ | 4-Cl-phenyl | H | S | |
| 2.146 | CF₂H | H | CH₃ | 4-F-phenyl | H | O | |
| 2.147 | CF₂H | H | CH₃ | 4-F-phenyl | H | S | |
| 2.148 | CF₂H | H | CH₃ | 4-CF₃-phenyl | H | O | |
| 2.149 | CF₂H | H | CH₃ | 4-OCF₃-phenyl | H | O | |
| 2.150 | CF₂H | H | CH₃ | 3,4-diCl-phenyl | H | O | |

TABLE 2-continued

Compounds of the formula I, wherein A = A2 =

[structure with R3, R4 on thiophene ring with methyl substituent]

| Compd. No. | R₁ | R₂ | R₃ | R₄ | R₅ | X | Phys. data [m.p.] |
|---|---|---|---|---|---|---|---|
| 2.151 | CF₂H | H | CH₃ | 3,4-difluorophenyl | H | O | |
| 2.152 | CF₂H₂ | H | CH₃ | 2-thienyl | H | O | |
| 2.153 | CF₂H | H | CH₃ | 5-chloro-2-thienyl | H | O | |
| 2.154 | CF₂H | H | CH₃ | 3-thienyl | H | O | |
| 2.155 | CF₂H | H | CH₃ | 2-chloro-3-methyl-thienyl | H | O | |
| 2.156 | CF₂H | H | CH₃ | 2-furyl | H | O | |
| 2.157 | CF₂H | H | CH₃ | isoxazolyl | H | O | |
| 2.158 | CF₂H | H | CH₃ | isoxazolyl | H | O | |
| 2.159 | CF₂H₂ | H | CH₃ | oxazolyl | H | O | |
| 2.160 | CF₂H | H | CH₃ | 5-chloro-4-methyl-thiadiazolyl | H | O | |
| 2.161 | CF₂H | H | CH₃ | 4-pyridyl | H | O | |
| 2.162 | CF₂H | H | CH₃ | 2-chloro-4-pyridyl | H | O | |

TABLE 2-continued

Compounds of the formula I, wherein A = A2 =

[thiophene structure with R3, R4, and methyl substituent]

| Compd. No. | $R_1$ | $R_2$ | $R_3$ | $R_4$ | $R_5$ | X | Phys. data [m.p.] |
|---|---|---|---|---|---|---|---|
| 2.163 | $CF_2H$ | H | $CH_3$ | 2-Cl-4-methylpyridin-4-yl | H | S | |
| 2.164 | $CF_2H$ | H | $CH_3$ | 2-F-4-methylpyridin-4-yl | H | O | |
| 2.165 | $CF_2H$ | H | $CH_3$ | 2-$CF_3$-4-methylpyridin-4-yl | H | O | |
| 2.166 | $CF_2H$ | H | $CH_3$ | 2-$OCF_3$-4-methylpyridin-4-yl | H | O | |
| 2.167 | $CF_2H$ | H | $CH_3$ | 3-Cl-4-methylpyridin-4-yl | H | O | |
| 2.168 | $CF_2H$ | H | $CH_3$ | 3-F-4-methylpyridin-4-yl | H | O | |
| 2.169 | $CF_2H$ | H | $CH_3$ | 3-$CF_3$-4-methylpyridin-4-yl | H | O | |
| 2.170 | $CF_2H$ | H | $CH_3$ | 3-methylpyridin-3-yl | H | O | |
| 2.171 | $CF_2H$ | H | $CH_3$ | 2-Cl-3-methylpyridin-3-yl | H | O | |
| 2.172 | $CF_2H$ | H | $CH_3$ | 2-$CF_3$-3-methylpyridin-3-yl | H | O | |

TABLE 2-continued

Compounds of the formula I, wherein A = A2 =

| Compd. No. | R₁ | R₂ | R₃ | R₄ | R₅ | X | Phys. data [m.p.] |
|---|---|---|---|---|---|---|---|
| 2.173 | CF₂H | H | CH₃ | 4-chloro-3-pyridyl | H | O | |
| 2.174 | CF₂H | H | CH₃ | 4-fluoro-3-pyridyl | H | O | |
| 2.175 | CF₂H | H | CH₃ | 6-chloro-3-pyridyl | H | O | |
| 2.176 | CF₂H | H | CH₃ | 2-pyridyl | H | O | |
| 2.177 | CF₂H | H | CH₃ | 3-chloro-2-pyridyl | H | O | |
| 2.178 | CF₂H | H | CH₃ | 3-fluoro-2-pyridyl | H | O | |
| 2.179 | CF₂H | H | CH₃ | 2-pyrimidyl | H | O | |
| 2.180 | CF₂H | H | CH₃ | 4-chloro-2-pyrimidyl | H | O | |
| 2.181 | CF₂H | H | CH₃ | 3-pyridazinyl | H | O | |
| 2.182 | CF₂H | H | CH₃ | 3-pyridazinyl | H | O | |
| 2.183 | CF₂CF₃ | H | CH₃ | cyclohexenyl | H | O | |

TABLE 2-continued

Compounds of the formula I, wherein A = A2 =

(thiophene structure with R3, R4, and CH3 substituent)

| Compd. No. | R₁ | R₂ | R₃ | R₄ | R₅ | X | Phys. data [m.p.] |
|---|---|---|---|---|---|---|---|
| 2.184 | CF₂CF₃ | H | CH₃ | cyclohexenyl | H | S | |
| 2.185 | CF₂CF₃ | H | CH₃ | 4-CH₃-cyclohexenyl | H | O | |
| 2.186 | CF₂CF₃ | H | CH₃ | 4-CH₂CH₃-cyclohexenyl | H | O | |
| 2.187 | CF₂CF₃ | H | CH₃ | cyclohexyl | H | O | |
| 2.188 | CF₂CF₃ | H | CH₃ | 4-CH₃-cyclohexyl | H | O | |
| 2.189 | CF₂CF₃ | H | CH₃ | 4-CH₂CH₃-cyclohexyl | H | O | |
| 2.190 | CF₂CF₃ | H | CH₃ | 4-Cl-phenyl | H | O | 145–146 |
| 2.191 | CF₂CF₃ | H | CH₃ | 4-Cl-phenyl | H | S | |
| 2.192 | CF₂CF₃ | H | CH₃ | 4-F-phenyl | H | O | 136–137 |
| 2.193 | CF₂CF₃ | H | CH₃ | 4-F-phenyl | H | S | |
| 2.194 | CF₂CF₃ | H | CH₃ | 4-CF₃-phenyl | H | O | |
| 2.195 | CF₂CF₃ | H | CH₃ | 4-OCF₃-phenyl | H | O | |
| 2.196 | CF₂CF₃ | H | CH₃ | 3,4-diCl-phenyl | H | O | |

TABLE 2-continued
Compounds of the formula I, wherein A = A2 =
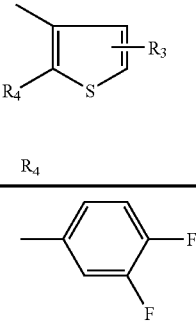
| Compd. No. | R₁ | R₂ | R₃ | R₄ | R₅ | X | Phys. data [m.p.] |
|---|---|---|---|---|---|---|---|
| 2.197 | CF₂CF₃ | H | CH₃ | 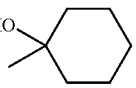 | H | O | |
| 2.198 | Δ | H | CH₃ |  | H | O | |
| 2.199 | Δ | H | CH₃ | 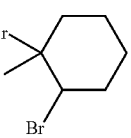 | H | O | |
| 2.200 | Δ | H | CH₃ | 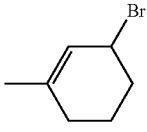 | H | O | |
| 2.201 | Δ | H | CH₃ | 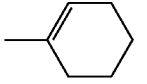 | H | O | |
| 2.202 | Δ | H | CH₃ | 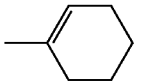 | H | O | |
| 2.203 | Δ | H | CH₃ | 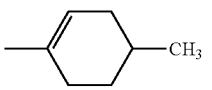 | H | S | |
| 2.204 | Δ | H | CH₃ | 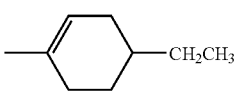 | H | O | |
| 2.205 | Δ | H | CH₃ | 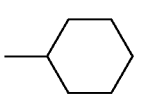 | H | O | |
| 2.206 | Δ | H | CH₃ | 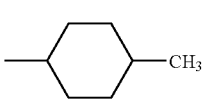 | H | O | |
| 2.207 | Δ | H | CH₃ | 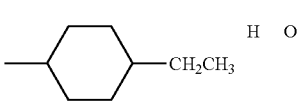 | H | O | |
| 2.208 | Δ | H | CH₃ |  | H | O | |

TABLE 2-continued

Compounds of the formula I, wherein A = A2 =

| Compd. No. | $R_1$ | $R_2$ | $R_3$ | $R_4$ | $R_5$ | X | Phys. data [m.p.] |
|---|---|---|---|---|---|---|---|
| 2.209 | Δ | $CH_3$ | $CH_3$ | 4-ethylcyclohexyl | H | O | |
| 2.210 | Δ | H | $CH_3$ | cyclohexyl | H | O | |
| 2.211 | Δ | H | $CH_3$ | 4-chlorocyclohexyl | H | O | |
| 21.212 | Δ | H | $CH_3$ | 2-chlorophenyl | H | O | |
| 2.213 | Δ | H | $CH_3$ | 2-fluorophenyl | H | O | |
| 2.214 | Δ | H | $CH_3$ | 2-trifluoromethylphenyl | H | O | |
| 2.215 | Δ | H | $CH_3$ | 2-trifluoromethoxyphenyl | H | O | |
| 2.216 | Δ | H | $CH_3$ | 3-chlorophenyl | H | O | |
| 2.217 | Δ | H | $CH_3$ | 3-fluorophenyl | H | O | |
| 2.218 | Δ | H | $CH_3$ | 3-trifluoromethylphenyl | H | O | |

TABLE 2-continued

Compounds of the formula I, wherein A = A2 =

(structure: thiophene with R3, R4, CH3, S)

| Compd. No. | R₁ | R₂ | R₃ | R₄ | R₅ | X | Phys. data [m.p.] |
|---|---|---|---|---|---|---|---|
| 2.219 | Δ | H | CH₃ | 3-OCF₃-C₆H₄ (phenyl with OCF₃) | H | O | |
| 2.220 | Δ | H | CH₃ | 4-Cl-C₆H₄ | H | O | |
| 2.221 | Δ | H | CH₃ | 4-Cl-C₆H₄ | H | S | |
| 2.222 | Δ | H | CH₃ | 4-F-C₆H₄ | H | O | |
| 2.223 | Δ | H | CH₃ | 4-F-C₆H₄ | H | S | |
| 2.224 | Δ | H | CH₃ | 4-CF₃-C₆H₄ | H | O | |
| 2.225 | Δ | H | CH₃ | 4-OCF₃-C₆H₄ | H | O | |
| 2.226 | Δ | H | CH₃ | 3,4-Cl₂-C₆H₃ | H | O | |
| 2.227 | Δ | H | CH₃ | 3,4-F₂-C₆H₃ | H | O | |
| 2.228 | Δ | H | CH₃ | 2-thienyl | H | O | |
| 2.229 | Δ | H | CH₃ | 5-Cl-2-thienyl | H | O | |
| 2.230 | Δ | H | CH₃ | 3-thienyl | H | O | |

TABLE 2-continued
Compounds of the formula I, wherein A = A2 =
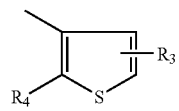
| Compd. No. | $R_1$ | $R_2$ | $R_3$ | $R_4$ | $R_5$ | X | Phys. data [m.p.] |
|---|---|---|---|---|---|---|---|
| 2.231 | Δ | H | CH$_3$ | 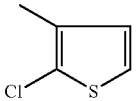 | H | O | |
| 2.232 | Δ | H | CH$_3$ | 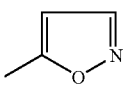 | H | O | |
| 2.233 | Δ | H | CH$_3$ | 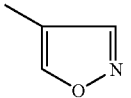 | H | O | |
| 2.234 | Δ | H | CH$_3$ | 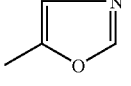 | H | O | |
| 2.235 | Δ | H | CH$_3$ | 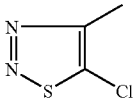 | H | O | |
| 2.236 | Δ | H | CH$_3$ | 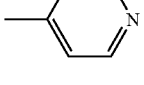 | H | O | |
| 2.237 | Δ | H | CH$_3$ | 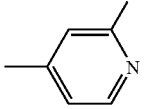 | H | O | |
| 2.238 | Δ | H | CH$_3$ | 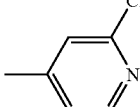 | H | O | |
| 2.239 | Δ | H | CH$_3$ | 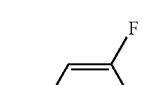 | H | S | |
| 2.240 | Δ | H | CH$_3$ | 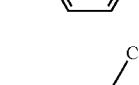 | H | O | |
| 2.241 | Δ | H | CH$_3$ |  | H | O | |

TABLE 2-continued

Compounds of the formula I, wherein A = A2 =

| Compd. No. | R₁ | R₂ | R₃ | R₄ | R₅ | X | Phys. data [m.p.] |
|---|---|---|---|---|---|---|---|
| 2.242 | Δ | H | CH₃ | 2-OCF, 4-methyl-pyridin-yl | H | O | |
| 2.243 | Δ | H | CH₃ | 3-Cl, 4-methyl-pyridin-yl | H | O | |
| 2.244 | Δ | H | CH₃ | 3-F, 4-methyl-pyridin-yl | H | O | |
| 2.245 | Δ | H | CH₃ | 3-CF₃, 4-methyl-pyridin-yl | H | O | |
| 2.246 | Δ | H | CH₃ | 5-methyl-pyridin-3-yl | H | O | |
| 2.247 | Δ | H | CH₃ | 2-Cl, 3-methyl-pyridin-yl | H | O | |
| 2.248 | Δ | H | CH₃ | 2-CF₃, 3-methyl-pyridin-yl | H | O | |
| 2.249 | Δ | H | CH₃ | 4-Cl, 3-methyl-pyridin-yl | H | O | |
| 2.250 | Δ | H | CH₃ | 4-F, 3-methyl-pyridin-yl | H | O | |
| 2.251 | Δ | H | CH₃ | 6-Cl, 3-methyl-pyridin-yl | H | O | |

TABLE 2-continued
Compounds of the formula I, wherein A = A2 =
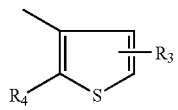
| Compd. No. | R₁ | R₂ | R₃ | R₄ | R₅ | X | Phys. data [m.p.] |
|---|---|---|---|---|---|---|---|
| 2.252 | Δ | H | CH₃ | ![2-pyridyl] | H | O | |
| 2.253 | Δ | H | CH₃ | ![3-Cl-2-pyridyl] | H | O | |
| 2.254 | Δ | H | CH₃ | ![3-F-2-pyridyl] | H | O | |
| 2.255 | Δ | H | CH₃ | ![2-pyrimidinyl] | H | O | |
| 2.256 | Δ | H | CH₃ | ![4-Cl-2-pyrimidinyl] | H | O | |
| 2.257 | Δ | H | CH₃ | ![3-pyridazinyl] | H | O | |
| 2.258 | Δ | H | CH₃ | ![3-pyridazinyl] | H | O | |
| 2.259 | CH₃ | H | CH₃ | ![2-F-4-pyridyl] | H | O | |
| 2.260 | CH₂CH₃ | H | CH₃ | ![4-Cl-phenyl] | H | O | |
| 2.261 | CH₂CH₃ | H | CH₃ | ![4-F-phenyl] | H | O | |

TABLE 3

Compounds of the formula I, wherein A = A17 =

[structure: oxazole ring with N, O, CH₃, R₅, R₄ substituents]

| Compd. No. | R₁ | R₂ | R₃ | R₄ | R₅ | X | Phys. data [m.p.] |
|---|---|---|---|---|---|---|---|
| 3.1 | CH₃ | H | CH₃ | cyclohexenyl | H | O | |
| 3.2 | CH₃ | H | CH₃ | cyclohexenyl | H | S | |
| 3.3 | CH₃ | H | CH₃ | 4-methylcyclohexenyl | H | O | |
| 3.4 | CH₃ | H | CH₃ | cyclohexyl | H | O | |
| 3.5 | CH₃ | H | CH₃ | 4-methylcyclohexyl | H | O | |
| 3.6 | CH₃ | H | CH₃ | 2-chlorophenyl | H | O | |
| 3.7 | CH₃ | H | CH₃ | 2-fluorophenyl | H | O | |
| 3.8 | CH₃ | H | CH₃ | 3-chlorophenyl | H | O | |
| 3.9 | CH₃ | H | CH₃ | 3-fluorophenyl | H | O | |
| 3.10 | CH₃ | H | CH₃ | 4-chlorophenyl | H | O | |
| 3.11 | CH₃ | H | CH₃ | 4-chlorophenyl | H | S | |
| 3.12 | CH₃ | H | CH₃ | 4-fluorophenyl | H | O | |
| 3.13 | CH₃ | H | CH₃ | 4-fluorophenyl | H | S | |
| 3.14 | CH₃ | H | CH₃ | 4-(trifluoromethyl)phenyl | H | O | |
| 3.15 | CH₃ | H | CH₃ | 4-(trifluoromethoxy)phenyl | H | O | |
| 3.16 | CH₃ | H | CH₃ | 3,4-dichlorophenyl | H | O | |
| 3.17 | CH₃ | H | CH₃ | 2-chloro-3,5-dimethylthiophen-4-yl | H | O | |
| 3.18 | CH₃ | H | CH₃ | 2-chloro-3-methylthiophen-4-yl | H | O | |
| 3.19 | CH₃ | H | CH₃ | furan-2-yl | H | O | |
| 3.20 | CH₃ | H | CH₃ | 5-methylisoxazol-3-yl | H | O | |
| 3.21 | CH₃ | H | CH₃ | 4-methylisoxazol-3-yl | H | O | |
| 3.22 | CH₃ | H | CH₃ | 5-methyloxazol-2-yl | H | O | |
| 3.23 | CH₃ | H | CH₃ | 5-chloro-4-methyl-1,2,3-thiadiazol-4-yl | H | O | |
| 3.24 | CH₃ | H | CH₃ | pyridin-4-yl | H | O | |

TABLE 3-continued

Compounds of the formula I, wherein A = A17 =

[oxazole structure with R5 at 2-position, methyl at 4-position, R4 at 5-position]

| Compd. No. | R₁ | R₂ | R₃ | R₄ | R₅ | X | Phys. data [m.p.] |
|---|---|---|---|---|---|---|---|
| 3.25 | CH₃ | H | CH₃ | 2-Cl-pyridin-4-yl | H | O | |
| 3.26 | CH₃ | H | CH₃ | 2-Cl-pyridin-4-yl | H | S | |
| 3.27 | CH₃ | H | CH₃ | 2-CF₃-pyridin-4-yl | H | O | |
| 3.28 | CH₃ | H | CH₃ | 3-Cl-pyridin-4-yl | H | O | |
| 3.29 | CH₃ | H | CH₃ | 3-F-pyridin-4-yl | H | O | |
| 3.30 | CH₃ | H | CH₃ | pyridin-3-yl | H | O | |
| 3.31 | CH₃ | H | CH₃ | 2-Cl-pyridin-3-yl | H | O | |
| 3.32 | CH₃ | H | CH₃ | 4-Cl-pyridin-3-yl | H | O | |
| 3.33 | CH₃ | H | CH₃ | 4-F-pyridin-3-yl | H | O | |
| 3.34 | CH₃ | H | CH₃ | 6-Cl-pyridin-3-yl | H | O | |
| 3.35 | CH₃ | H | CH₃ | pyridin-2-yl | H | O | |
| 3.36 | CH₃ | H | CH₃ | 3-Cl-pyridin-2-yl | H | O | |
| 3.37 | CH₃ | H | CH₃ | 3-F-pyridin-2-yl | H | O | |
| 3.38 | CH₃ | H | CH₃ | 4-Cl-pyrimidin-2-yl | H | O | |
| 3.39 | CH₃ | H | CH₃ | pyridazin-3-yl | H | O | |
| 3.40 | CH₃ | H | CH₃ | 6-Cl-pyridazin-3-yl | H | O | |
| 3.41 | Δ | H | CH₃ | cyclohex-1-en-1-yl | H | O | |
| 3.42 | Δ | H | CH₃ | cyclohex-1-en-1-yl | H | S | |
| 3.43 | Δ | H | CH₃ | cyclohexyl | H | O | |
| 3.44 | Δ | H | CH₃ | 4-CH₃-cyclohexyl | H | O | |
| 3.45 | Δ | H | CH₃ | 2-Cl-phenyl | H | O | |

TABLE 3-continued
Compounds of the formula I, wherein A = A17 =
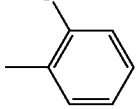
| Compd. No. | R₁ | R₂ | R₃ | R₄ | R₅ | X | Phys. data [m.p.] |
|---|---|---|---|---|---|---|---|
| 3.46 | Δ | H | CH₃ | 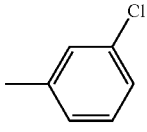 | H | O | |
| 3.47 | Δ | H | CH₃ | 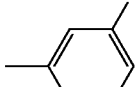 | H | O | |
| 3.48 | Δ | H | CH₃ | 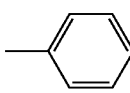 | H | O | |
| 3.49 | Δ | H | CH₃ | 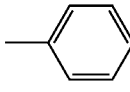 | H | O | |
| 3.50 | Δ | H | CH₃ | 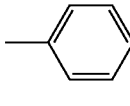 | H | S | |
| 3.51 | Δ | H | CH₃ | 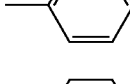 | H | O | |
| 3.52 | Δ | H | CH₃ | 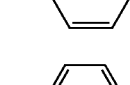 | H | S | |
| 3.53 | Δ | H | CH₃ | 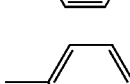 | H | O | |
| 3.54 | Δ | H | CH₃ | 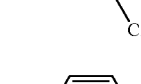 | H | O | |
| 3.55 | Δ | H | CH₃ | 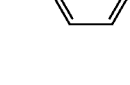 | H | O | |
| 3.56 | Δ | H | CH₃ | 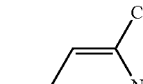 | H | O | |
| 3.57 | Δ | H | CH₃ | 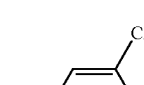 | H | O | |
| 3.58 | Δ | H | CH₃ | 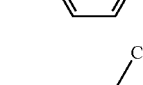 | H | S | |
| 3.59 | Δ | H | CH₃ | 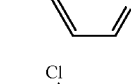 | H | O | |
| 3.60 | Δ | H | CH₃ | 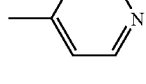 | H | O | |
| 3.61 | Δ | H | CH₃ | 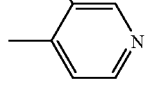 | H | O | |
| 3.62 | Δ | H | CH₃ | 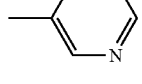 | H | O | |
| 3.63 | Δ | H | CH₃ | 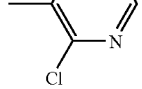 | H | O | |
| 3.64 | Δ | H | CH₃ | 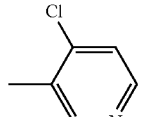 | H | O | |
| 3.65 | Δ | H | CH₃ | 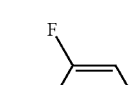 | H | O | |
| 3.66 | Δ | H | CH₃ |  | H | O | |

TABLE 3-continued

Compounds of the formula I, wherein A = A17 =

(structure: oxazole with R5 at 2-position, CH3 at 4-position, R4 at 5-position)

| Compd. No. | R1 | R2 | R3 | R4 | R5 | X | Phys. data [m.p.] |
|---|---|---|---|---|---|---|---|
| 3.67 | Δ | H | CH3 | 2-pyridyl | H | O | |
| 3.68 | Δ | H | CH3 | 3-chloro-2-pyridyl | H | O | |
| 3.69 | Δ | H | CH3 | 3-fluoro-2-pyridyl | H | O | |
| 3.70 | CF2H | H | CH3 | cyclohexenyl | H | O | |
| 3.71 | CF2H | H | CH3 | cyclohexenyl | H | S | |
| 3.72 | CF2H | H | CH3 | cyclohexyl | H | O | |
| 3.73 | CF2H | H | CH3 | 4-methylcyclohexyl | H | O | |
| 3.74 | CF2H | H | CH3 | 2-chlorophenyl | H | O | |
| 3.75 | CF2H | H | CH3 | 2-fluorophenyl | H | O | |
| 3.76 | CF2H | H | CH3 | 3-chlorophenyl | H | O | |
| 3.77 | CF2H | H | CH3 | 3-fluorophenyl | H | O | |
| 3.78 | CF2H | H | CH3 | 4-chlorophenyl | H | O | |
| 3.79 | CF2H | H | CH3 | 4-chlorophenyl | H | S | |
| 3.80 | CF2H | H | CH3 | 4-fluorophenyl | H | O | |
| 3.81 | CF2H | H | CH3 | 4-fluorophenyl | H | S | |
| 3.82 | CF2H | H | CH3 | 4-trifluoromethylphenyl | H | O | |
| 3.83 | CF2H | H | CH3 | 4-trifluoromethoxyphenyl | H | O | |
| 3.84 | CF2H | H | CH3 | 3,4-dichlorophenyl | H | O | |
| 3.85 | CF2H | H | CH3 | 4-pyridyl | H | O | |
| 3.86 | CF2H | H | CH3 | 2-chloro-4-pyridyl | H | O | |
| 3.87 | CF2H | H | CH3 | 2-chloro-4-pyridyl | H | S | |
| 3.88 | CF2H | H | CH3 | 2-trifluoromethyl-4-pyridyl | H | O | |

TABLE 3-continued

Compounds of the formula I, wherein A = A17 =

| Compd. No. | R₁ | R₂ | R₃ | R₄ | R₅ | X | Phys. data [m.p.] |
|---|---|---|---|---|---|---|---|
| 3.89 | CF₂H | H | CH₃ | 3-Cl-pyridin-5-yl | H | O | |
| 3.90 | CF₂H | H | CH₃ | 3-F-pyridin-5-yl | H | O | |
| 3.91 | CF₂H | H | CH₃ | pyridin-3-yl | H | O | |
| 3.92 | CF₂H | H | CH₃ | 2-Cl-pyridin-3-yl | H | O | |
| 3.93 | CF₂H | H | CH₃ | 4-Cl-pyridin-3-yl | H | O | |
| 3.94 | CF₂H | H | CH₃ | 4-F-pyridin-3-yl | H | O | |
| 3.95 | CF₂H | H | CH₃ | 6-Cl-pyridin-3-yl | H | O | |
| 3.96 | CF₂H | H | CH₃ | pyridin-2-yl | H | O | |
| 3.97 | CF₂H | H | CH₃ | 3-Cl-pyridin-2-yl | H | O | |
| 3.98 | CF₂H | H | CH₃ | 3-F-pyridin-2-yl | H | O | |

TABLE 4

Compounds of the formula I, wherein A = A21 =

| Compd. No. | R₁ | R₂ | R₃ | R₄ | X | Phys. data [m.p.] |
|---|---|---|---|---|---|---|
| 4.1 | CH₃ | H | CH₃ | cyclohex-1-en-1-yl | O | |
| 4.2 | CH₃ | H | CH₃ | cyclohex-1-en-1-yl | S | |
| 4.3 | CH₃ | H | CH₃ | 4-CH₃-cyclohex-1-en-1-yl | O | |
| 4.4 | CH₃ | H | CH₃ | cyclohexyl | O | |
| 4.5 | CH₃ | H | CH₃ | 4-CH₃-cyclohexyl | O | |
| 4.6 | CH₃ | H | CH₃ | 2-Cl-phenyl | O | |
| 4.7 | CH₃ | H | CH₃ | 2-F-phenyl | O | |
| 4.8 | CH₃ | H | CH₃ | 3-Cl-phenyl | O | |
| 4.9 | CH₃ | H | CH₃ | 3-F-phenyl | O | |
| 4.10 | CH₃ | H | CH₃ | 4-Cl-phenyl | O | |
| 4.11 | CH₃ | H | CH₃ | 4-Cl-phenyl | S | |
| 4.12 | CH₃ | H | CH₃ | 4-F-phenyl | O | resin |

TABLE 4-continued

Compounds of the formula I, wherein A = A21 =

(thiadiazole structure with R4 and methyl)

| Compd. No. | R₁ | R₂ | R₃ | R₄ | X | Phys. data [m.p.] |
|---|---|---|---|---|---|---|
| 4.13 | CH₃ | H | CH₃ | 4-F-phenyl | S | |
| 4.14 | CH₃ | H | CH₃ | 4-CF₃-phenyl | O | |
| 4.15 | CH₃ | H | CH₃ | 4-OCF₃-phenyl | O | |
| 4.16 | CH₃ | H | CH₃ | 3,4-diCl-phenyl | O | |
| 4.17 | CH₃ | H | CH₃ | 2-Cl-3,5-dimethyl-thiophene | O | |
| 4.18 | CH₃ | H | CH₃ | 2-Cl-3-methyl-thiophene | O | |
| 4.19 | CH₃ | H | CH₃ | 2-furyl | O | |
| 4.20 | CH₃ | H | CH₃ | 5-methyl-isoxazol-3-yl | O | |
| 4.21 | CH₃ | H | CH₃ | 4-methyl-isoxazol-3-yl | O | |
| 4.22 | CH₃ | H | CH₃ | 5-methyl-oxazol-4-yl | O | |
| 4.23 | CH₃ | H | CH₃ | 5-Cl-4-methyl-thiadiazol-3-yl | O | |
| 4.24 | CH₃ | H | CH₃ | 4-pyridyl | O | |
| 4.25 | CH₃ | H | CH₃ | 2-Cl-pyridin-4-yl | O | |
| 4.26 | CH₃ | H | CH₃ | 2-Cl-pyridin-4-yl | S | |
| 4.27 | CH₃ | H | CH₃ | 2-CF₃-pyridin-4-yl | O | |
| 4.28 | CH₃ | H | CH₃ | 3-Cl-pyridin-4-yl | O | |
| 4.29 | CH₃ | H | CH₃ | 3-F-pyridin-4-yl | O | |
| 4.30 | CH₃ | H | CH₃ | 3-pyridyl | O | |
| 4.31 | CH₃ | H | CH₃ | 2-Cl-pyridin-3-yl | O | |
| 4.32 | CH₃ | H | CH₃ | 4-Cl-pyridin-3-yl | O | |
| 4.33 | CH₃ | H | CH₃ | 4-F-pyridin-3-yl | O | |
| 4.34 | CH₃ | H | CH₃ | 6-Cl-pyridin-3-yl | O | |

TABLE 4-continued

Compounds of the formula I, wherein A = A21 =

| Compd. No. | R₁ | R₂ | R₃ | R₄ | X | Phys. data [m.p.] |
|---|---|---|---|---|---|---|
| 4.35 | CH₃ | H | CH₃ | 2-pyridyl (methyl-substituted) | O | |
| 4.36 | CH₃ | H | CH₃ | 3-chloro-2-pyridyl | O | |
| 4.37 | CH₃ | H | CH₃ | 3-fluoro-2-pyridyl | O | |
| 4.38 | CH₃ | H | CH₃ | 4-chloro-2-pyrimidinyl | O | |
| 4.39 | CH₃ | H | CH₃ | pyridazinyl | O | |
| 4.40 | CH₃ | H | CH₃ | 6-chloro-pyridazinyl | O | |
| 4.41 | Δ | H | CH₃ | cyclohexenyl | O | |
| 4.42 | Δ | H | CH₃ | cyclohexenyl | S | |
| 4.43 | Δ | H | CH₃ | cyclohexyl | O | |
| 4.44 | Δ | H | CH₃ | 4-methylcyclohexyl | O | |
| 4.45 | Δ | H | CH₃ | 2-chlorophenyl | O | |
| 4.46 | Δ | H | CH₃ | 2-fluorophenyl | O | |
| 4.47 | Δ | H | CH₃ | 3-chlorophenyl | O | |
| 4.48 | Δ | H | CH₃ | 3-fluorophenyl | O | |
| 4.49 | Δ | H | CH₃ | 4-chlorophenyl | O | |
| 4.50 | Δ | H | CH₃ | 4-chlorophenyl | S | |
| 4.51 | Δ | H | CH₃ | 4-fluorophenyl | O | |
| 4.52 | Δ | H | CH₃ | 4-fluorophenyl | S | |
| 4.53 | Δ | H | CH₃ | 4-CF₃-phenyl | O | |
| 4.54 | Δ | H | CH₃ | 4-OCF₃-phenyl | O | |
| 4.55 | Δ | H | CH₃ | 3,4-dichlorophenyl | O | |
| 4.56 | Δ | H | CH₃ | 4-pyridyl | O | |

TABLE 4-continued
Compounds of the formula I, wherein A = A21 =
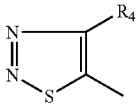
| Compd. No. | R₁ | R₂ | R₃ | R₄ | X | Phys. data [m.p.] |
|---|---|---|---|---|---|---|
| 4.57 | Δ | H | CH₃ | 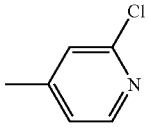 | O | |
| 4.58 | Δ | H | CH₃ | 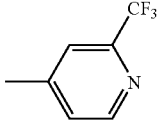 | S | |
| 4.59 | Δ | H | CH₃ | 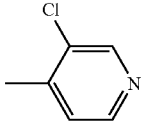 | O | |
| 4.60 | Δ | H | CH₃ | 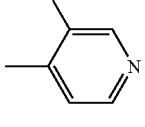 | O | |
| 4.61 | Δ | H | CH₃ | 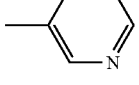 | O | |
| 4.62 | Δ | H | CH₃ | 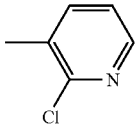 | O | |
| 4.63 | Δ | H | CH₃ | 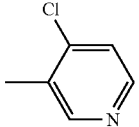 | O | |
| 4.64 | Δ | H | CH₃ | 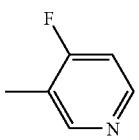 | O | |
| 4.65 | Δ | H | CH₃ | 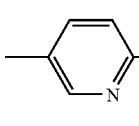 | O | |
| 4.66 | Δ | H | CH₃ | 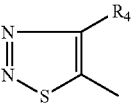 | O | |
| 4.67 | Δ | H | CH₃ | 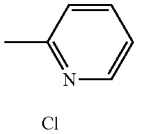 | O | |
| 4.68 | Δ | H | CH₃ | 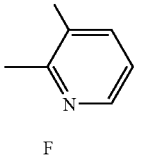 | O | |
| 4.69 | Δ | H | CH₃ | 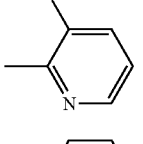 | O | |
| 4.70 | CF₂H | H | CH₃ | 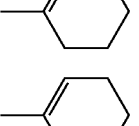 | O | |
| 4.71 | CF₂H | H | CH₃ | 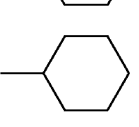 | S | |
| 4.72 | CF₂H | H | CH₃ | 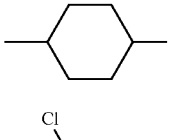 | O | |
| 4.73 | CF₂H | H | CH₃ | 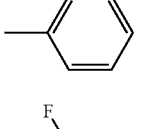 | O | |
| 4.74 | CF₂H | H | CH₃ | 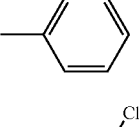 | O | |
| 4.75 | CF₂H | H | CH₃ | 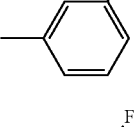 | O | |
| 4.76 | CF₂H | H | CH₃ | 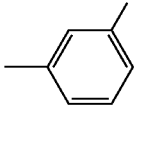 | O | |
| 4.77 | CF₂H | H | CH₃ |  | O | |

TABLE 4-continued

Compounds of the formula I, wherein A = A21 =

[Structure: thiadiazole ring with R4 at 4-position and methyl at 5-position]

| Compd. No. | R₁ | R₂ | R₃ | R₄ | X | Phys. data [m.p.] |
|---|---|---|---|---|---|---|
| 4.78 | CF₂H | H | CH₃ | 4-Cl-phenyl | O | |
| 4.79 | CF₂H | H | CH₃ | 4-Cl-phenyl | S | |
| 4.80 | CF₂H | H | CH₃ | 4-F-phenyl | O | |
| 4.81 | CF₂H | H | CH₃ | 4-F-phenyl | S | |
| 4.82 | CF₂H | H | CH₃ | 4-CF₃-phenyl | O | |
| 4.83 | CF₂H | H | CH₃ | 4-OCF₃-phenyl | O | |
| 4.84 | CF₂H | H | CH₃ | 3,4-diCl-phenyl | O | |
| 4.85 | CF₂H | H | CH₃ | 4-pyridyl | O | |
| 4.86 | CF₂H | H | CH₃ | 2-Cl-4-pyridyl | O | |
| 4.87 | CF₂H | H | CH₃ | 2-Cl-4-pyridyl | S | |
| 4.88 | CF₂H | H | CH₃ | 2-CF₃-4-pyridyl | O | |
| 4.89 | CF₂H | H | CH₃ | 3-Cl-4-pyridyl | O | |
| 4.90 | CF₂H | H | CH₃ | 3-F-4-pyridyl | O | |
| 4.91 | CF₂H | H | CH₃ | 3-pyridyl | O | |
| 4.92 | CF₂H | H | CH₃ | 2-Cl-3-pyridyl | O | |
| 4.93 | CF₂H | H | CH₃ | 4-Cl-3-pyridyl | O | |
| 4.94 | CF₂H | H | CH₃ | 4-F-3-pyridyl | O | |
| 4.95 | CF₂H | H | CH₃ | 6-Cl-3-pyridyl | O | |
| 4.96 | CF₂H | H | CH₃ | 2-pyridyl | O | |
| 4.97 | CF₂H | H | CH₃ | 3-Cl-2-pyridyl | O | |
| 4.98 | CF₂H | H | CH₃ | 3-F-2-pyridyl | O | |

TABLE 5

Compounds of the formula I, wherein A = A24 =

[Structure: pyridine ring with R5 on N, R4 substituent, methyl group]

| Compd. No. | R₁ | R₂ | R₃ | R₄ | R₅ | X | Phys. data [m.p.] |
|---|---|---|---|---|---|---|---|
| 5.1 | CH₃ | H | CH₃ | cyclohexenyl | H | O | |
| 5.2 | CH₃ | H | CH₃ | cyclohexenyl | H | S | |
| 5.3 | CH₃ | H | CH₃ | 4-methylcyclohexenyl | H | O | |
| 5.4 | CH₃ | H | CH₃ | cyclohexyl | H | O | |
| 5.5 | CH₃ | H | CH₃ | 4-methylcyclohexyl | H | O | |
| 5.6 | CH₃ | H | CH₃ | 2-chlorophenyl | H | O | |
| 5.7 | CH₃ | H | CH₃ | 2-fluorophenyl | H | O | |
| 5.8 | CH₃ | H | CH₃ | 3-chlorophenyl | H | O | |
| 5.9 | CH₃ | H | CH₃ | 3-fluorophenyl | H | O | |
| 5.10 | CH₃ | H | CH₃ | 4-chlorophenyl | H | O | |
| 5.11 | CH₃ | H | CH₃ | 4-chlorophenyl | H | S | |
| 5.12 | CH₃ | H | CH₃ | 4-fluorophenyl | H | O | |
| 5.13 | CH₃ | H | CH₃ | 4-fluorophenyl | H | S | |
| 5.14 | CH₃ | H | CH₃ | 4-trifluoromethylphenyl | H | O | |
| 5.15 | CH₃ | H | CH₃ | 4-trifluoromethoxyphenyl | H | O | |
| 5.16 | CH₃ | H | CH₃ | 3,4-dichlorophenyl | H | O | |
| 5.17 | CH₃ | H | CH₃ | 2-chloro-3,5-dimethylthien-4-yl | H | O | |
| 5.18 | CH₃ | H | CH₃ | 2-chloro-3-methylthien-4-yl | H | O | |
| 5.19 | CH₃ | H | CH₃ | 5-methylfuran-2-yl | H | O | |
| 5.20 | CH₃ | H | CH₃ | 5-methylisoxazol-3-yl | H | O | |
| 5.21 | CH₃ | H | CH₃ | isoxazolyl | H | O | |
| 5.22 | CH₃ | H | CH₃ | 5-methyloxazol-2-yl | H | O | |
| 5.23 | CH₃ | H | CH₃ | 5-chloro-4-methyl-1,2,3-thiadiazol-4-yl | H | O | |

TABLE 5-continued

Compounds of the formula I, wherein A = A24 =

| Compd. No. | R$_1$ | R$_2$ | R$_3$ | R$_4$ | R$_5$ | X | Phys. data [m.p.] |
|---|---|---|---|---|---|---|---|
| 5.24 | CH$_3$ | H | CH$_3$ | 4-pyridyl | H | O | |
| 5.25 | CH$_3$ | H | CH$_3$ | 2-chloropyridin-4-yl | H | O | |
| 5.26 | CH$_3$ | H | CH$_3$ | 2-chloropyridin-4-yl | H | S | |
| 5.27 | CH$_3$ | H | CH$_3$ | 2-trifluoromethylpyridin-4-yl | H | O | |
| 5.28 | CH$_3$ | H | CH$_3$ | 3-chloropyridin-4-yl | H | O | |
| 5.29 | CH$_3$ | H | CH$_3$ | 3-fluoropyridin-4-yl | H | O | |
| 5.30 | CH$_3$ | H | CH$_3$ | 3-pyridyl | H | O | |
| 5.31 | CH$_3$ | H | CH$_3$ | 2-chloropyridin-3-yl | H | O | |
| 5.32 | CH$_3$ | H | CH$_3$ | 4-chloropyridin-3-yl | H | O | |
| 5.33 | CH$_3$ | H | CH$_3$ | 4-fluoropyridin-3-yl | H | O | |
| 5.34 | CH$_3$ | H | CH$_3$ | 6-chloropyridin-3-yl | H | O | |
| 5.35 | CH$_3$ | H | CH$_3$ | 2-pyridyl (6-methyl) | H | O | |
| 5.36 | CH$_3$ | H | CH$_3$ | 3-chloropyridin-2-yl | H | O | |
| 5.37 | CH$_3$ | H | CH$_3$ | 3-fluoropyridin-2-yl | H | O | |
| 5.38 | CH$_3$ | H | CH$_3$ | 4-chloropyrimidin-2-yl | H | O | |
| 5.39 | CH$_3$ | H | CH$_3$ | pyridazin-3-yl | H | O | |
| 5.40 | CH$_3$ | H | CH$_3$ | 6-chloropyridazin-3-yl | H | O | |
| 5.41 | Δ | H | CH$_3$ | cyclohexenyl | H | O | |
| 5.42 | Δ | H | CH$_3$ | cyclohexenyl | H | S | |
| 5.43 | Δ | H | CH$_3$ | cyclohexyl | H | O | |
| 5.44 | Δ | H | CH$_3$ | 4-methylcyclohexyl | H | O | |

TABLE 5-continued

Compounds of the formula I, wherein A = A24 =

| Compd. No. | R$_1$ | R$_2$ | R$_3$ | R$_4$ | R$_5$ | X | Phys. data [m.p.] |
|---|---|---|---|---|---|---|---|
| 5.45 | Δ | H | CH$_3$ | 2-Cl-phenyl | H | O | |
| 5.46 | Δ | H | CH$_3$ | 2-F-phenyl | H | O | |
| 5.47 | Δ | H | CH$_3$ | 3-Cl-phenyl | h | O | |
| 5.48 | Δ | H | CH$_3$ | 3-F-phenyl | H | O | |
| 5.49 | Δ | H | CH$_3$ | 4-Cl-phenyl | H | O | |
| 5.50 | Δ | H | CH$_3$ | 4-Cl-phenyl | H | S | |
| 5.51 | Δ | H | CH$_3$ | 4-F-phenyl | H | O | |
| 5.52 | Δ | H | CH$_3$ | 4-F-phenyl | H | S | |
| 5.53 | Δ | H | CH$_3$ | 4-CF$_3$-phenyl | H | O | |
| 5.54 | Δ | H | CH$_3$ | 4-OCF$_3$-phenyl | H | O | |
| 5.55 | Δ | H | CH$_3$ | 3,4-diCl-phenyl | H | O | |
| 5.56 | Δ | H | CH$_3$ | pyridin-4-yl | H | O | |
| 5.57 | Δ | H | CH$_3$ | 2-Cl-pyridin-4-yl | H | O | |
| 5.58 | Δ | H | CH$_3$ | 2-Cl-pyridin-4-yl | H | S | |
| 5.59 | Δ | H | CH$_3$ | 2-CF$_3$-pyridin-4-yl | H | O | |
| 5.60 | Δ | H | CH$_3$ | 3-Cl-pyridin-4-yl | H | O | |
| 5.61 | Δ | H | CH$_3$ | 3-F-pyridin-4-yl | H | O | |
| 5.62 | Δ | H | CH$_3$ | pyridin-3-yl | H | O | |
| 5.63 | Δ | H | CH$_3$ | 2-Cl-pyridin-3-yl | H | O | |
| 5.64 | Δ | H | CH$_3$ | 4-Cl-pyridin-3-yl | H | O | |
| 5.65 | Δ | H | CH$_3$ | 4-F-pyridin-3-yl | H | O | |

TABLE 5-continued

Compounds of the formula I, wherein A = A24 =

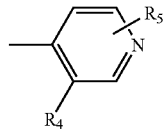

| Compd. No. | R$_1$ | R$_2$ | R$_3$ | R$_4$ | R$_5$ | X | Phys. data [m.p.] |
|---|---|---|---|---|---|---|---|
| 5.66 | Δ | H | CH$_3$ | 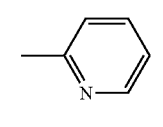 | H | O | |
| 5.67 | Δ | H | CH$_3$ | 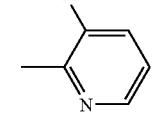 | H | O | |
| 5.68 | Δ | H | CH$_3$ | 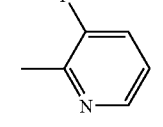 | H | O | |
| 5.69 | Δ | H | CH$_3$ | 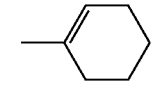 | H | O | |
| 5.70 | CF$_2$H | H | CH$_3$ | 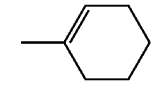 | H | O | |
| 5.71 | CF$_2$H | H | CH$_3$ | 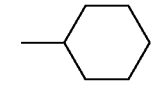 | H | S | |
| 5.72 | CF$_2$H | H | CH$_3$ | 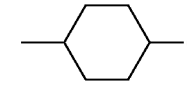 | H | O | |
| 5.73 | CF$_2$H | H | CH$_3$ | 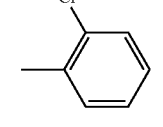 | H | O | |
| 5.74 | CF$_2$H | H | CH$_3$ | 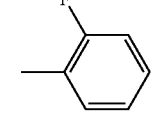 | H | O | |
| 5.75 | CF$_2$H | H | CH$_3$ | 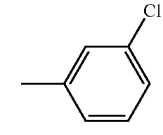 | H | O | |
| 5.76 | CF$_2$H | H | CH$_3$ | 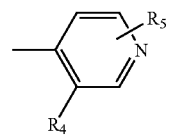 | H | O | |
| 5.77 | CF$_2$H | H | CH$_3$ | 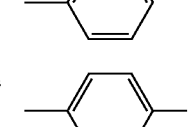 | H | O | |
| 5.78 | CF$_2$H | H | CH$_3$ | 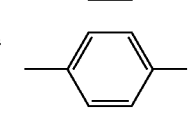 | H | O | |
| 5.79 | CF$_2$H | H | CH$_3$ | 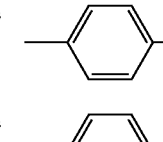 | H | S | |
| 5.80 | CF$_2$H | H | CH$_3$ | 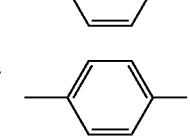 | H | O | |
| 5.81 | CF$_2$H | H | CH$_3$ | 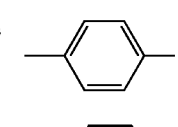 | H | S | |
| 5.82 | CF$_2$H | H | CH$_3$ | 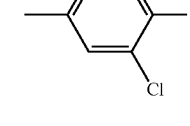 | H | O | |
| 5.83 | CF$_2$H | H | CH$_3$ | 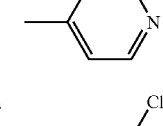 | H | O | |
| 5.84 | CF$_2$H | H | CH$_3$ | 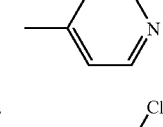 | H | O | |
| 5.85 | CF$_2$H | H | CH$_3$ | 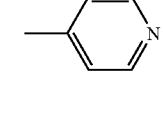 | H | O | |
| 5.86 | CF$_2$H | H | CH$_3$ |  | H | O | |
| 5.87 | CF$_2$H | H | CH$_3$ | | H | S | |

TABLE 5-continued

Compounds of the formula I, wherein A = A24 =

| Compd. No. | R₁ | R₂ | R₃ | R₄ | R₅ | X | Phys. data [m.p.] |
|---|---|---|---|---|---|---|---|
| 5.88 | CF₂H | H | CH₃ | 4-methyl-2-(CF₃)-pyridin-5-yl | H | O | |
| 5.89 | CF₂H | H | CH₃ | 3-chloro-4-methyl-pyridin-5-yl | H | O | |
| 5.90 | CF₂H | H | CH₃ | 3-fluoro-4-methyl-pyridin-5-yl | H | O | |
| 5.91 | CF₂H | H | CH₃ | 4-methyl-pyridin-3-yl | H | O | |
| 5.92 | CF₂H | H | CH₃ | 2-chloro-4-methyl-pyridin-3-yl | H | O | |
| 5.93 | CF₂H | H | CH₃ | 4-chloro-3-methyl-pyridin-5-yl | H | O | |
| 5.94 | CF₂H | H | CH₃ | 4-fluoro-3-methyl-pyridin-5-yl | H | O | |
| 5.95 | CF₂H | H | CH₃ | 2-chloro-5-methyl-pyridin-4-yl | H | O | |
| 5.96 | CF₂H | H | CH₃ | 6-methyl-pyridin-3-yl | H | O | |
| 5.97 | CF₂H | H | CH₃ | 3-chloro-2-methyl-pyridin-4-yl | H | O | |
| 5.98 | CF₂H | H | CH₃ | 3-fluoro-2-methyl-pyridin-4-yl | H | O | |

TABLE 6

Compounds of formula I, wherein A = A25 =

| Compd. No. | R₁ | R₂ | R₃ | R₄ | R₅ | X | Phys. data [m.p.] |
|---|---|---|---|---|---|---|---|
| 6.1 | CH₃ | H | CH₃ | cyclohex-1-en-1-yl | H | O | |
| 6.2 | CH₃ | H | CH₃ | cyclohex-1-en-1-yl | H | S | |
| 6.3 | CH₃ | H | CH₃ | 4-methyl-cyclohex-1-en-1-yl | H | O | |
| 6.4 | CH₃ | H | CH₃ | cyclohexyl | H | O | |
| 6.5 | CH₃ | H | CH₃ | 4-methyl-cyclohexyl | H | O | |
| 6.6 | CH₃ | H | CH₃ | 2-chloro-phenyl | H | O | |
| 6.7 | CH₃ | H | CH₃ | 2-fluoro-phenyl | H | O | |

TABLE 6-continued

Compounds of formula I, wherein A = A25 =

R4-[pyridine]-R5 with methyl substituent

| Compd. No. | R₁ | R₂ | R₃ | R₄ | R₅ | X | Phys. data [m.p.] |
|---|---|---|---|---|---|---|---|
| 6.8 | CH₃ | H | CH₃ | 3-Cl-phenyl | H | O | |
| 6.9 | CH₃ | H | CH₃ | 3-F-phenyl | H | O | |
| 6.10 | CH₃ | H | CH₃ | 4-Cl-phenyl | H | O | 203–205 |
| 6.11 | CH₃ | H | CH₃ | 4-Cl-phenyl | H | S | |
| 6.12 | CH₃ | H | CH₃ | 4-F-phenyl | H | O | 200–202 |
| 6.13 | CH₃ | H | CH₃ | 4-F-phenyl | H | S | |
| 6.14 | CH₃ | H | CH₃ | 4-CF₃-phenyl | H | O | |
| 6.15 | CH₃ | H | CH₃ | 4-OCF₃-phenyl | H | O | |
| 6.16 | CH₃ | H | CH₃ | 3,4-di-Cl-phenyl | H | O | |
| 6.17 | CH₃ | H | CH₃ | 2-Cl-3,5-dimethyl-thiophene | H | O | |
| 6.18 | CH₃ | H | CH₃ | 2-Cl-3-methyl-thiophene | H | O | |
| 6.19 | CH₃ | H | CH₃ | 5-methyl-furan-2-yl | H | O | |
| 6.20 | CH₃ | H | CH₃ | 5-methyl-isoxazol-3-yl | H | O | |
| 6.21 | CH₃ | H | CH₃ | 4-methyl-isoxazol-3-yl | H | O | |
| 6.22 | CH₃ | H | CH₃ | 5-methyl-oxazol-2-yl | H | O | |
| 6.23 | CH₃ | H | CH₃ | 5-Cl-4-methyl-thiadiazol-3-yl | H | O | |
| 6.24 | CH₃ | H | CH₃ | 4-methyl-pyridin-2-yl | H | O | |
| 6.25 | CH₃ | H | CH₃ | 2-Cl-pyridin-4-yl | H | O | |
| 6.26 | CH₃ | H | CH₃ | 2-Cl-pyridin-4-yl | H | S | |
| 6.27 | CH₃ | H | CH₃ | 2-CF₃-pyridin-4-yl | H | O | |
| 6.28 | CH₃ | H | CH₃ | 3-Cl-pyridin-4-yl | H | O | |
| 6.29 | CH₃ | H | CH₃ | 3-F-pyridin-4-yl | H | O | |
| 6.30 | CH₃ | H | CH₃ | 5-methyl-pyridin-3-yl | H | O | |

TABLE 6-continued
Compounds of formula I, wherein A = A25 =
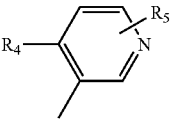
| Compd. No. | R₁ | R₂ | R₃ | R₄ | R₅ | X | Phys. data [m.p.] |
|---|---|---|---|---|---|---|---|
| 6.31 | CH₃ | H | CH₃ | 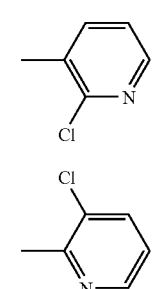 | H | O | |
| 6.32 | CH₃ | H | CH₃ | 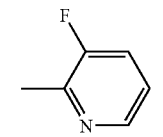 | H | O | |
| 6.33 | CH₃ | H | CH₃ | 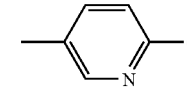 | H | O | |
| 6.34 | CH₃ | H | CH₃ | 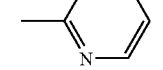 | H | O | |
| 6.35 | CH₃ | H | CH₃ | 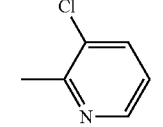 | H | O | |
| 6.36 | CH₃ | H | CH₃ | 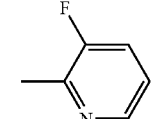 | H | O | |
| 6.37 | CH₃ | H | CH₃ | 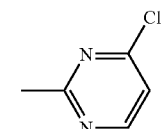 | H | O | |
| 6.38 | CH₃ | H | CH₃ | 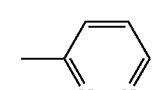 | H | O | |
| 6.39 | CH₃ | H | CH₃ | 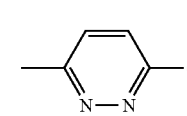 | H | O | |
| 6.40 | CH₃ | H | CH₃ | 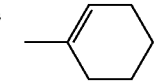 | H | O | |
| 6.41 | Δ | H | CH₃ | 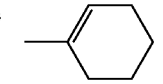 | H | O | |
| 6.42 | Δ | H | CH₃ | 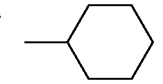 | H | S | |
| 6.43 | Δ | H | CH₃ | 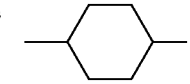 | H | O | |
| 6.44 | Δ | H | CH₃ | 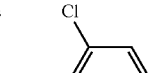 | H | O | |
| 6.45 | Δ | H | CH₃ | 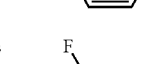 | H | O | |
| 6.46 | Δ | H | CH₃ | 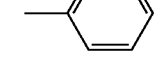 | H | O | |
| 6.47 | Δ | H | CH₃ | 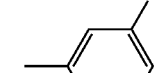 | H | O | |
| 6.48 | Δ | H | CH₃ |  | H | O | |
| 6.49 | Δ | H | CH₃ | 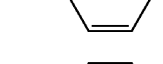 | H | O | resin; MS, ¹H-NMR |
| 6.50 | Δ | H | CH₃ | 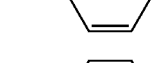 | H | S | |
| 6.51 | Δ | H | CH₃ | 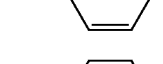 | H | O | resin; MS, ¹H-NMR |
| 6.52 | Δ | H | CH₃ | 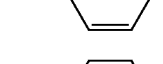 | H | S | |

TABLE 6-continued
Compounds of formula I, wherein A = A25 =
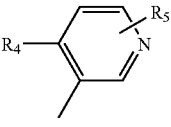
| Compd. No. | R₁ | R₂ | R₃ | R₄ | R₅ | X | Phys. data [m.p.] |
|---|---|---|---|---|---|---|---|
| 6.53 | Δ | H | CH₃ | 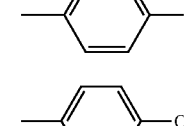 | H | O | |
| 6.54 | Δ | H | CH₃ | 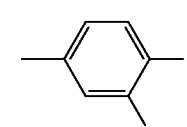 | H | O | |
| 6.55 | Δ | H | CH₃ | 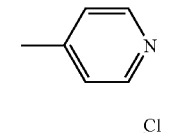 | H | O | |
| 6.56 | Δ | H | CH₃ | 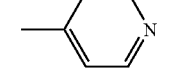 | H | O | |
| 6.57 | Δ | H | CH₃ | 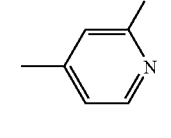 | H | O | |
| 6.58 | Δ | H | CH₃ | 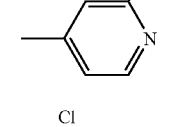 | H | S | |
| 6.59 | Δ | H | CH₃ | 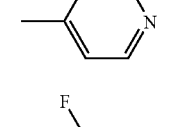 | H | O | |
| 6.60 | Δ | H | CH₃ | 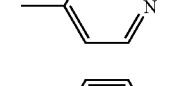 | H | O | |
| 6.61 | Δ | H | CH₃ | 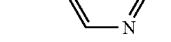 | H | O | |
| 6.62 | Δ | H | CH₃ | 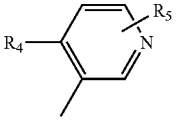 | H | O | |
| 6.63 | Δ | H | CH₃ | 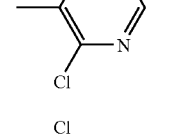 | H | O | |
| 6.64 | Δ | H | CH₃ | 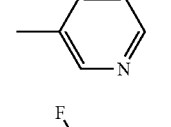 | H | O | |
| 6.65 | Δ | H | CH₃ | 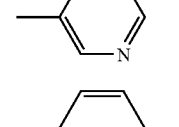 | H | O | |
| 6.66 | Δ | H | CH₃ | 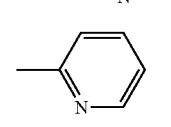 | H | O | |
| 6.67 | Δ | H | CH₃ | 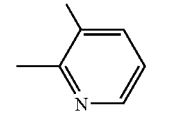 | H | O | |
| 6.68 | Δ | H | CH₃ | 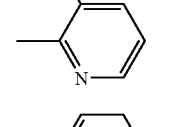 | H | O | |
| 6.69 | Δ | H | CH₃ | 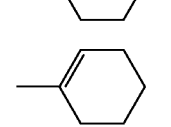 | H | O | |
| 6.70 | CF₂H | H | CH₃ | 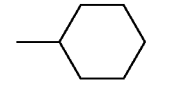 | H | O | |
| 6.71 | CF₂H | H | CH₃ | 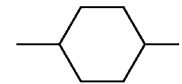 | H | S | |
| 6.72 | CF₂H | H | CH₃ |  | H | O | |
| 6.73 | CF₂H | H | CH₃ |  | H | O | |

TABLE 6-continued

Compounds of formula I, wherein A = A25 =

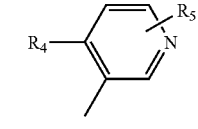

| Compd. No. | $R_1$ | $R_2$ | $R_3$ | $R_4$ | $R_5$ | X | Phys. data [m.p.] |
|---|---|---|---|---|---|---|---|
| 6.74 | $CF_2H$ | H | $CH_3$ | 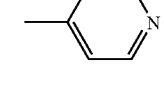 | H | O | |
| 6.75 | $CF_2H$ | H | $CH_3$ | 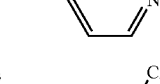 | H | O | |
| 6.76 | $CF_2H$ | H | $CH_3$ | 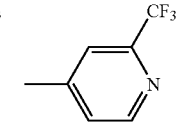 | H | O | |
| 6.77 | $CF_2H$ | H | $CH_3$ | 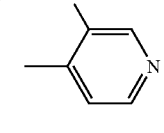 | H | O | |
| 6.78 | $CF_2H$ | H | $CH_3$ | 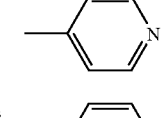 | H | O | |
| 6.79 | $CF_2H$ | H | $CH_3$ | 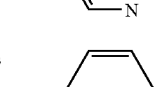 | H | S | |
| 6.80 | $CF_2H$ | H | $CH_3$ | 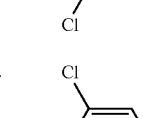 | H | O | |
| 6.81 | $CF_2H$ | H | $CH_3$ | 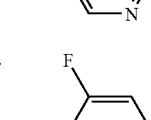 | H | S | |
| 6.82 | $CF_2H$ | H | $CH_3$ |  | H | O | |
| 6.83 | $CF_2H$ | H | $CH_3$ | | H | O | |
| 6.84 | $CF_2H$ | H | $CH_3$ | | H | O | |

TABLE 6-continued

Compounds of formula I, wherein A = A25 =

| Compd. No. | $R_1$ | $R_2$ | $R_3$ | $R_4$ | $R_5$ | X | Phys. data [m.p.] |
|---|---|---|---|---|---|---|---|
| 6.85 | $CF_2H$ | H | $CH_3$ | | H | O | |
| 6.86 | $CF_2H$ | H | $CH_3$ | | H | O | |
| 6.87 | $CF_2H$ | H | $CH_3$ | | H | S | |
| 6.88 | $CF_2H$ | H | $CH_3$ | | H | O | |
| 6.89 | $CF_2H$ | H | $CH_3$ | | H | O | |
| 6.90 | $CF_2H$ | H | $CH_3$ | | H | O | |
| 6.91 | $CF_2H$ | H | $CH_3$ | | H | O | |
| 6.92 | $CF_2H$ | H | $CH_3$ | | H | O | |
| 6.93 | $CF_2H$ | H | $CH_3$ | | H | O | |
| 6.94 | $CF_2H$ | H | $CH_3$ | | H | O | |

TABLE 6-continued

Compounds of formula I, wherein A = A25 =

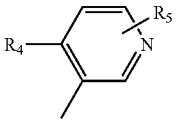

| Compd. No. | R$_1$ | R$_2$ | R$_3$ | R$_4$ | R$_5$ | X | Phys. data [m.p.] |
|---|---|---|---|---|---|---|---|
| 6.95 | CF$_2$H | H | CH$_3$ | 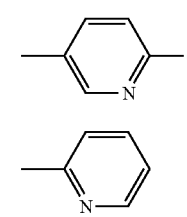 | H | O | |
| 6.96 | CF$_2$H | H | CH$_3$ | 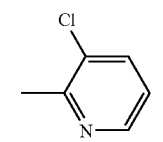 | H | O | |
| 6.97 | CF$_2$H | H | CH$_3$ | 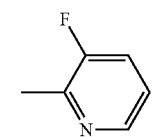 | H | O | |
| 6.98 | CF$_2$H | H | CH$_3$ | 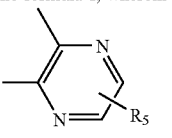 | H | O | |

TABLE 7

Compounds of the formula I, wherein A = A26 =

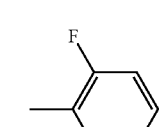

| Compd. No. | R$_1$ | R$_2$ | R$_3$ | R$_4$ | R$_5$ | X | Phys. data [m.p.] |
|---|---|---|---|---|---|---|---|
| 7.1 | CH$_3$ | H | CH$_3$ | 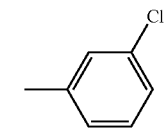 | H | O | |
| 7.2 | CH$_3$ | H | CH$_3$ | 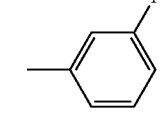 | H | S | |
| 7.3 | CH$_3$ | H | CH$_3$ |  | H | O | |
| 7.4 | CH$_3$ | H | CH$_3$ | 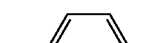 | H | O | |
| 7.5 | CH$_3$ | H | CH$_3$ | 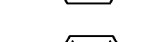 | H | O | |
| 7.6 | CH$_3$ | H | CH$_3$ | 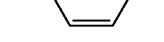 | H | O | |
| 7.7 | CH$_3$ | H | CH$_3$ |  | H | O | |
| 7.8 | CH$_3$ | H | CH$_3$ |  | H | O | |
| 7.9 | CH$_3$ | H | CH$_3$ | 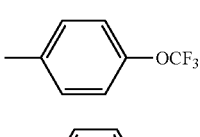 | H | O | |
| 7.10 | CH$_3$ | H | CH$_3$ | 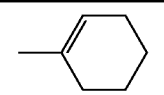 | H | O | |
| 7.11 | CH$_3$ | H | CH$_3$ | 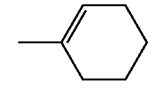 | H | O | |
| 7.12 | CH$_3$ | H | CH$_3$ | 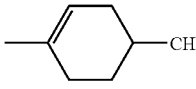 | H | O | |
| 7.13 | CH$_3$ | H | CH$_3$ |  | H | S | |
| 7.14 | CH$_3$ | H | CH$_3$ | 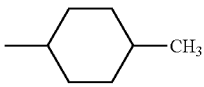 | H | O | |
| 7.15 | CH$_3$ | H | CH$_3$ | | H | O | |
| 7.16 | CH$_3$ | H | CH$_3$ | | H | O | |

TABLE 7-continued
Compounds of the formula I, wherein A = A26 =
| Compd. No. | R1 | R2 | R3 | R4 | R5 | X | Phys. data [m.p.] |
|---|---|---|---|---|---|---|---|
| 7.17 | CH3 | H | CH3 | 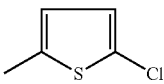 | H | O | |
| 7.18 | CH3 | H | CH3 | 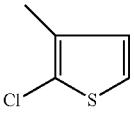 | H | O | |
| 7.19 | △ | H | CH3 |  | H | O | |
| 7.20 | △ | H | CH3 | 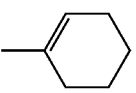 | H | S | |
| 7.21 | △ | H | CH3 |  | H | O | |
| 7.22 | △ | H | CH3 | 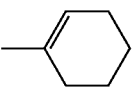 | H | O | |
| 7.23 | △ | H | CH3 |  | H | O | |
| 7.24 | △ | H | CH3 | 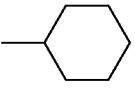 | H | O | |
| 7.25 | △ | H | CH3 |  | H | O | |
| 7.26 | △ | H | CH3 | 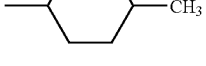 | H | O | |
| 7.27 | △ | H | CH3 |  | H | O | |
| 7.28 | △ | H | CH3 | 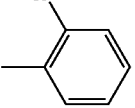 | H | S | |
| 7.29 | △ | H | CH3 |  | H | O | |
| 7.30 | △ | H | CH3 | 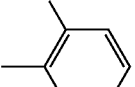 | H | O | |
| 7.31 | △ | H | CH3 |  | H | O | |
| 7.32 | △ | H | CH3 | 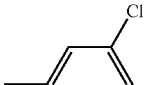 | H | O | |
| 7.33 | △ | H | CH3 |  | H | O | |
| 7.34 | CF2H | H | CH3 | 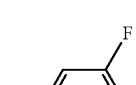 | H | O | |
| 7.35 | CF2H | H | CH3 |  | H | S | |
| 7.36 | CF2H | H | CH3 |  | H | O | |
| 7.37 | CF2H | H | CH3 |  | H | O | |
| 7.38 | CF2H | H | CH3 | 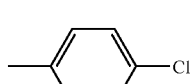 | H | O | |
| 7.39 | CF2H | H | CH3 |  | H | O | |
| 7.40 | CF2H | H | CH3 | 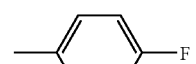 | H | O | |

TABLE 7-continued

Compounds of the formula I, wherein A = A26 =

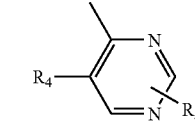

| Compd. No. | R₁ | R₂ | R₃ | R₄ | R₅ | X | Phys. data [m. p.] |
|---|---|---|---|---|---|---|---|
| 7.41 | CF₂H | H | CH₃ | 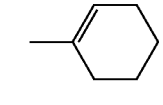 | H | O | |
| 7.42 | CF₂H | H | CH₃ | 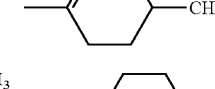 | H | O | |
| 7.43 | CF₂H | H | CH₃ | 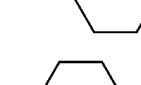 | H | S | |
| 7.44 | CF₂H | H | CH₃ | 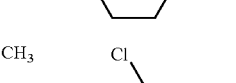 | H | O | |
| 7.45 | CF₂H | H | CH₃ | 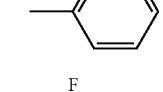 | H | S | |
| 7.46 | CF₂H | H | CH₃ | 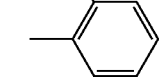 | H | O | |
| 7.47 | CF₂H | H | CH₃ | 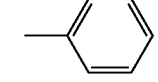 | H | O | |
| 7.48 | CF₂H | H | CH₃ | 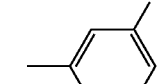 | H | O | |

TABLE 8

Compounds of the formula I, wherein A = A27 =

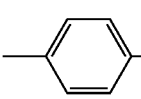

| Compd. No. | R₁ | R₂ | R₃ | R₄ | R₅ | X | Phys. data [m. p.] |
|---|---|---|---|---|---|---|---|
| 8.1 | CH₃ | H | CH₃ | 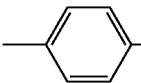 | H | O | |
| 8.2 | CH₃ | H | CH₃ | 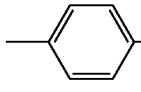 | H | S | |
| 8.3 | CH₃ | H | CH₃ | 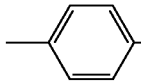 | H | O | |
| 8.4 | CH₃ | H | CH₃ | | H | O | |
| 8.5 | CH₃ | H | CH₃ | | H | O | |
| 8.6 | CH₃ | H | CH₃ | | H | O | |
| 8.7 | CH₃ | H | CH₃ | | H | O | |
| 8.8 | CH₃ | H | CH₃ | | H | O | |
| 8.9 | CH₃ | H | CH₃ | | H | O | |
| 8.10 | CH₃ | H | CH₃ | | H | O | |
| 8.11 | CH₃ | H | CH₃ | | H | S | |
| 8.12 | CH₃ | H | CH₃ | | H | O | |
| 8.13 | CH₃ | H | CH₃ | | H | S | |

TABLE 8-continued

Compounds of the formula I, wherein A = A27 =

(structure: pyrimidine with R4 at 5-position, R5 at 2-position)

| Compd. No. | R₁ | R₂ | R₃ | R₄ | R₅ | X | Phys. data [m. p.] |
|---|---|---|---|---|---|---|---|
| 8.14 | CH₃ | H | CH₃ | 4-CF₃-phenyl | H | O | |
| 8.15 | CH₃ | H | CH₃ | 4-OCF₃-phenyl | H | O | |
| 8.16 | CH₃ | H | CH₃ | 3,4-diCl-phenyl | H | O | |
| 8.17 | CH₃ | H | CH₃ | 5-methyl-2-chloro-thienyl | H | O | |
| 8.18 | CH₃ | H | CH₃ | 3-methyl-2-chloro-thienyl | H | O | |
| 8.19 | △ | H | CH₃ | cyclohexenyl | H | O | |
| 8.20 | △ | H | CH₃ | cyclohexenyl | H | S | |
| 8.21 | △ | H | CH₃ | cyclohexyl | H | O | |
| 8.22 | △ | H | CH₃ | 4-methyl-cyclohexyl | H | O | |
| 8.23 | △ | H | CH₃ | 2-Cl-phenyl | H | O | |
| 8.24 | △ | H | CH₃ | 2-F-phenyl | H | O | |
| 8.25 | △ | H | CH₃ | 3-Cl-phenyl | H | O | |
| 8.26 | △ | H | CH₃ | 3-F-phenyl | H | O | |
| 8.27 | △ | H | CH₃ | 4-Cl-phenyl | H | O | |
| 8.28 | △ | H | CH₃ | 4-Cl-phenyl | H | S | |
| 8.29 | △ | H | CH₃ | 4-F-phenyl | H | O | |
| 8.30 | △ | H | CH₃ | 4-F-phenyl | H | S | |
| 8.31 | △ | H | CH₃ | 4-CF₃-phenyl | H | O | |
| 8.32 | △ | H | CH₃ | 4-OCF₃-phenyl | H | O | |
| 8.33 | △ | H | CH₃ | 3,4-diCl-phenyl | H | O | |
| 8.34 | CF₂H | H | CH₃ | cyclohexenyl | H | O | |
| 8.35 | CF₂H | H | CH₃ | cyclohexenyl | H | S | |
| 8.36 | CF₂H | H | CH₃ | cyclohexyl | H | O | |
| 8.37 | CF₂H | H | CH₃ | 4-methyl-cyclohexyl | H | O | |

TABLE 8-continued

Compounds of the formula I, wherein A = A27 =

| Compd. No. | $R_1$ | $R_2$ | $R_3$ | $R_4$ | $R_5$ | X | Phys. data [m. p.] |
|---|---|---|---|---|---|---|---|
| 8.38 | $CF_2H$ | H | $CH_3$ | 2-Cl-phenyl | H | O | |
| 8.39 | $CF_2H$ | H | $CH_3$ | 2-F-phenyl | H | O | |
| 8.40 | $CF_2H$ | H | $CH_3$ | 3-Cl-phenyl | H | O | |
| 8.41 | $CF_2H$ | H | $CH_3$ | 3-F-phenyl | H | O | |
| 8.42 | $CF_2H$ | H | $CH_3$ | 4-Cl-phenyl | H | O | |
| 8.43 | $CF_2H$ | H | $CH_3$ | 4-Cl-phenyl | H | S | |
| 8.44 | $CF_2H$ | H | $CH_3$ | 4-F-phenyl | H | O | |
| 8.45 | $CF_2H$ | H | $CH_3$ | 4-F-phenyl | H | S | |
| 8.46 | $CF_2H$ | H | $CH_3$ | 4-$CF_3$-phenyl | H | O | |
| 8.47 | $CF_2H$ | H | $CH_3$ | 4-$OCF_3$-phenyl | H | O | |
| 8.48 | $CF_2H$ | H | $CH_3$ | 3,4-di-Cl-phenyl | H | O | |

TABLE 9

Compounds of the formula I, wherein A = A31 =

| Compd. No. | $R_1$ | $R_2$ | $R_3$ | $R_5$ | X | Phys. data m. p. ° C. |
|---|---|---|---|---|---|---|
| 9.1 | $CH_3$ | H | $CH_3$ | H | O | resin, MS |
| 9.2 | $CH_3$ | H | $CH_3$ | H | S | |
| 9.3 | $CF_2H$ | H | $CH_3$ | H | O | |
| 9.4 | $CF_2H$ | H | $CH_3$ | H | S | |
| 9.5 | $CFH_2$ | H | $CH_3$ | H | O | |
| 9.6 | $CFH_2$ | H | $CH_3$ | H | S | |
| 9.7 | cyclopropyl | H | $CH_3$ | H | O | |
| 9.8 | cyclopropyl | H | $CH_3$ | H | S | |
| 9.9 | cyclopropyl | H | $CH_2OCH_3$ | H | O | |
| 9.10 | cyclopropyl | H | $CH_2OCH_3$ | H | S | |
| 9.11 | $CH_2CH_3$ | H | $CH_3$ | H | O | resin, MS |

TABLE 10

Compounds of formula I, wherein A = A33 =

| Compd. No. | $R_1$ | $R_2$ | $R_3$ | $R_5$ | X | Phys. data m. p. ° C. |
|---|---|---|---|---|---|---|
| 10.1 | $CH_3$ | H | $CH_3$ | H | O | |
| 10.2 | $CH_2CH_3$ | H | $CH_3$ | H | O | |
| 10.3 | $CF_2H$ | H | $CH_3$ | H | O | |
| 10.4 | $CF_2H$ | H | $CH_2OCH_3$ | H | O | |
| 10.5 | $CF_2CF_3$ | H | $CH_3$ | H | O | 168–169 |

TABLE 11

Pyrrole carboxylic acid of the formula X (X), wherein $R_2$ is hydrogen

| Compd. No. | $R_1$ | $R_3$ | Phys. data m. p. ° C. |
|---|---|---|---|
| 11.1 | $CH_3$ | $CH_3$ | 166–168 |
| 11.2 | $CH_3$ | $CH_2CH_3$ | |
| 11.3 | $CH_3$ | $CHF_2$ | |
| 11.4 | $CH_3$ | $CH_2OCH_3$ | |
| 11.5 | $CH_3$ | $CH_2OCF_3$ | |

TABLE 11-continued

Pyrrole carboxylic acid of the formula X
(X), wherein $R_2$ is hydrogen

| Compd. No. | $R_1$ | $R_3$ | Phys. data m. p. ° C. |
|---|---|---|---|
| 11.6 | $CHF_2$ | $CH_3$ | |
| 11.7 | $CHF_2$ | $CH_2CH_3$ | |
| 11.8 | $CHF_2$ | $CH_2OCH_3$ | |
| 11.9 | $CH_2F$ | $CH_3$ | |
| 11.10 | $CH_2F$ | $CH_2CH_3$ | |
| 11.11 | $CH_2F$ | $CH_2OCH_3$ | |
| 11.12 | $CH_2CH_3$ | $CH_3$ | 164–165 |
| 11.13 | $CH_2CH_3$ | $CH_2OCH_3$ | |
| 11.14 | $CF_2CF_3$ | $CH_3$ | 180–181 |
| 11.15 | △ | $CH_3$ | 182–183 |
| 11.16 | △ | $CH_2CH_3$ | |
| 11.17 | △ | $CHF_2$ | |
| 11.18 | △ | $CH_2OCH_3$ | |
| 11.19 | △ | $CH_2OCF_3$ | |
| 11.20 | $CH_2CH_3$ | $CH_2CH_3$ | 68 |
| 11.21 | $(CH_3)_2CH$ | $CH_3$ | 158–159 |
| 11.22 | $(CH_3)_2CH$ | $CH_2CH_3$ | 99–100 |

TABLE 12

$^1$H-NMR of selected compounds

| Cmpd. No. | $^1$H-NMR-data (ppm/multiplicity/ number of H's); solvent=$CDCl_3$ |
|---|---|
| 1.5 | 1.60–1.85/m/4H; 2.15–2.30/m/4H; 3.62/s/3H; 5.80/m/1H; 6.39/m/1H; 6.95–7.15/m/3H; 7.20–7.30/m/1H; 7.94/s/1H; 8.46/d/1H |
| 1.206 | 0.68–0.74/m/2H; 0.91–0.98/m/2H; 1.29–1.94/m/11H; 2.72/m/1H; 3.55/s/3H; 6.35/m/1H; 7.13–7.34/m/4H; 7.75/m/1H; 8.19/s/1H(NH) |
| 1.220 | 0.22–0.29/m/4H; 1.20/m/1H; 3.57/s/3H; 6.22/m/1H; 7.10–7.28/m/4H; 7.32–7.45/m/4H; 8.15/s/1H; 8.35/d/1H |
| 6.49 | 0.29/m/4H; 1.23/m/1H; 3.58/s/3H; 6.24/m/1H; 6.98–7.50/m/5H; 8.06/d/1H; 8.15/m/2H(NH + 1 pyridin-H); 8.42/d/1H |
| 6.51 | 0.27/m/4H; 1.25/m/1H; 3.59/s/3H; 6.23/m/1H; 6.99–7.48/m/7H; 8.15/s/1H; 8.42/d/1H; |

FORMULATION EXAMPLES FOR COMPOUNDS OF FORMULA I

Working procedures for preparing formulations of the compounds of formula I such as Emulsifiable concentrates, Solutions, Granulates, Dusts and Wettable powders are described in WO 97/33890.

BIOLOGICAL EXAMPLES

Fungicidal Actions

EXAMPLE B-1

Action Against *Puccinia recondita*/Wheat (Brownrust on Wheat)

1 week old wheat plants cv. Arina are treated with the formulated test compound (0.02% active ingredient) in a spray chamber. One day after application wheat plants are inoculated by spraying a spore suspension ($1 \times 10^5$ uredospores/ml) on the test plants. After an incubation period of 2 days at 20° C. and 95% r. h. plants are kept in a greenhouse for 8 days at 20° C. and 60% r.h. The disease incidence is assessed 10 days after inoculation. Compounds of Tables 1 to 10 show good activity in these tests. The compounds 1.5, 1.9, 1.23, 1.25, 1.46, 1.144, 1.153, 1.183, 1.187, 1.190, 1.192, 1.206, 1.244, 1,260, 1.261, 1.265, 1.266, 1.268, 1.269, 1.271, 1.272, 2.23, 2.190, 2.192, 4.12, 6.10, 6.12, 6.49, 6.51 and 10.5 exhibit strong efficacy (<20% infestation).

EXAMPLE B-2

Action Against *Podosphaera leucotricha*/Apple (Powdery Mildew on Apple)

5 week old apple seedlings cv. McIntosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r. h. under a light regime of 14/10 h (light/dark) the disease incidence is assessed.

Compounds of Tables 1 to 10 show good activity in this test. The compounds 1.5, 1.9, 1.23, 1.25, 1.46, 1.144, 1.153, 1.183, 1.187, 1.190, 1.192, 1.206, 1.244, 1,260, 1.261, 1.265, 1.266, 1.268, 1.269, 1.271, 1.272, 2.23, 2.190, 2.192, 4.12, 6.10, 6.12, 6.49, 6.51 and 10.5 exhibit strong efficacy.

EXAMPLE B-3

Action Against *Venturia inaequalis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4 \times 10^5$ conidia/ml) on the test plants. After an incubation period of 4 days at 21° C. and 95% r. h. the plants are placed for 4 days at 21° C. and 60% r. h. in a greenhouse. After another 4 day incubation period at 21° C. and 95% r. h. the disease incidence is assessed.

Compounds of Tables 1 to 10 show good activity in this test. The compounds 1.5, 1.9, 1.23, 1.25, 1.46, 1.144, 1.153, 1.183, 1.187, 1.190, 1.192, 1.206, 1.244, 1,260, 1.261, 1.265, 1.266, 1.268, 1.269, 1.271, 1.272, 2.23, 2.190, 2.192, 4.12, 6.10, 6.12, 6.49, 6.51 and 10.5 exhibit strong efficacy.

EXAMPLE B-4

Action Against *Erysiphe qraminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r. h. in a greenhouse the disease incidence is assessed.

Compounds of Tables 1 to 10 show good activity in this test. The compounds 1.5, 1.9, 1.23, 1.25, 1.46, 1.144, 1.153, 1.183, 1.187, 1.190, 1.192, 1.206, 1.244, 1,260, 1.261, 1.265, 1.266, 1.268, 1.269, 1.271, 1.272, 2.23, 2.190, 2.192, 4.12, 6.10, 6.12, 6.49, 6.51 and 10.5 exhibit strong efficacy.

EXAMPLE B-5

Action Against *Botrytis cinerea*/Apple (*Botrytis* on Apple Fruits)

In an apple fruit cv. Golden Delicious 3 holes are drilled and each filled with 30 μl droplets of the formulated test compound (0.002% active ingredient). Two hours after application 50 μl of a spore suspension of *B. cinerea* ($4 \times 10^5$ conidia/ml) are pipetted on the application sites. After an incubation period of 7 days at 22° C. in a growth chamber the disease incidence is assessed.

Compounds of Tables 1 to 10 show good activity in this test. The compounds 1.5, 1.9, 1.23, 1.25, 1.46, 1.144, 1.153, 1.183, 1.187, 1.190, 1.192, 1.206, 1.244, 1,260, 1.261, 1.265, 1.266, 1.268, 1.269, 1.271, 1.272, 2.23, 2.190, 2.192, 4.12, 6.10, 6.12, 6.49, 6.51 and 10.5 exhibit strong efficacy.

EXAMPLE B-6

Action Against *Botrytis cinerea*/Grape (*Botrytis* on Grapes)

5 week old grape seedlings cv. Gutedel are treated with the formulated test compound (0.002% active ingredient) in a spray chamber. Two days after application grape plants are inoculated by spraying a spore suspension ($1 \times 10^6$ conidia/ml) on the test plants. After an incubation period of 4 days at 21° C. and 95% r. h. in a greenhouse the disease incidence is assessed.

Compounds of Tables 1 to 10 show good activity in this test. The compounds 1.5, 1.9, 1.23, 1.25, 1.46, 1.144, 1.153, 1.183, 1.187, 1.190, 1.192, 1.206, 1.244, 1,260, 1.261, 1.265, 1.266, 1.268, 1.269, 1.271, 1.272, 2.23, 2.190, 2.192, 4.12, 6.10, 6.12, 6.49, 6.51 and 10.5 exhibit strong efficacy.

EXAMPLE B-7

Action Against *Botrytis cinerea*/Tomato (*Botrytis* on Tomatoes)

4 week old tomato plants cv. Roter Gnom are treated with the formulated test compound (0.002% active ingredient) in a spray chamber. Two days after application tomato plants are inoculated by spraying a spore suspension ($1 \times 10^5$ conidia/ml) on the test plants. After an incubation period of 4 days at 20° C. and 95% r.h. in a growth chamber the disease incidence is assessed.

Compounds of Tables 1 to 10 show good activity in this test. The compounds 1.5, 1.9, 1.23, 1.25, 1.46, 1.144, 1.153, 1.183, 1.187, 1.190, 1.192, 1.206, 1.244, 1,260, 1.261, 1.265, 1.266, 1.268, 1.269, 1.271, 1.272, 2.23, 2.190, 2.192, 4.12, 6.10, 6.12, 6.49, 6.51 and 10.5 exhibit strong efficacy.

EXAMPLE B-8

Action Against *Pyrenophora teres*/Barley (Net Blotch on Barley)

1 week old barley plants cv. Express are treated with the formulated test compound (0.002% active ingredient) in a spray chamber. Two days after application barley plants are inoculated by spraying a spore suspension ($3 \times 10^4$ conidia/ml) on the test plants. After an incubation period of 2 days at 20° C. and 95% r. h. plants are kept for 2 days at 20° C. and 60% r.h. in a greenhouse. The disease incidence is assessed 4 days after inoculation.

Compounds of Tables 1 to 10 show good activity in this test. The compounds 1.5, 1.9, 1.23, 1.25, 1.46, 1.144, 1.153, 1.183, 1.187, 1.190, 1.192, 1.206, 1.244, 1,260, 1.261, 1.265, 1.266, 1.268, 1.269, 1.271, 1.272, 2.23, 2.190, 2.192, 4.12, 6.10, 6.12, 6.49, 6.51 and 10.5 exhibit strong efficacy.

EXAMPLE B-9

Action Against *Septoria nodorum*/Wheat (*Septoria* Leaf Spot on Wheat)

1 week old wheat plants cv. Arina are treated with the formulated test compound (0.02% active ingredient) in a spray chamber. One day after application wheat plants are inoculated by spraying a spore suspension ($5 \times 10^5$ conidia/ml) on the test plants. After an incubation period of 1 day at 20° C. and 95% r. h. plants are kept for 10 days at 20° C. and 60% r.h. in a greenhouse. The disease incidence is assessed 11 days after inoculation.

Compounds of Tables 1 to 10 show good activity in this test. The compounds 1.5, 1.9, 1.23, 1.25, 1.46, 1.144, 1.153, 1.183, 1.187, 1.190, 1.192, 1.206, 1.244, 1,260, 1.261, 1.265, 1.266, 1.268, 1.269, 1.271, 1.272, 2.23, 2.190, 2.192, 4.12, 6.10, 6.12, 6.49, 6.51 and 10.5 exhibit strong efficacy.

What is claimed is:

1. A pyrrolecarboxamide of the formula I

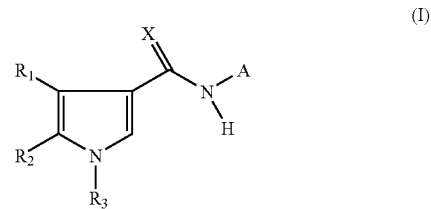

wherein

X is oxygen;

$R_1$ is $C_1$–$C_4$alkyl unsubstituted or substituted, with the exception of $CF_3$; $C_3$–$C_6$cycloalkyl unsubstituted or substituted; or halogen;

$R_2$ is hydrogen, $C_1$–$C_4$alkyl unsubstituted or substituted, $C_1$–$C_4$alkoxy unsubstituted or substituted, cyano or halogen;

$R_3$ is $C_1$–$C_4$alkyl unsubstituted or substituted; and

A is a substituted thiophene ring.

2. A compound of formula I according to claim 1, wherein
$R_1$ is $C_1$–$C_4$alkyl; $C_1$–$C_4$haloalkyl; $C_1$–$C_4$alkoxy-$C_1$–$C_4$alkyl; $C_1$–$C_4$haloalkoxy-$C_1$–$C_4$alkyl; $C_3$–$C_6$cycloalkyl unsubstituted or substituted by $C_1$–$C_4$alkyl, $C_1$–$C_4$haloalkyl, $C_1$–$C_4$alkoxy, $C_1$–$C_4$haloalkoxy, $C_1$–$C_4$alkoxy-$C_1$–$C_4$alkyl, $C_1$–$C_4$haloalkoxy-$C_1$–$C_4$alkyl or halogen; or halogen;
$R_2$ is hydrogen, $C_1$–$C_4$alkyl, $C_1$–$C_4$haloalkyl, $C_1$–$C_4$alkoxy, $C_1$–$C_4$haloalkoxy, $C_1$–$C_4$alkoxy-$C_1$–$C_4$alkyl, $C_1$–$C_4$haloalkoxy-$C_1$–$C_4$alkyl, cyano or halogen;
$R_3$ is $C_1$–$C_4$alkyl, $C_1$–$C_4$haloalkyl, $C_1$–$C_4$alkoxy-$C_1$–$C_4$alkyl or $C_1$–$C_4$haloalkoxy-$C_1$–$C_4$alkyl;
A is a group

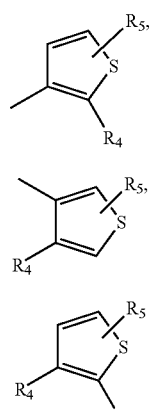

and
$R_4$ is $C_3$–$C_7$cycloalkyl, $C_4$–$C_7$cycloalkenyl, $C_5$–$C_7$cycloalkadienyl wherein the cycloalkyl group can be mono- to pentasubstituted by halogen, hydroxy, $C_1$–$C_4$alkyl, $C_1$–$C_4$alkoxy, $C_1$–$C_4$haloalkoxy, $C_2$–$C_4$alkenyl, $C_2$–$C_5$alkynyl, $C_1$–$C_4$haloalkyl; phenyl unsubstituted or substituted by halogen, nitro, cyano, CHO, $C_1$–$C_4$alkyl, $C_1$–$C_4$alkoxy, $C_1$–$C_4$haloalkoxy, $C_2$–$C_5$alkenyl, $C_2$–$C_5$alkynyl, $C_1$–$C_4$haloalkyl, COO$C_1$–$C_4$alkyl, $C_1$–$C_4$alkoxy-$C_1$–$C_4$alkyl, $C_1$–$C_4$alkyl-$C_1$–$C_4$alkoxy, $C_1$–$C_4$haloalkoxy-$C_1$–$C_4$alkyl, $C_1$–$C_4$haloalkyl-$C_1$–$C_4$alkoxy; thienyl, furyl, pyrrolyl, pyrazolyl, oxazolyl, thiazolyl, isoxazolyl, isothiazolyl, thiadiazolyl, imidazolyl, triazinyl, pyridyl, pyrazinyl, pyridazinyl or pyrimidinyl which are unsubstituted or substituted by halogen, $C_1$–$C_6$haloalkyl, $C_1$–$C_6$alkyl, $C_2$–$C_5$alkenyl, $C_2$–$C_5$alkynyl nitro, cyano, hydroxy, CHO, $C_1$–$C_6$alkoxy, COO$C_1$–$C_6$alkyl, $C_1$–$C_4$alkoxy-$C_1$–$C_4$alkyl, $C_1$–$C_4$haloalkoxy-$C_1$–$C_4$alkyl or $C_1$–$C_6$haloalkoxy; and
$R_5$ is hydrogen, cyano, nitro, halogen, $C_1$–$C_4$haloalkyl, $C_1$–$C_4$alkyl, $C_1$–$C_4$alkoxy-$C_1$–$C_4$alkyl, $C_1$–$C_4$haloalkoxy-$C_1$–$C_4$alkyl, $C_1$–$C_4$alkoxy or $C_1$–$C_4$haloalkoxy.

3. A compound of formula I according to claim 2, wherein
$R_1$ is $C_1$–$C_3$alkyl; $C_1$–$C_3$haloalkyl; $C_3$–$C_6$cycloalkyl unsubstituted or substituted by $C_1$–$C_3$alkyl, $C_1$–$C_3$haloalkyl or halogen;
$R_2$ is hydrogen, $C_1$–$C_4$alkyl or $C_1$–$C_4$haloalkyl;
$R_3$ is $C_1$–$C_4$alkyl, $C_1$–$C_3$haloalkyl or $C_1$–$C_3$alkoxy-$C_1$–$C_3$alkyl;
A is A2, A3, or A4;
$R_4$ is $C_5$–$C_7$cycloalkyl, unsubstituted or mono- to trisubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; $C_5$–$C_7$cycloalkenyl, unsubstituted or mono- to trisubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; $C_5$–$C_7$cyclodialkenyl, unsubstituted or mono- to disubstituted by halogen, hydroxy, $C_2$–$C_4$alkenyl, $C_2$–$C_4$alkynyl, $C_1$–$C_4$alkyl, $C_1$–$C_4$haloalkyl, $C_1$–$C_4$haloalkoxy or $C_1$–$C_4$alkoxy; thienyl, furyl, isoxazolyl, oxazolyl, thiadiazolyl, triazinyl, pyridyl, pyrimidinyl, pyrazinyl or pyridazinyl, which are unsubstituted or substituted by halogen, hydroxy, $C_1$–$C_4$alkyl, $C_1$–$C_4$haloalkyl, $C_1$–$C_4$alkoxy or $C_1$–$C_4$haloalkoxy; phenyl which is unsubstituted or substituted by halogen, $C_1$–$C_4$alkyl, $C_1$–$C_4$alkoxy, $C_1$–$C_4$haloalkyl or $C_1$–$C_4$haloalkoxy; and
$R_5$ is hydrogen, halogen, $C_1$–$C_4$alkyl, $C_1$–$C_4$alkoxy, $C_1$–$C_4$haloalkyl or $C_1$–$C_4$haloalkoxy.

4. A compound of formula I according to claim 3, wherein
A is A2, A3, or A4;
$R_1$ is $C_1$–$C_2$alkyl, $C_1$–$C_3$haloalkyl or cyclopropyl;
$R_2$ is hydrogen or $C_1$–$C_3$alkyl;
$R_3$ is $C_1$–$C_3$alkyl or $C_1$–$C_3$alkoxy-$C_1$–$C_3$alkyl;
$R_4$ is cyclohexyl, cyclohexenyl or cyclohexadienyl, which are unsubstituted or mono- to disubstituted by chloro, bromo, $C_1$–$C_2$alkyl, $C_1$–$C_2$haloalkyl or $C_1$–$C_2$haloalkoxy; thienyl, furyl, triazinyl, pyridyl, pyrazinyl, pyridazinyl or pyrimidinyl which are unsubstituted or substituted by halogen, $C_1$–$C_4$alkyl, $C_1$–$C_4$haloalkyl or $C_1$–$C_4$haloalkoxy; and
$R_5$ is hydrogen, halogen, $C_1$–$C_3$alkyl, $C_1$–$C_3$haloalkyl, $C_1$–$C_3$alkoxy or $C_1$–$C_3$haloalkoxy.

5. A process for the preparation of compounds of formula I which comprises reacting the starting materials according to the scheme

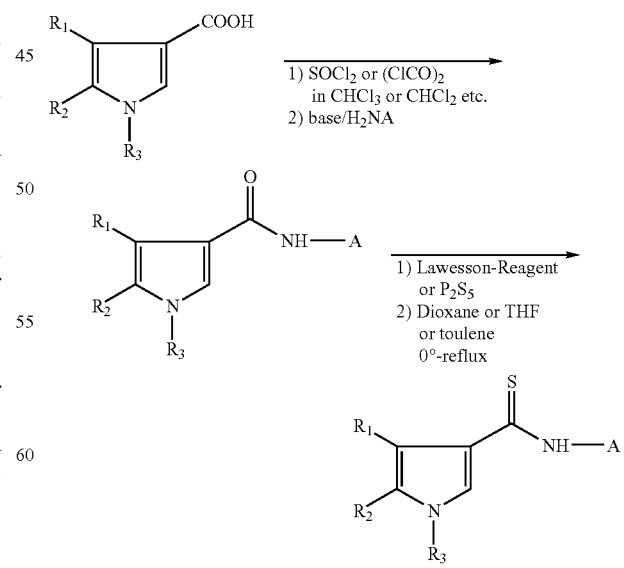

Base = NEt$_3$, Hünig-base, Na$_2$CO$_3$, K$_2$CO$_3$ and others wherein A, $R_1$, $R_2$ and $R_3$ are as defined for formula I in claim 1.

6. A composition for controlling microorganisms and preventing attack and infestation of plants therewith, wherein the active ingredient is a compound as claimed in claim 1 together with a suitable carrier.

7. A method of controlling or preventing infestation of cultivated plants by phytopathogenic microorganisms by application of a compound of formula I as claimed in claim 1 to plants, to parts thereof or the locus thereof.

* * * * *